(12) United States Patent
Rabin et al.

(10) Patent No.: US 9,193,995 B2
(45) Date of Patent: Nov. 24, 2015

(54) COMPOSITIONS FOR DETECTING HUMAN INTERFERON-ALPHA SUBTYPES AND METHODS OF USE

(75) Inventors: Ronald Rabin, Rockville, MD (US); Viraj Pramod Mane, Rockville, MD (US)

(73) Assignee: UNITED STATES DEPARTMENT OF HEALTH AND HUMAN SERVICES, Washington, DC (US)

(*) Notice: Subject to any disclaimer, the term of this patent is extended or adjusted under 35 U.S.C. 154(b) by 1126 days.

(21) Appl. No.: 13/130,346

(22) PCT Filed: Nov. 20, 2009

(86) PCT No.: PCT/US2009/065382
§ 371 (c)(1),
(2), (4) Date: Sep. 9, 2011

(87) PCT Pub. No.: WO2010/059970
PCT Pub. Date: May 27, 2010

(65) Prior Publication Data
US 2011/0311973 A1    Dec. 22, 2011

Related U.S. Application Data

(60) Provisional application No. 61/116,563, filed on Nov. 20, 2008.

(51) Int. Cl.
C12P 19/34    (2006.01)
C12Q 1/68     (2006.01)

(52) U.S. Cl.
CPC .................................. *C12Q 1/6858* (2013.01)

(58) Field of Classification Search
None
See application file for complete search history.

(56) References Cited

U.S. PATENT DOCUMENTS 4,683,195 A    7/1987    Mullis et al.
5,948,902 A    9/1999    Honkanen et al.

FOREIGN PATENT DOCUMENTS

WO    WO-2007106534    9/2007
WO    WO2010/059970    5/2010

OTHER PUBLICATIONS

Szubin et al. (2008) Journal of interferon & cytokine research 28:749-764 DOI:10.1089/jir.2008.0037.*
Marschall et al. (2003) JNCI Natl Cancer Inst vol. 95 (6): 437-448.*
Rychlik et al. (1989) vol. 17 No. 21 pp. 8543-8551.*
(Continued)

*Primary Examiner* — Suchira Pande
(74) *Attorney, Agent, or Firm* — Wilson Sonsini Goodrich & Rosati

(57) ABSTRACT

The invention provides highly sensitive, specific and efficient quantitative real-time PCR compositions, methods and assay kits to detect at least one IFN subtype and/or IFN subtype allotypic variants. Primer/probe sets complementary to the coding sequence of an IFN subtype of interest avoid spurious detection of degraded mRNA and enhances the correlation between the IFN subtype that is measured by the assays of the invention and the protein that is actually expressed. The invention also provides methods for designing primers and methods of using the compositions and assay kits. The compositions, kits, and methods of the invention may be used, for example, to monitor vaccine efficacy, autoimmune disease, chronic infections, or tumor therapy.

15 Claims, 12 Drawing Sheets

(56) References Cited

OTHER PUBLICATIONS

Altschul et al. (1997) "Gapped BLAST and PSI-BLAST: a new generation of protein database search programs" *Nucleic Acids Res.* 25:3389-3402.

Donnelly et al. (2004) "The expanded family of class II cytokines that share the IL-10 receptor-2 (IL-10R2) chain" *J Leukoc. Biol.* 76:314-321.

Mullis et al. (1986) "Specific enzymatic amplification of DNA in vitro: the polymerase chain reaction" *Cold Spring Harbor Symp. Quant. Biol.* 51:263.

PCT/US2009/065382 International Preliminary Report on Patentability dated Jun. 3, 2011.

PCT/US2009/065382 International Search Report and Written Opinion dated Aug. 13, 2010.

Pestka et al. (2004) "Interferons, interferon-like cytokines, and their receptors" *Immunol, Rev.* 202: 8/32.

Satterfield et al. (2007) "Tentacle probes: eliminating false positives without sacrificing sensitivity" *Nucleic Acids Res* 35(10):e76.

Gibson et al., "The use of real-time PCR methods in DNA sequence variation analysis," Clinica Chimica Acta, 363(1-2):32-47 (2006).

Hussain et al., "IFN-alpha1a gene is the major variant in the North American population," Journal of Interferon and Cytokine Research, 20(9):763-768 (2000).

Palmer et al., "Type I interferon subtypes produced by human peripheral mononuclear cells from one normal donor stimulated by viral and non-viral inducing factors," European Cytokine Network, 18(2):108-114 (2007).

Szubin et al., "Rigid interferon-alpha subtype responses of human plasmacytoid dendritic cells," Journal of Interferon and Cytokine Research, 28(12):749-763 (2008).

\* cited by examiner

FIGURE 1

| Gene | Forward Primer | | | | Probe**† | | | | Reverse Primer | | | |
|---|---|---|---|---|---|---|---|---|---|---|---|---|
| | SEQ ID NO | Sequence | Template position* | Conc (nM) | SEQ ID NO | Sequence | Template position | Conc (nM) | SEQ ID NO | Sequence | Template position | Conc (nM) |
| IFN-α1 | 30 | tagacaaattctgcaccgaac | 245-265 | 300 | 59 | ctcccacccTctcCtc (-) | 307-322 | 62.5 | 45 | agatggagtcciacttcatc | 333-352 | 300 |
| IFN-α2 | 31 | ggtagcaggaggacctigatg | 28-48 | 200 | 60 | cgcgatccccccaggaggagtttggcaacgatcgcg (+) | 115-138 | 250 | 46 | ggaggacaggaggatggtttcag | 152-172 | 200 |
| IFN-α4a/b | 32 44 | tcattctcctgcctgaagg Inhibitor: TCCTTTCTCC | 75-94 | 100 | 61 | ctCgggGaatcCgaaAtc (-) | 103-120 | 125 | 47 89 | gaggacagagatgcctgag Inhibitor: GAAGGCAGA | 152-171 | 100 |
| IFN-α4a | 33 | gatactcctgcacaaatgg | 45-64 | 300 | 62 88 | cgcgatcgcttgagcttctgaactgtgggatcgcg (-) Inhibitor: CTGGTTGCC | 135-158 | 125 | 48 | aaggtctgctgatcatctc | 175-194 | 300 |
| IFN-α4b | 34 | | | | 63 88 | cgcgatcgcttgagtcttctgaactgtgggatcgcg (-) Inhibitor: CTGGTTGCC | | 250 | 49 | | | |
| IFN-α5 | 35 | cacttctagacacaaattctacactg | 239-262 | 300 | 64 | ttcCacTccAacCtcct (-) | 305-321 | 125 | 50 | ggatagagtccacattcatcag | 331-352 | 300 |
| IFN-α6 | 36 | tgattcagcagcagccttcaatc | 179-199 | 500 | 65 | agcctcTcaTccCaagc (-) | 226-242 | 62.5 | 51 | tgctggtaaagttcagtatagag | 253-275 | 500 |
| IFN-α7 | 37 | cagacccacagcctgcgt | 13-30 | 150 | 66 | cgcgatcctggcacaaatggcacaaatctcctttgatcgcg (+) | 53-80 | 125 | 52 | aaactcctccctgggaattcg | 108-129 | 150 |
| IFN-α8 | 38 | gatgataaacagttccagaagg | 130-151 | 150 | 67 | ctcaTccAaaGcAGcAg (-) | 221-237 | 62.5 | 53 | aagttcgatgtagaattcatctag | 244-267 | 150 |
| IFN-α10 | 39 | gggacaaatggaagaatctc | 54-74 | 350 | 68 | agacatGatTTccGaaTcccc (+) | 97-117 | 62.5 | 54 | aactggttgccatcaaactc | 124-143 | 350 |
| IFN-α14 | 40 | aggaggaattgatggcaac | 119-138 | 150 | 69 | tccaGaaAgcTcaAgc (+) | 143-159 | 125 | 55 | agcagcagatgagttctttg | 209-228 | 150 |
| IFN-α16 | 41 | attgaactttcagcaactg | 259-279 | 350 | 70 | atgaCctAgaAgcCtgt (+) | 261-297 | 125 | 56 | ttcatcagggcaatctctc | 319-338 | 350 |
| IFN-α17 | 42 | aatgggaagaatctctcctttc | 66-90 | 300 | 71 | acagaccTgActTtggactt (+) | 95-114 | 125 | 57 | cttgagtctctgaactgg | 138-157 | 300 |
| IFN-α21 | 43 | tcatctgctactgggaacag | 217-237 | 250 | 72 | cgcgatctcctgtatcacgcaggcttccatgatcgcg (-) | 286-308 | 125 | 58 | cacattcatcaggggagtctc | 322-342 | 250 |
| IFN-λ1 | 79 | gttcaaatctctgtcaccac | 123-142 | 150 | 81 | cgaGctTcaAgaAggcc (+) | 152-168 | 125 | 84 | ttcagcttgagtgactcttc | 181-200 | 150 |
| IFN-λ2 | 80 | gccaaagatgcctagaagag | 166-186 | 150 | 82 | cgcgatcgcaggtgccactcccgcctctgatcgcg (+) | 206-226 | 125 | 85 | cagaaccttcagcgtcagg | 297-315 | 150 |
| IFN-λ3 | | | | 300 | 83 | cgcgatcgcaagtgcgctcccgcctctgatcgcg (+) | 206-226 | 125 | | | | 300 |

* Template position is relative to the start of the sequence for the mature protein gene product
** Sequence in italics denotes hairpin of the MB probes; capitalized letters denotes LNA analogues; Bold letters show difference in probes for when primers are common IFN-α4e and -α4b;
† each probe is labeled with a fluorophore on the 5' end and a quencher on the 3' end
+ denotes probe anneals to sense strand, - denotes probe anneals to anti-sense strand of the PCR product.
Inhibitors are 9- or 10-mers of LNA analogues; concentrations of inhibitors: TCCTTTCTCC (SEQ ID NO: 44) (1000 nM); GAAGGCAGA (SEQ ID NO: 89) (100 nM); CTGGTTGCC (SEQ ID NO: 88) (250 nM)

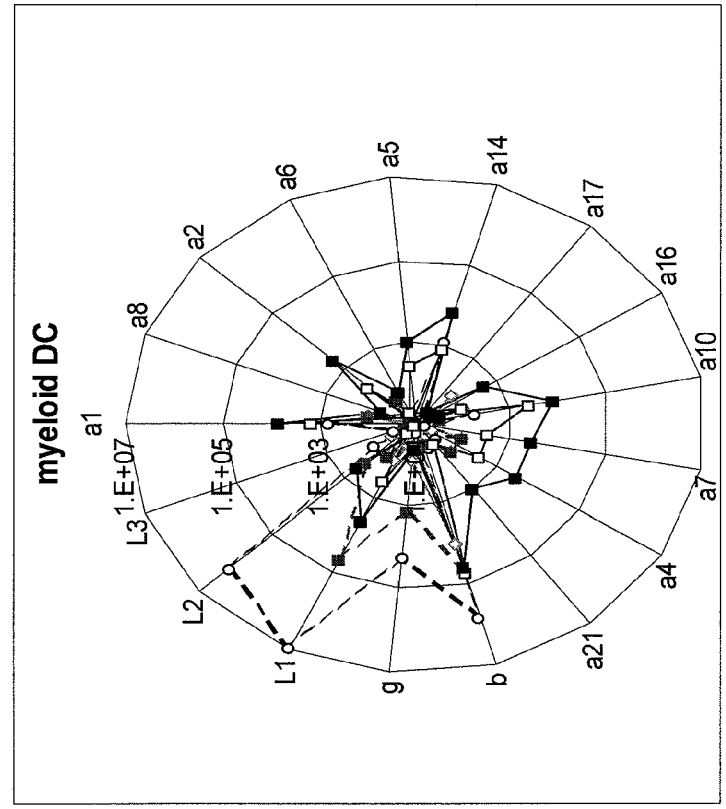
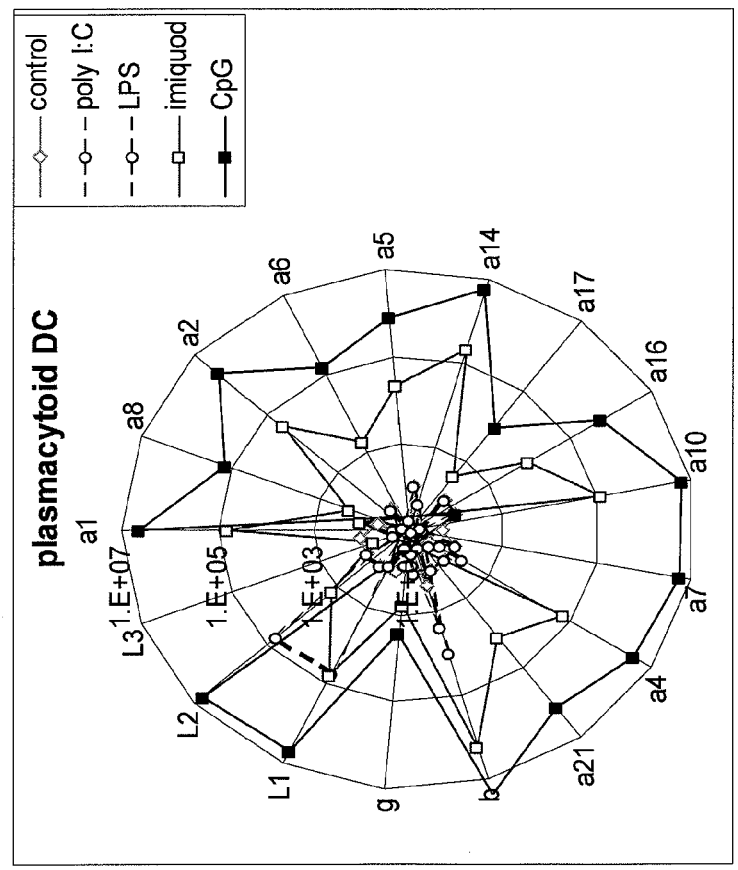
FIGURE 9D-E

COMPOSITIONS FOR DETECTING HUMAN INTERFERON-ALPHA SUBTYPES AND METHODS OF USE

STATEMENT OF RIGHTS TO INVENTIONS MADE UNDER FEDERALLY-SPONSORED RESEARCH AND DEVELOPMENT

The work performed during the development of this disclosure utilized intramural support from the National Institutes of Health and the Food and Drug Administration. The United States government has certain rights in the disclosure.

This application is a national stage application under 35 U.S.C. §371 of International Application PCT/US2009/065382, filed Nov. 20, 2009, which claims priority under 35 U.S.C. §119(e) from U.S. provisional application 61/116,563, filed Nov. 20, 2008 (now expired). The contents of both applications are hereby incorporated by reference in their entirety.

SEQUENCE LISTING

The instant application contains a Sequence Listing which has been submitted via EFS-Web and is hereby incorporated by reference in its entirety. Said ASCII copy, created on May 20, 2011, is named Sequence_Listing.txt, and is 52,237 bytes in size.

BACKGROUND OF THE INVENTION

This invention relates to primers, probes, assay kits and methods for identifying and discriminating between interferon (IFN) subtypes.

Interferons are secreted cellular proteins that are comprised of type I, type II and type III families based upon sequence similarities and receptor usage. IFN-γ, known also as immune interferon, is the only Type II interferon whereas the Type I human interferons consist of several classes: IFN-α, IFN-β, IFN-ε, IFN-ω, IFN-κ and IFN-τ. IFN-τ is only found in ungulates; there is no human IFN-τ. There is only one human IFN-β and one human IFN-ω, but a family of multiple IFN-α species exists, namely, thirteen highly homologous genes, two of which have an identical coding sequence. IFNs are up-regulated in response to varied native and pathologic stimuli. Pathogens such as viruses are recognized by components of the innate immune system including toll-like receptors (TLR) and retinoic acid-inducible gene-1-like (RIG-1) receptors. The rapid recognition of pathogen stimuli coordinated with the appropriate cytokine response are crucial for the control of many pathogenic organisms. To illustrate, rather than a single interferon responding to a specific infectious agent, the host interferon response comprises coordinated expression of many different interferon genes and proteins designed a) to limit pathogen replication in infected cells and b) to coordinate with the adaptive immune system to limit dissemination. This "interferon expression signature" varies over time, coordinating and responding to the expression of thousands of genes.

Importantly, it has been clearly established in the literature that each individual interferon protein possesses unique biological activities. Moreover, limited qualitative studies have shown that the expression patterns of the interferon alpha subtypes vary with stimuli and time. Consequently, assays are warranted that can detect and differentiate each of the individual interferons.

The IFNs exhibit anti-viral, immunoregulatory, and antiproliferative activity, and the clinical potential of interferons has been recognized. However, little is known about unique roles for any of the individual IFN-alpha subtypes because there is no sensitive and specific system to measure their individual expression.

Thus, one of the current research dilemmas within the interferon world is the role of the various IFN types and subtypes in various diseases. Currently, tools are not available to address these questions, although several pharmaceutical companies are investigating the modulation of individual IFN subtypes as potential therapies for a variety of human diseases, including systemic lupus erythematosis, multiple sclerosis, various cancers, hepatitis C, human immunodeficiency virus (HIV) and others. The availability of tools which address both the individual and combined expression profiles of interferons and/or other cytokines will greatly benefit not only current research, but will enable other areas of disease research where interferons have not even been implicated due to a lack of suitable tools.

The invention described herein provides nucleic acid amplification techniques for differentiating between highly related nucleic acid molecules. In current embodiments, polymerase chain reaction (PCR) and novel probe/primer pairs are used to differentiate between IFN subtypes. The invention described herein will be useful for elucidating fundamental roles of various closely related interferons and subtypes and, in the process, greatly advance what is known about immunological processes particularly in the context of the subtle genetic differences between humans. The invention is expected to be useful in relation to other biological molecules for which different, highly related subtypes occur in the body. The instant invention may be useful, for example, for identifying subtypes of IFN as a surrogate marker for vaccine efficacy in clinical trials, to monitor clinical progression or remission of chronic infections, autoimmune diseases or cancer, or to determine responses to therapy for those and other diseases. Moreover, the instant invention may be useful, inter alia, in molecular diagnostic methods and in enabling skilled professionals to individually design and tailor therapeutic treatment regimens for the individual patient and the particular medical condition presented. The ability to deliver personalized medicine may be especially important in treating individuals who are refractory to the standard regiment of care. Thus, there is a need for a rapid comprehensive test for determining the presence of IFN-subtypes.

SUMMARY OF THE INVENTION

A highly sensitive and specific quantitative real-time PCR (RT-PCR) assay to detect each of the IFN subtypes and allotypic variants of IFNs is provided. The assay exploits two modifications of probe-based RT-PCR: molecular beacons (MB) and locked nucleic acids (LNA). The invention advantageously allows amplification and detection of all of an IFN's subtypes, or subsets within that group, simultaneously with similar sensitivity and under the same reaction conditions. In some embodiments, the target sequence of the primer/probe sets are complementary to mature coding sequence because the 3' untranslated regions of mRNA transcripts may have target sites for micro-RNA molecules that initiate degradation of downstream coding sequence. Primer/probe sets complementary to coding sequence avoid spurious detection of degraded mRNA and enhance the correlation between the IFN subtype mRNA that is measured by this assay and the protein that is actually expressed. The primer/probe sets, associated methods using them (and a diagnostic kit for performing such methods) can be used to establish patterns of IFN subtype expression that may be associated with protection from, or pathogenesis of many diseases, including infections, autoimmunity and cancer. Identifying patterns of IFN subtype expression may be used to monitor vaccine efficacy, treatment of various autoimmune diseases and chronic infections, or tumor therapy, to name a few.

In one aspect, the invention provides a composition for amplifying at least one sequence encoding an IFN-alpha subtype of interest comprising a forward primer and a reverse primer that together enable specific amplification of the sequence encoding the IFN-alpha subtype of interest from a composition comprising a plurality of IFN subtype templates. The at least one sequence encoding the IFN-alpha subtype of interest may be a single allelic variant. The IFN-alpha subtype may be selected from the group consisting of IFN-alpha1a/b, IFN-alpha1b, IFN-alpha1a, IFN-alpha2a/b, IFN-alpha2a, IFN-alpha2b, IFN-alpha4a/b, IFN-alpha4a, IFN-alpha4b, IFN-alpha5, IFN-alpha6, IFN-alpha7, IFN-alpha8, IFN-alpha10, IFN-alpha14, IFN-alpha16, IFN-alpha17, and IFN-alpha2.

In some embodiments, the forward primer and the reverse primer for the at least one sequence encoding the IFN-alpha subtype are selected from the group consisting of: for IFN-alpha1a/b, the forward primer comprises SEQ ID NO: 30 and the reverse primer comprises SEQ ID NO: 45; for IFN-alpha2, the forward primer comprises SEQ ID NO: 31 and the reverse primer comprises SEQ ID NO: 46; for IFN-alpha4a/b, the forward primer comprises SEQ ID NO: 32 and the reverse primer comprises SEQ ID NO: 47; for IFN-alpha4a, the forward primer comprises SEQ ID NO: 33 and the reverse primer comprises SEQ ID NO: 48; for IFN-alpha4b, the forward primer comprises SEQ ID NO: 34 and the reverse primer comprises SEQ ID NO: 49; for IFN-alpha5, the forward primer comprises SEQ ID NO: 35 and the reverse primer comprises SEQ ID NO: 50; for IFN-alpha6, the forward primer comprises SEQ ID NO: 36 and the reverse primer comprises SEQ ID NO: 51; for IFN-alpha7, the forward primer comprises SEQ ID NO: 37 and the reverse primer comprises SEQ ID NO: 52; for IFN-alpha8, the forward primer comprises SEQ ID NO: 38 and the reverse primer comprises SEQ ID NO: 53; for IFN-alpha10, the forward primer comprises SEQ ID NO: 39 and the reverse primer comprises SEQ ID NO: 54; for IFN-alpha14, the forward primer comprises SEQ ID NO: 40 and the reverse primer comprises SEQ ID NO: 55; for IFN-alpha16, the forward primer comprises SEQ ID NO: 41 and the reverse primer comprises SEQ ID NO: 56; for IFN-alpha17, the forward primer comprises SEQ ID NO: 42 and the reverse primer comprises SEQ ID NO: 57; and for IFN-alpha21, the forward primer comprises SEQ ID NO: 43 and the reverse primer comprises SEQ ID NO: 58.

Each of the forward and reverse primers in the composition may have a primer extension temperature between 50° C. and 60° C. Some compositions may comprise a forward primer and a reverse primer for each of the IFN-alpha subtypes.

The composition may further comprise an inhibitor. The composition may further comprise a probe. At least one of the inhibitor, forward primer, reverse primer or probe may comprise a locked nucleic acid. At least one of the forward primer, reverse primer or probe may comprise a molecular beacon. The inhibitor for a sequence encoding an IFN-alpha subtype may be selected from the group consisting of: for IFN-alpha4a/b, the inhibitor comprises SEQ ID NOS: 44 and 89; for IFN-alpha4a, the inhibitor comprises SEQ ID NO: 88; and for IFn-alpha4b, the inhibitor comprises SEQ ID NO: 88.

The probe may identify a sequence encoding a single IFN-alpha subtype allelic variant. The probe for a sequence encoding an IFN-alpha subtype may be selected from the group consisting of: for IFN-alpha1a/b, the probe comprises SEQ ID NO: 59; for IFN-alpha2, the probe comprises SEQ ID NO: 60; for IFN-alpha4a/b, the probe comprises SEQ ID NO: 61; for IFN-alpha4a, the probe comprises SEQ ID NO: 62; for IFN-alpha4b, the probe comprises SEQ ID NO: 63; for IFN-alpha5, the probe comprises SEQ ID NO: 64; for IFN-alpha6, the probe comprises SEQ ID NO: 65; for IFN-alpha7, the probe comprises SEQ ID NO: 66; for IFN-alpha8, the probe comprises SEQ ID NO: 67; for IFN-alpha10, the probe comprises SEQ ID NO: 68; for IFN-alpha14, the probe comprises SEQ ID NO: 69; for IFN-alpha16, the probe comprises SEQ ID NO: 70; for IFN-alpha17, the probe comprises SEQ ID NO: 71; and for IFN-alpha21, the probe comprises SEQ ID NO: 72.

The composition may further comprise a DS-agent. The DS-agent may be a dye that binds to a double stranded nucleic acid. The dye may be Sybr green. The probe may further comprise a capture region or a detectable label, such as Texas-Red®, fluorescein isothiocyanate, FAM, TAMRA, Alexa fluor, a cyanine dye, a quencher, or biotin.

The composition may further comprise a control. The composition may have an efficiency of at least about 1.9 or at least about 1.95. The composition may have a sensitivity sufficient to detect at least about 1-10 copies of sequence encoding the IFN-alpha subtype of interest per reaction. The composition may have a specificity of at least about 5 cycles difference between specific and nonspecific amplification. The efficiency, sensitivity and specificity may be achieved with PCR reaction conditions comprising: Stage 1: 50° C. for two minutes; Stage 2: 95° C. for three minutes; and Stage 3: 40 repeats of 95° C. for 15 seconds followed by 59° C. for one minute.

In another embodiment, the invention provides a kit for the detection of at least one specific IFN-alpha subtype comprising a composition as described above. The kit may further comprise containers for each of the IFN-alpha subtypes, each container comprising a forward primer and a reverse primer that together enable specific amplification of a sequence encoding a single IFN-alpha subtype from a composition comprising a plurality of IFN subtype templates. The at least one sequence encoding the IFN-alpha subtype of interest may be a single allelic variant. The IFN-alpha subtypes may be selected from the group consisting of IFN-alpha1b, IFN-alpha1a, IFN-alpha2a, IFN-alpha2b, IFN-alpha4a, IFN-alpha4b, IFN-alpha5, IFN-alpha6, IFN-alpha7, IFN-alpha8, IFN-alpha10, IFN-alpha14, IFN-alpha16, IFN-alpha17, and IFN-alpha21.

A container of the kit may further comprises a probe that specifically hybridizes to the sequence encoding the single IFN-alpha subtype. Each container may further comprise an inhibitor and/or a control. The container may be a tube, a well in a multiwell plate, a channel, or a well on a chip. Each of the forward and reverse primers in the kit may have a primer extension temperature between 50° C. and 60° C.

Each amplification reaction in the kit may have an efficiency of at least about 1.90; a sensitivity sufficient to detect at least about 1-10 copies of the sequence encoding the IFN subtype of interest per reaction; and a specificity of at least about 9 cycles difference between specific and nonspecific amplification. At least one of the efficiency, sensitivity and specificity may be achieved with PCR reaction conditions comprising: Stage 1: 50° C. for two minutes; Stage 2: 95° C. for three minutes; and Stage 3: 40 repeats of 95° C. for 15 seconds followed by 59° C. for one minute. The kit may also comprise a plurality of forward primers and reverse primers in a single multiplex reaction vessel, wherein each set of forward primer and reverse primer together enables specific amplification of a sequence encoding a single IFN-alpha subtype from a composition comprising a plurality of IFN subtype templates.

In another embodiment, the invention provides a method of detecting the presence of at least one IFN-alpha subtype of interest in a sample comprising: a) contacting the sample with the composition comprising a forward primer and a reverse primer that enable specific amplification of a sequence encoding the IFN-alpha subtype of interest or the kit comprising a forward primer and a reverse primer that enable specific amplification of a sequence encoding the IFN-alpha subtype of interest under conditions suitable for amplification of the nucleic acid sequence of the IFN-alpha subtype of interest; and b) detecting an amplification product for the IFN-alpha subtype of interest, wherein the presence of the amplification product indicates that the IFN-alpha subtype of interest is present in the sample.

In another embodiment, the invention provides a method of monitoring the efficacy of a treatment for a condition comprising: a) contacting a sample with the composition comprising a forward primer and a reverse primer that enable specific amplification of a sequence encoding the IFN-alpha subtype of interest or the kit comprising a forward primer and a reverse primer that enable specific amplification of a sequence encoding the IFN-alpha subtype of interest under conditions suitable for amplification of the at least one IFN-alpha subtype of interest; b) detecting an amplification product for the IFN-alpha subtype of interest; and c) generating an expression profile for the at least one IFN-alpha subtype of interest. The treatment may comprise administering an immunomodulatory drug. The method may further comprise comparing the expression profile for the at least one IFN-alpha subtype of interest to an expression pattern for the at least one IFN-alpha subtype of interest in a sample without the condition. The treatment is selected from the group consisting of a vaccine, an immunomodulatory drug, a cancer chemotherapy, and an autoimmune condition therapy.

In another embodiment, the invention provides a method of detecting a condition or susceptibility to the condition, comprising: a) contacting a sample with the composition comprising a forward primer and a reverse primer that enable specific amplification of a sequence encoding the IFN-alpha subtype of interest or the kit comprising a forward primer and a reverse primer that enable specific amplification of a sequence encoding the IFN-alpha subtype of interest under conditions suitable for amplification of the nucleic acid sequence of at least one IFN-alpha subtype of interest; b) detecting an amplification product for the IFN-alpha subtype of interest; c) generating an expression profile for the at least one IFN-alpha subtype of interest; and d) comparing the expression profile for the at least one IFN-alpha subtype of interest to one or more known gene expression profiles of the at least one IFN-alpha subtype of interest, wherein the known gene expression profile(s) is associated with a disease. The method may be performed on multiple samples, each sample comprising a different region of cells or tissue.

Any of these methods may be used to detect an IFN-alpha subtype selected from the group consisting of IFN-alpha1b, IFN-alpha1a, IFN-alpha2a, IFN-alpha2b, IFN-alpha4a, IFN-alpha4b, IFN-alpha5, IFN-alpha6, IFN-alpha7, IFN-alpha8, IFN-alpha10, IFN-alpha14, IFN-alpha16, IFN-alpha17, and IFN-alpha21.

The sample may be from a subject having a condition selected from the group consisting of: cancer, a viral infection, a bacterial infection, an inflammatory disease and an autoimmune disease. The sample may be selected from the group consisting of a tissue sample, cell sample, bodily fluid, urine, blood, serum, plasma, leukocytes, monocytes, peripheral blood leukocytes (PBL), lymph, saliva, cerebrospinal fluid (CSF), synovial fluid, bronchoalveolar lavage (BAL), pericardial fluid, spinal fluid, pleural fluid, pleural effusion, mucus, breast milk, amniotic fluid, vaginal fluid, semen, prostatic fluid, ascites, ascitic fluid, peritoneal fluid, aqueous humor, vitreous humor, tears, rheum, perspiration, cystic fluid, gastric acid, and tumor tissue sample.

In another embodiment, the invention provides a method for designing a primer pair for sequence encoding an IFN-alpha subtype comprising: a) identifying a unique region of an IFN-alpha subtype sequence; b) generating at least one pair of primers that hybridize to the unique region of IFN-alpha subtype sequence; c) determining the sensitivity of the at least one pair of primers and selecting at least one primer pair with a sensitivity sufficient to detect at least about 1-10 copies of the sequence encoding the IFN-alpha subtype of interest per reaction; d) determining the specificity of the at least on primer pair selected in (c) and selecting at least one primer pair with a specificity of at least about 5 cycles difference between specific and nonspecific amplification; e) determining the efficiency of the at least on primer pair selected in (d) and selecting at least one primer pair with an efficiency of at least about 1.90. The primer pair may heave a primer extension temperature in the range of 50° C. to 60° C.

BRIEF DESCRIPTION OF THE FIGURES

FIG. 1 is a chart of exemplary forward primers, reverse primers, probes and inhibitors for IFN-alpha and IFN-lambda subtypes.

DETAILED DESCRIPTION

Figure 2:
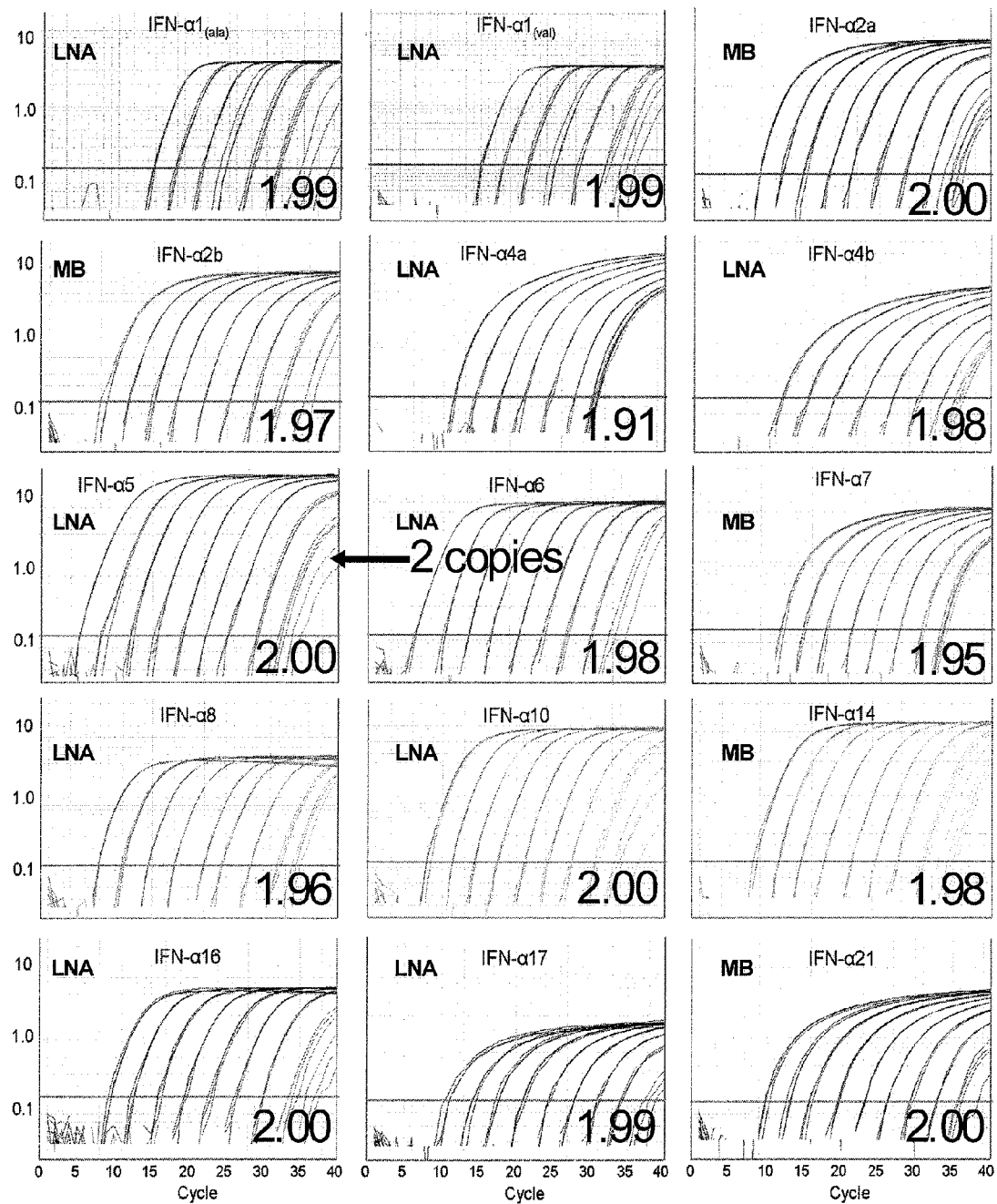
FIG. 2 is a panel of graphs depicting template dilutions for each IFN-alpha primer/probe set. In each subpanel, the primer/probe set, the type of probe (MB or LNA), and template are indicated. Fluorescence amplitude is denoted on the Y-axis while cycle number is indicated on the X-axis. Efficiency calculations are indicated for each graph.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can also be used in the practice or testing of the present invention. All publications and other references mentioned herein are incorporated by reference in their entirety. In case of conflict, the present specification, including definitions, will control. Although a number of documents are cited herein, this citation does not constitute an admission that any of these documents forms part of the common general knowledge in the art. Throughout this specification and claims, the word "comprise," or variations such as "comprises" or "comprising" will be understood to imply the inclusion of a stated integer or group of integers but not the exclusion of any other integer or group of integers. Unless otherwise required by context, singular terms shall include pluralities and plural terms shall include the singular. The materials, methods, and examples are illustrative only and not intended to be limiting.

The practice of the invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; Nucleic Acid Hybridization (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

In the nucleotide and amino acid sequences described herein within the sequence listing, with respect to a nucleotide sequence, an "n" or "x" can refer to any nucleotide, whereas with respect to a protein sequence, an "n" or "x" can refer to any amino acid.

As used herein, the term "comprising" is an open-ended term that includes the specific elements and may include additional, unrecited elements. "Comprising" may be synonymous with "including" or "containing". "Comprising" may also, separately and independently of the above definition, be read as "consisting essentially of" or "consisting of". As used herein, "consisting of" is a closed term that includes only the specific elements recited, and "consisting essentially of" includes the specific elements recited and may include additional unrecited, nonmaterial elements.

The term "sequence" includes nucleotide and amino acid sequences.

The term oligopeptide refers to an amino acid sequence between 2 and about 20 amino acids in length. The term oligonucleotide refers to a nucleotide sequence between 2 and about 50 nucleotides in length.

An "allele" refers to any of two or more alternative forms of a gene that occupy the same locus on a chromosome. If two alleles within a diploid individual are identical by descent (that is, both alleles are direct descendants of a single allele in an ancestor), such alleles are called autozygous. If the alleles are not identical by descent, they are called allozygous. If two copies of same allele is present in an individual, the individual is homozygous for that gene. If different alleles are present in an individual, the individual is heterozygous for that gene.

The term "disease state" refers to a physiological state of a cell, a tissue, organ or of a whole mammal in which an interruption, cessation, or disorder of cellular or body functions, systems or organs has occurred.

Unless otherwise expressly provided, the terms "interferon", "IFN", "human interferon", "human IFN", and "hIFN" are used herein to refer to all species of native and/or novel sequences of human interferons, whether now known or hereafter discovered, including all subtypes of the native sequence human interferons. The invention encompasses all types of IFNs, including, without limitation, IFN-alpha, IFN-beta, IFN-delta, IFN-epsilon, IFN-kappa, IFN-tau, IFN-omega, Limitin, IFN-gamma, IFN-lambda-1, lambda-2, lambda-3, and the like. An exemplary sequence for IFN-beta nucleotide is shown as SEQ ID NO: 86. An exemplary sequence for IFN-gamma nucleotide sequence is shown as SEQ ID NO: 87. In certain preferred embodiments, the IFN has subtypes, i.e., IFN-alpha subtypes, IFN-lambda2 and IFN-lambda3. IFN-alpha is used as an exemplary embodiment throughout the specification. However, it will be understood to those skilled in the art that the embodiments described herein apply to any other IFN subtypes as well.

"Locked Nucleic Acids" or "LNA" as used herein refer to a class of nucleic acid analogues in which the ribose ring is "locked" by a methylene bridge connecting the 2'-O atom with the 4'-C atom. LNA nucleosides contain the six common nucleobases (T, C, G, A, U and mC) that appear in DNA and RNA and thus are able to form base-pairs according to standard Watson-Crick base pairing rules. Oligonucleotides incorporating LNA have increased thermal stability and improved discriminative power with respect to their nucleic acid targets. LNA can be mixed with DNA, RNA and other nucleic acid analogs using standard phosphoramidite synthesis chemistry. LNA oligonucleotides can easily be labeled with standard oligonucleotide tags such as DIG, fluorescent dyes, biotin, amino-linkers, etc.

"Molecular beacons" or "MB" as used herein refer to a probe comprising a fluorescent label attached to one end of a polynucleotide and a quencher attached to the other. Complementary base-pairs near the label and quencher cause a hairpin-like structure, placing the fluorophore and quencher in proximity. This hairpin opens in the presence of the target producing an increase in fluorescence. The proximity of the quencher to the fluorophore can result in reductions of fluorescent intensity of up to 98%. The efficiency can further be adjusted by altering the stem strength (length of the stem) which affects the number of beacons in the open state in the absence of the target.

The term "native sequence" in connection with type I or II interferon, or any other polypeptide, refers to a polypeptide that has the same amino acid sequence as a corresponding polypeptide derived from nature, regardless of its mode of preparation. Such native sequence polypeptide can be isolated from nature or can be produced by recombinant and/or synthetic means or any combinations thereof. The term "native sequence" specifically encompasses naturally-occurring truncated or secreted forms (e.g., an extracellular domain sequence), naturally-occurring variant forms (e.g., alternatively spliced forms) and naturally-occurring allelic variants of the full length polypeptides.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic nucleic acid adaptors or linkers are used in accordance with conventional practice.

"Percent (%) amino acid sequence identity" with respect to the polypeptide sequences referred to herein is defined as the percentage of amino acid residues in a candidate sequence that are identical with the amino acid residues in a sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, or Megalign (DNASTAR) software. Those skilled in the art can determine appropriate parameters for measuring alignment, including any algorithms needed to achieve maximal alignment over the full-length of the sequences being compared.

For purposes herein, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Amino acid sequence identity may be determined using the sequence comparison program NCBI-BLAST2 (Altschul et al., Nucleic Acids Res. 25:3389-3402 (1997)). The NCBI-BLAST2 sequence comparison program may be downloaded from ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

For purposes herein, the % nucleic acid sequence identity of a given nucleic acid sequence A to, with, or against a given nucleic acid sequence B (which can alternatively be phrased as a given nucleic acid sequence A that has or comprises a certain % nucleic acid sequence identity to, with, or against a given amino acid sequence B) is calculated as follows:

100 times the fraction X/Y where X is the number of nucleic acid residues scored as identical matches by the sequence alignment program's alignment of A and B, and where Y is the total number of nucleic acid residues in B. It will be appreciated that where the length of nucleic acid sequence A is not equal to the length of nucleic acid sequence B, the % nucleic acid sequence identity of A to B will not equal the % nucleic acid sequence identity of B to A. Nucleic acid sequence identity may be determined using the sequence comparison program NCBI-BLAST2 (Altschul et al., Nucleic Acids Res. 25:3389-3402 (1997)). The NCBI-BLAST2 sequence comparison program may be downloaded, e.g., from ncbi.nlm.nih.gov. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for nucleic acid sequence comparisons, the % nucleic acid sequence identity of a given nucleic acid sequence A to, with, or against a given nucleic acid sequence B (which can alternatively be phrased as a given nucleic acid sequence A that has or comprises a certain % nucleic acid sequence identity to, with, or against a given nucleic acid sequence B) is calculated as follows:

100 times the fraction X/Y where X is the number of nucleic acid residues scored as identical matches by the sequence alignment program NCBI-BLAST2 in that program's alignment of A and B, and where Y is the total number of nucleic acid residues in B. It will be appreciated that where the length of nucleic acid sequence A is not equal to the length of nucleic acid sequence B, the % nucleic acid sequence identity of A to B will not equal the % nucleic acid sequence identity of B to A.

"Polymerase chain reaction" or "PCR" refers to a procedure or technique in which minute amounts of a specific piece of nucleic acid, RNA and/or DNA, are amplified as generally described, for example, in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify, for example, specific RNA sequences, specific DNA sequences from total genomic DNA, and cDNA transcribed from total cellular RNA, bacteriophage or plasmid sequences. See generally Mullis et al., Cold Spring Harbor Symp. Quant. Biol. 51:263 (1987); Erlich, ed., PCR Technology (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

The term "primer" refers to a nucleic acid capable of acting as a point of initiation of synthesis along a complementary strand when conditions are suitable for synthesis of a primer extension product. The synthesizing conditions include the presence of four different bases and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

The term "probe" refers to a nucleic acid that hybridizes to a target sequence. In some embodiments, a probe includes about 8, about 9, about 10, about 11, about 12, about 13, about 14, about 15, about 16, about 17, about 18, about 19, or about 20 nucleotides. A probe also includes about 25 nucleotides, about 30 nucleotides, about 40 nucleotides, about 50 nucleotides, about 60 nucleotides, about 70 nucleotides, about 75 nucleotides, about 80 nucleotides, about 90 nucleotides, about 100 nucleotides, about 110 nucleotides, about 115 nucleotides, about 120 nucleotides, about 130 nucleotides, about 140 nucleotides, about 150 nucleotides, about 175 nucleotides, about 187 nucleotides, about 200 nucleotides, about 225 nucleotides, and about 250 nucleotides, or any integer in between. A probe can further include a detectable label. Probes may include detectable labels, which include, but are not limited to, a fluorophore (e.g., Texas-Red®, Fluorescein isothiocyanate, etc.,) and a hapten, (e.g., biotin). A detectable label can be covalently attached directly to a probe oligonucleotide, e.g., located at the probe's 5' end or at the probe's 3' end. A probe including a fluorophore may also further include a quencher, e.g., Black Hole Quencher™, Iowa Black™, etc.

The terms "nucleic acid" and "polynucleotide" are used interchangeably herein to describe a polymer of any length, e.g., greater than about 10 bases, greater than about 100 bases, greater than about 500 bases, greater than 1000 bases, usually up to about 10,000 or more, or any integer in between. Nucleic acids are composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "melting temperature" or "$T_m$" refers to the temperature where the DNA duplex will dissociate and become single stranded. Thus, Tm is an indication of duplex stability.

The terms "hybridize" or "hybridization," as is known to those of ordinary skill in the art, refer to the binding or duplexing of a nucleic acid molecule to a particular nucleotide sequence under suitable conditions, e.g., under stringent conditions. The term "stringent conditions" (or "stringent hybridization conditions") as used herein refers to conditions that are compatible to produce binding pairs of nucleic acids, e.g., surface bound and solution phase nucleic acids, of sufficient complementarity to provide for a desired level of specificity in an assay while being less compatible to the formation of binding pairs between binding members of insufficient complementarity to provide for the desired specificity. Stringent conditions are the summation or combination (totality) of both hybridization and wash conditions.

The term "stringent assay conditions" as used herein refers to conditions that are compatible to produce binding pairs of nucleic acids, e.g., probes and targets, of sufficient complementarity to provide for the desired level of specificity in the assay while being incompatible to the formation of binding pairs between binding members of insufficient complementarity to provide for the desired specificity. The term stringent assay conditions refers to the combination of hybridization and wash conditions.

A "stringent hybridization" and "stringent hybridization wash conditions" in the context of nucleic acid hybridization (e.g., as in array, Southern or Northern hybridizations) are sequence dependent, and are different under different environmental parameters. Stringent hybridization conditions that can be used to identify nucleic acids within the scope of the invention can include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. Exemplary stringent hybridization conditions can also include a hybridization in a buffer of 40% formamide, 1 M NaCl, and 1% SDS at 37° C., and a wash in 1×SSC at 45° C. Alternatively, hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. can be employed. Yet additional stringent hybridization conditions include hybridization at 60° C. or higher and 3×SSC (450 mM sodium chloride/45 mM sodium citrate) or incubation at 42° C. in a solution containing 30% formamide, 1M NaCl, 0.5% sodium sarcosine, 50 mM MES, pH 6.5. Those of ordinary skill will readily recognize that alternative but comparable hybridization and wash conditions can be utilized to provide conditions of similar stringency.

In certain embodiments, the stringency of the wash conditions determine whether a nucleic acid is specifically hybridized to a probe. Wash conditions used to identify nucleic acids may include, e.g.: a salt concentration of about 0.02 M at pH 7 and a temperature of about 20° C. to about 40° C.; or, a salt concentration of about 0.15 M NaCl at 72° C. for about 15 minutes; or, a salt concentration of about 0.2×SSC at a temperature of about 30° C. to about 50° C. for about 2 to about 20 minutes; or, the hybridization complex is washed twice with a solution with a salt concentration of about 2×SSC containing 1% SDS at room temperature for 15 minutes and then washed twice by 0.1×SSC containing 0.1% SDS at 37° C. for 15 minutes; or, equivalent conditions. Stringent conditions for washing can also be, e.g., 0.2×SSC/0.1% SDS at 42° C. See Sambrook, Ausubel, or Tijssen (cited below) for detailed descriptions of equivalent hybridization and wash conditions and for reagents and buffers, e.g., SSC buffers and equivalent reagents and conditions.

As used herein the term "sensitivity" refers to the fewest number of molecules of the target that can be detected.

As used herein the term "specificity" refers to the selective detection of the template that is being probed relative to any of the other similar sequences. Specificity may be graded (e.g., high specificity being less than total), with total specificity defined as the detection of only the template that is being probed and not any of the other similar sequences.

As used herein, the term "genotype" means a sequence of nucleotide pair(s) found at one or more polymorphic sites in a locus on a pair of homologous chromosomes in an individual. Genotype may refer to the specific sequence of the gene for each of the IFN subtypes.

As used herein the term "subtype" refers to IFN subtype polypeptides or polynucleotides. "Subtype" may refer to any of two or more functionally similar proteins that have identical or similar amino acid sequences and are either encoded by different genes, or by RNA transcripts from the same gene which have had different exons removed. "Subtype" also may refer to any of the sequences encoding such proteins, including mature and immature sequences. Thus, "subtype" encompasses the IFN subtype genes as well as the protein products of the IFN subtype genes, unless stated or otherwise understood by context to refer to only one or the other.

As used herein, the term "about" modifying the quantity of an ingredient, parameter, calculation, or measurement in the compositions of the invention or employed in the methods of the invention refers to variation in the numerical quantity that can occur, for example, through typical measuring and liquid handling procedures used for making DNA, probes, primers, or solutions in the real world; through inadvertent error in these procedures; through differences in the manufacture, source, or purity of the ingredients employed to make the compositions or carry out the methods; and the like without having a substantial effect on the chemical or physical attributes of the compositions or methods of the invention. The term about also encompasses amounts that differ due to different equilibrium conditions for a composition resulting from a particular initial mixture. Whether or not modified by the term "about", the claims include equivalents to the quantities.

As used herein the term "oligomer inhibitor" means an inhibitor that has the ability to block primer or probe annealing to a nucleic acid sequence. The inhibitor may be a polynucleotide designed to competitively inhibit binding of primer or probe to cDNA that is similar but not identical to the target template sequence. The "oligomer inhibitor" may contain a complementary or about complementary sequence to a non-specific target sequence. A polynucleotide oligomer inhibitor may vary in size from about 3 to about 100 nucleotides, about 5 to about 50 nucleotides, about 7 to about 20 nucleotides, about 8 to about 14 nucleotides.

This disclosure provides reagents, methods, and kits for determining the presence and/or amount of a sequence encoding an IFN subtype in a biological sample. In one aspect, a highly sensitive and specific quantitative real-time PCR (RT-PCR) assay to detect sequences encoding each of the IFN subtypes and allotypic variants (such as the allotypic variant of IFN-alpha1, IFN-alpha2 or IFN-alpha4) is provided. The assay exploits two modifications of probe-based RT-PCR: molecular beacons (MB) and locked nucleic acids (LNA). In some embodiments, the target sequence of the primer/probe sets are complementary to mature coding sequence because the 3' (3-prime) untranslated regions of mRNA transcripts may have target sites for micro-RNA molecules that initiate degradation of downstream coding sequence. Primer/probe sets complementary to coding sequence avoid spurious detection of degraded mRNA and enhance the correlation between the IFN subtype mRNA that is measured by this assay and the protein that is actually expressed. The diagnostic kit can establish patterns of IFN subtype expression that may be associated with protection from, or pathogenesis of many diseases, including infections, autoimmunity and cancer. The patterns of IFN subtype expression can be used to monitor vaccine efficacy, autoimmune disease, chronic infections, or tumor therapy.

As an exemplary embodiment, the family of IFN-alpha genes include 13 genes with 12 subtypes. The resulting proteins from the genes for subtype 1 and subtype 13 have identical sequences. IFN-alpha subtypes include IFN-alpha1b, IFN-alpha1a, IFN-alpha2a, IFN-alpha2b, IFN-alpha4a, IFN-alpha4b, IFN-alpha5, IFN-alpha6, IFN-alpha7, IFN-alpha8, IFN-alpha10, IFN-alpha14, IFN-alpha16, IFN-alpha17, and IFN-alpha21. Representative nucleic acid sequences encoding the different subtypes of IFN-alpha are known and are listed in Table 2 and Table 3 in Example 1. The allelic variants have been described including 2a and 2b, and 4a and 4b. As two different nomenclatures are commonly used for IFN-alpha subtypes, Table 2 in Example 1 is provided to identify both of these naming systems as well as the naming system used herein.

As discussed above, many sequences encoding IFN subtypes, including sequences encoding IFN-alpha subtypes, share sequence identity (e.g., 75-95% sequence identity) so that it is difficult to identify primers and probes that distinguish a sequence encoding one subtype from all other subtypes especially in a sample containing RNA or DNA for more than one subtype. Primer design for IFN-alpha subtypes has also been difficult because primers designed to bind in the 3' nontranslated region of a particular sequence encoding an IFN-alpha subtype could be binding to degraded mRNA or to downstream sequence targeted by siRNA. This contributes to nonspecific primer binding.

For example, there are two different alleles encode IFN-alpha4. Thus, IFN-alpha4 subtype includes the allelic variants IFN-alpha4a and IFN-alpha4b. These allelic variants differ by only two nucleic acid changes, resulting in the mature protein comprising the amino acid changes of alanine to threonine at position 51 and glutamic acid to valine at position 114 (See Tables 3 and 4). There are also two different alleles for IFN-alpha1. IFN-alpha1 includes the allelic variants IFN-alpha1a and IFN-alpha1b. These allelic variants differ by only a single nucleotide substitution, C to T, resulting in the change of an alanine to valine in the mature protein at position 114 as shown in Tables 3 and 4. As another example, the mature protein encoded by IFN-alpha13 comprises an amino acid sequence having 100% sequence identity with the amino acid sequence of the mature protein encoded by IFN-alpha1a. The only difference in amino acid sequence between the proteins encoded by IFN-alpha13 and IFN-alpha1a is in the presumed leader sequence where IFN-alpha13 has an alanine and IFN-alpha1a has a valine. The genetic sequence for IFN-alpha13 has an additional 15 bases in the 5' untranslated region. In the 3' untranslated region, the sequence aligns perfectly except for an AAAACAA in IFN-alpha1 versus an AAA-CAAA in IFN-alpha13. Further, IFN-alpha1 has an additional 175 bases in the 3' untranslated region.

Therefore, one aspect of the invention provides forward and reverse primers, each of which uniquely hybridizes to at least one a sequence that encodes only one IFN subtype, such as a sequence that encodes only one IFN-alpha subtype, from a composition comprising a plurality of IFN subtype templates. A set of a forward primer and a reverse primer together enables specific amplification of at least one sequence encoding a singleIFN-alpha subtype of interest a composition comprising a plurality of IFN subtype templates. The primers may enable amplification of a unique sequence encoding an IFN subtype. In some embodiments, the unique sequence may be a single codon. One or both primers may hybridize to a portion of a sequence encoding an immature peptide including, for example, a portion of a leader sequence. In other embodiments, one or both primers may hybridize to a portion of a sequence encoding a mature peptide. Accordingly, the invention includes sets of primers that enable amplification of an IFN-subtype's mature polypeptide in certain embodiments, and sets of primers that enable amplification of an IFN-subtype's immature polypeptide in certain other embodiments. The forward and reverse primers may hybridize to and enable amplification of the sense and antisense unique sequences, respectively. In addition, the forward and reverse primers may hybridize to additional nucleotides on one or both sides of the unique sequence (e.g., unique codon).

In one embodiment of the invention, forward and reverse primers may recognize and enable amplification of a sequence encoding a single allelic variant of an IFN subtype, such as, without limitation, IFN-alpha1a, IFN-alpha1b, IFN-alpha2a, IFN-alpha2b, IFN-alpha4a or IFN-alpha4b. One skilled in the art will recognize that the compositions, kits and methods of the invention may be applied to any IFN subtype allelic variant, whether now known or hereafter discovered.

In one embodiment, the composition includes forward and reverse primers for multiple IFN-subtypes or various combinations of IFN-subtypes. For example, in some embodiments, the composition may provide primer sets specific for at least one IFN-subtype, at least two IFN-subtypes, at least three IFN-subtypes, at least four IFN-subtypes, at least five IFN-subtypes, at least six IFN-subtypes, at least seven IFN-subtypes, at least eight IFN-subtypes, at least nine IFN-subtypes, at least ten IFN-subtypes, at least eleven IFN-subtypes, at least twelve IFN-subtypes, at least thirteen IFN-subtypes, at least fourteen IFN-subtypes, at least fifteen IFN-subtypes, at least sixteen IFN-subtypes, at least seventeen IFN-subtypes, at least twenty IFN-subtypes, at least thirty IFN-subtypes, or more, or any integer in between. In certain embodiments, the composition includes primer sets for multiple IFN-subtypes for use in a multiplex reaction.

The primers may be specific to a sequence encoding a human IFN-subtype. In other embodiments, the primers may be specific to a sequence encoding an IFN-subtype from any species that expresses an IFN-subtype. In some embodiments, the species may be rhesus or cynmologous monkey.

In some embodiments, a primer is at least 10 nucleotides and no more than 250 nucleotides. In some embodiments, a primer includes about 10, about 11, about 12, about 13, about 14, about 15, about 16, about 17, about 18, about 19, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, about 30 nucleotides; or about 40 nucleotides, about 50 nucleotides, about 60 nucleotides, about 70 nucleotides, about 75 nucleotides, about 80 nucleotides, about 90 nucleotides, about 100 nucleotides, about 110 nucleotides, about 115 nucleotides, about 120 nucleotides, about 130 nucleotides, about 140 nucleotides, about 150 nucleotides, about 175 nucleotides, about 187 nucleotides, about 200 nucleotides, about 225 nucleotides, and about 250 nucleotides, or any integer in between.

In some embodiments in which nonspecific binding occurs, primer specificity can be enhanced by using the primers along with an oligomer inhibitor that blocks primer annealing to the errantly amplified subtype(s) coding sequences. In one embodiment, the inhibitor comprises an LNA that is incorporated into one or both of the primers. Inhibitors may be designed by inspecting the primer or probe sequences for similarities in the non-target subtypes. If similarities are identified, an LNA (locked nucleic acids) oligo may be designed to match the similarity sequence. LNAs are advantageous because they increase the binding affinity of the primer, increase $T_m$ to allow for shorter oligoucleotide probes, and "stiffen" the oligo, thereby improving base mismatch discrimination capability. The LNA oligo may be about 2 to about 50 nucleotides, about 4 to about 30 nucleotides, preferably about 8 to about 15 nucleotides, and more preferably about 8 to about 12 nucleotides.

In another aspect of the invention, a probe is provided that specifically binds to a coding sequence of only one IFN subtype. Probes of the invention may used together with primers of the invention. In some embodiments, the sequence encoding the IFN-alpha subtype for which the probe is specific is selected from the group consisting of sequences encoding IFN-alpha1b, IFN-alpha1a, IFN-alpha2a, IFN-alpha2b, IFN-alpha4a, IFN-alpha4b, IFN-alpha5, IFN-alpha6, IFN-alpha7, IFN-alpha8, IFN-alpha10, IFN-alpha14, IFN-alpha16, IFN-alpha17, and IFN-alpha21. A probe may hybridize to a portion of a sequence encoding an immature peptide including, for example, a portion of a leader sequence. In other embodiments, a probe may hybridize to a portion of a sequence encoding a mature peptide. In some embodiments, the probe comprises at least 10 bases and is no more that 250 bases. Probes can be designed using publicly available software. Criteria for probe design include, without limitation, length, GC content, $T_m$ (melting temperature).

In one embodiment of the invention, a probe may be specific for recognizing and hybridizing to a sequence encoding a single allelic variant of an IFN subtype, such as, without limitation, IFN-alpha1a, IFN-alpha1b, IFN-alpha2a, IFN-alpha2b, IFN-alpha4a or IFN-alpha4b. One skilled in the art will recognize that the compositions, kits and methods of the invention may be applied to any IFN subtype allelic variant, whether now known or hereafter discovered.

The primers may be specific to a human IFN-subtype. In other embodiments, the primers may be specific to an IFN-subtype from any species that expresses an IFN-subtype. In some embodiments, the species may be rhesus or cynmologous monkey.

In some embodiments, the probes may be designed to bind to the sense strand of the target nucleic acid encoding the IFN subtype and in other embodiments, the probe may be designed to bind to the antisense strand of the target nucleic acid of the IFN subtype. In some embodiments, there is a preference for hybridizing to the sense or antisense strand, and in other embodiments there is no preference for the sense or antisense strand of the target nucleic acid encoding the IFN subtype, and either may be used similar results.

In some embodiments, a primer or a probe may comprise a detectable label. In certain preferred embodiments, the probe comprises a detectable label. Detectable labels include, but are not limited to, a fluorophore (e.g., Texas-Red®, Fluorescein isothiocyanate, etc.) and a hapten (e.g., biotin). Other detectable labels include FAM, TAMRA, cyanine dye, SYBR green and Alexa fluor. A detectable label may be covalently attached directly to a probe oligonucleotide, e.g., located at the probe's 5' end or at the probe's 3' end. Alternatively, a detectable label may be attached to the probe via a linker or other moiety. A probe comprising a fluorophore may also further comprise a quencher. Without limitation, examples of quenchers include Black Hole Quencher™ and Iowa Black™. In some embodiments, a probe's detectable label and quencher comprise one or more molecular beacons or scorpions. In some embodiments, a probe may comprise a capture region and detection region as described, for example, for tentacle probes (Satterfield et al., Nucleic Acids Res., 2007, Vol. 35, No. 10 e76).

In some embodiments, a probe includes about 10, about 11, about 12, about 13, about 14, about 15, about 16, about 17, about 18, about 19, about 20 nucleotides, or about 25 nucleotides, about 30 nucleotides, about 40 nucleotides, about 50 nucleotides, about 60 nucleotides, about 70 nucleotides, about 75 nucleotides, about 80 nucleotides, about 90 nucleotides, about 100 nucleotides, about 110 nucleotides, about 115 nucleotides, about 120 nucleotides, about 130 nucleotides, about 140 nucleotides, about 150 nucleotides, about 175 nucleotides, about 187 nucleotides, about 200 nucleotides, about 225 nucleotides, and about 250 nucleotides or any integer in between. In certain preferred embodiments, linear (non-hairpin) probes include about 30 nucleotides, more preferably about 20 to about 25 nucleotides. In another preferred embodiment, hairpin-shaped molecular beacon probes include about 40 to about 50 nucleotides, more preferably about 25 to about 40 nucleotides.

In some embodiments, a primer and/or a probe comprises one or more residues that are LNAs. As discussed above, LNAs provide for increased stability and specificity. In some embodiments, a primer and/or a probe may comprise both one or more LNAs and one or more molecular beacons. Whether a primer and/or a probe is more sensitive and specific if it has one or more molecular beacons and/or one or more LNAs may be determined by synthesizing each primer and/or probe and testing them for the ability to detect their respective IFN-alpha subtypes.

Both primers and probes of the invention may be designed using computer implemented methods and then synthesized using commercially available synthesizer and reagents.

In some embodiments, multiple sets of primers and probes are provided. For example, primers and probes for amplifying and detecting sequences encoding two or more IFN subtypes may be provided. In one embodiment, primers and probes for amplifying and detecting sequences encoding all of the IFN-alpha subtypes, or combinations thereof, are provided.

In another aspect of the invention, primers may be used with an agent that binds to double stranded DNA (referred to herein as "DS-agent"). In some embodiments, the DS-agent is a dye In some embodiments, a probe may not need to be employed as the agent will detect the double stranded DNA and the amplification products can be separated by size. Thus, the combination of the DS-agent and a particular size amplification product can identify each IFN subtype. For example, an amplification product for IFN-alpha1b can have a size of about 107 base pairs or about 69,550 Daltons; an amplification product for IFN-alpha5 can have a size of about 113 base pairs or about 73,450 Daltons; an amplification product for IFN-alpha10 can have a size of about 89 base pairs or about 57,850 Daltons; an amplification product of IFN-alpha 16 can have a size of about 79 base pairs or about 51,350 Daltons; and an amplification product of IFN-alpha21 can have a size of about 125 base pairs or about 81,250 Daltons. DS-agents including SYBR green may also be used in quantitative PCR assays as a substitute for a detection probe and the linear amplification is determined by activation of the dye following binding to the dsDNA amplification target.

Exemplary embodiments of sequences for primers, probes and inhibitors for IFN-alpha subtypes are shown in FIG. 1, below. For example, forward and reverse primer pairs may be selected from the groups consisting of SEQ ID NOS: 30-43 and SEQ ID NOS: 45-58. Probes may be selected from the group consisting of SEQ ID NOS: 59-72. An inhibitor may be selected from the group consisting of SEQ ID NO: 44, SEQ ID NO: 88 and SEQ ID NO: 89. For example, for IFN-alpha5 the primers may comprise forward primer SEQ ID NO: 35 and reverse primer SEQ ID NO: 50 and the probe may comprise SEQ ID NO: 64. As another example, for IFN-alpha21 the primers may comprise forward SEQ ID NO: 43 and SEQ ID NO: 58 and the probe may comprise SEQ ID NO: 72. Again, for IFN-alpha4a/b the primers may comprise forward primer SEQ ID NO: 32 and reverse primer SEQ ID NO: 47, the probe may comprise SEQ ID NO: 61, and the inhibitor may comprise SEQ ID NO: 44.

In one aspect of the invention, various parameters of the primers and/or probes may be adjusted to enhance the operation of the primers and/or probes in the specific amplification and detection of sequences encoding the IFN subtypes. For example, the ratio of primer to probe concentration may be optimized to enhance signal, especially in samples with multiple IFN subtypes. In one embodiment, three criteria may be used to determine primer/probe set quality: sensitivity, efficiency and specificity.

Sensitivity refers simply to the fewest number of molecules of the target that can be detected. Sensitivity may be determined by techniques well known in the art, e.g., any technique which compared test reactions to standard reactions using a standard curve.

Efficiency refers to the actual ratio of product to template for each cycle of PCR. An efficiency of 2.0 is perfect. The difference between an efficiency of 1.95 vs. 2.00 at 30 cycles, with one copy at the start of reaction, is $5 \times 10^8$ copies vs. $1.07 \times 10^9$ copies, i.e. a sensitivity that is 50% of ideal. In some embodiments, an acceptable efficiency is at least about 1.85. In some embodiments, an acceptable efficiency is at least about 1.9, at least about 1.95, at least about 1.98, about 2.0, or any efficiency in between. Table 1, below, shows exemplary efficiencies at 20 and 40 cycles, assuming a reaction with 1 starting copy of the nucleotide sequence (template) of interest.

TABLE 1

| Efficiency | # copies | |
| --- | --- | --- |
| | 20 cycles | 40 cycles |
| 2.00 | $1.05 \times 10^6$ | $1.09 \times 10^{12}$ |
| 1.95 | $6.32 \times 10^5$ (60%) | $3.99 \times 10^{11}$ (37%) |
| 1.90 | $3.76 \times 10^5$ (36%) | $1.41 \times 10^{11}$ (13%) |

Specificity is the detection by only the sequence of interest, and not any of the other similar sequences. In some embodiments, an acceptable specificity is at least 9 cycles difference between primers amplifying specific and nonspecific template, or 512-fold difference. In other embodiments, an acceptable specificity is at least 8 cycles difference, at least 7 cycles difference, at least 6 cycles difference or at least 5 cycles difference between specific and nonspecific template. Specificity measurements may vary depending on the concentration of each IFN-subtype in a sample. For example, specificity for a particular primer set may increase or decrease if concentrations of IFN-subtypes in a sample are not equivalent (for example, in clinical settings).

In some embodiments, sensitivity and specificity can be altered depending on the temperature of the reverse transcriptase reaction or primer/probe $T_m$. In general, the temperature is raised to increase specificity or lowered to increase sensitivity. In addition, salt concentrations may be raised or lowered to optimize binding, and detection volumes may be decreased and filter sets optimized to increase sensitivity.

A balance between sensitivity and specificity is desirable. In some embodiments, this balance is achieved by conducting the reverse transcriptase reaction at a temperature of about 45° C. to about 60° C., more preferably about 50° C. In other embodiments, the balance is also achieved by selecting primers that have a primer extension temperature of at least 50° C. to 60° C., more preferably 55° C. to 60° C., and most preferably 58° C. to 60° C. In other embodiments, the balance is also achieved by using different concentration of primers and probes. In some embodiments, primer concentrations range from about 50 to 1000 nM, more preferably 100 to 500 nM. In some embodiments, probe concentrations range from 35 to 500 nM, more preferably from 50 to 250 nM.

In another aspect of the invention, an assay kit for detecting sequences encoding IFN subtypes is provided. In some embodiments, the kit provides a forward and a reverse primer that together enable amplification of at least one sequence encoding an IFN subtype from a composition comprising a plurality of IFN subtype templates. In some embodiments, the IFN subtype is an IFN-alpha subtype selected from the group consisting of IFN-alpha1b, IFN-alpha1a, IFN-alpha2a, IFN-alpha2b, IFN-alpha4a, IFN-alpha4b, IFN-alpha5, IFN-alpha6, IFN-alpha7, IFN-alpha8, IFN-alpha10, IFN-alpha14, IFN-alpha16, IFN-alpha17 and IFN-alpha21. In other embodiments, the assay kit may provide forward and reverse primers for each of these IFN-alpha subtypes.

In yet other embodiments, the assay kit may provide multiple primer sets specific for various combinations of IFN subtypes. For example, in some embodiments, the assay kit may provide primer sets specific for at least one IFN-subtype, at least two IFN-subtypes, at least three IFN-subtypes, at least four IFN-subtypes, at least five IFN-subtypes, at least six IFN-subtypes, at least seven IFN-subtypes, at least eight IFN-subtypes, at least nine IFN-subtypes, at least ten IFN-subtypes, at least eleven IFN-subtypes, at least twelve IFN-subtypes, at least thirteen IFN-subtypes, at least fourteen IFN-subtypes, at least fifteen IFN-subtypes, at least sixteen IFN-subtypes, at least seventeen IFN-subtypes, at least twenty IFN-subtypes, at least thirty IFN-subtypes, or more, or any integer in between. In one embodiment, the assay kit may provide primers specific for a sequence encoding a single allelic variant of an IFN subtype, such as, without limitation, IFN-alpha1a, IFN-alpha1b, IFN-alpha2a, IFN-alpha2b, IFN-alpha4a or IFN-alpha4b. One skilled in the art will recognize that the compositions, kits and methods of the invention may be applied to any IFN subtype allelic variant, whether now known or hereafter discovered.

In yet another embodiment, the assay kit includes primer sets for multiple IFN-subtypes for use in a multiplex reaction. Such a kit may allow specific amplification of more than one IFN-subtype in a single reaction vessel. In some embodiments, amplification products of different IFN-subtypes may be identified with different dyes or labels, or probes or DS agents labeled with different dyes.

In certain preferred embodiments, the assay kit with amplification reaction reagents (i.e., forward and reverse primers) for combinations of IFN subtypes or all IFN subtypes, uses the same reactions conditions for all IFN subtypes amplifications while maintaining sensitivity, specificity and efficiency. In certain preferred embodiments, a kit may comprise amplification reaction reagents that perform well under the same reaction conditions for all IFN-alpha subtypes.

Combinations of different sets of primers may be designed based on the detection, diagnosis, or treatment for a particular disease type. An assay kit comprising such sets of primers may be used to detect a disease or disorder in a subject having cancer, a viral infection, or an autoimmune disease, for example. An assay kit may also be used to detect a disease or disorder in a tissue sample, cell sample, bodily fluid, urine, blood, serum, plasma, leukocytes, monocytes, peripheral blood leukocytes (PBL), lymph, saliva, cerebrospinal fluid (CSF), synovial fluid, bronchoalveolar lavage (BAL), pericardial fluid, spinal fluid, pleural fluid, pleural effusion, mucus, breast milk, amniotic fluid, vaginal fluid, semen, prostatic fluid, ascites, ascitic fluid, peritoneal fluid, aqueous humor, vitreous humor, tears, rheum, perspiration, cystic fluid, gastric acid and tumor tissue sample, for example.

In some embodiments, assay kits may further comprise one or more inhibitors, probes and/or DS-agents corresponding to the IFN subtype primers provided with the kit.

In some embodiments, the assay kit may comprises one or more controls. Controls can include dilution of a known amount of each of the IFN subtypes. In other embodiments, a negative control may comprise a primer/probe without its corresponding IFN subtype template sequence, cDNA from a cell from a species that does not express IFNs or that expresses IFNs with sequences that are significantly different from any template sequences, salmon sperm DNA, etc. In other embodiments, a positive control may comprise cDNA from human cells that are over-stimulated to produce the IFN subtype of interest, or multiple or all IFN subtypes.

In some embodiments, the assay kit may comprise one or more reagents for generating standard curves using cDNA for each IFN subtype for quantification of the number of copies of an IFN subtype generated through the PCR reaction. This type of standard curve allows the number of molecules generated to be quantified. In other embodiments, the assay kit may include a spreadsheet template or the like for automatic calculation of standard curves and concentrations of cDNA template and housekeeping gene (HKG), if used.

In some embodiments, each set or combination of forward or reverse primers is packaged in a container. The containers may include a variety of shapes materials and configurations. For example, a multiwell plate may be utilized, or a number of spin tubes. In other embodiments, a cartridge with multiple wells or a microfluidics device, such as a lab on a chip, may be employed. Other containers with multiple wells or reaction areas are know to those of skill in the art and can be readily employed with the invention as described herein.

In some embodiments, the assay kit further includes instructions for implementing a method for detecting sequence(s) encoding one or more subtypes in a sample. Exemplary steps of the method are described below. The instructions may further include a description of isolation and purification of nucleic acids from the sample. The kit may further include instructions for quantitating the amount of a subtype in the sample using a standard curve.

In one embodiment, a kit is provided that allows for comprehensive, sensitive and specific analysis of all thirteen subtypes of IFN-alpha. There are many potential applications for this assay kit (as well as similar kits for other IFN subtypes), which include defining pathogenic or protective roles for specific subtypes in infectious and autoimmune diseases and in cancer immunity. Most importantly, potential clinical applications for this kit include its use as a surrogate marker for vaccine efficacy in clinical trials, to monitor clinical progression or remission of chronic infections, autoimmune diseases or cancer, or to determine response to therapy for those diseases. The kit may also define which patients with any of those diseases may be refractory to therapeutic measures taken to ameliorate them.

Accordingly, in another aspect of the invention, a method of detecting sequence(s) encoding one or more IFN subtype(s) is provided. The method may use the primers or kits disclosed herein. In one embodiment, the method comprises contacting a sample containing IFN subtype(s) DNA or RNA with a set of forward and reverse primers under conditions suitable for amplification and detecting the amplification product. The presence of the amplification product indicates that the sample contained a sequence encoding the IFN subtype(s) of interest.

The methods and assay kits of this invention may be used to detect a sequence encoding any IFN subtypes such as, for example, IFN-alpha or IFN-lambda2 or -lambda3. In certain preferred embodiments, the methods are used to detect a selection of the IFN-alpha subtypes. In other embodiments, a combination of subtypes may be detected from various IFNs, such as IFN-alpha, IFN-lambda (i.e., IFN-lambda2 and -lambda3) and combinations thereof. Nucleic acid sequences for many of the IFN subtypes are known, such as IFN-beta (accession number: NM_002176.2), IFN-gamma (accession number: NM_000619.2), IFN-lambda1 (IL-29 (accession number: BC074985), IFN-lambda2 (IL-28A accession number: NM_172138.1), and IFN-lambda3 (IL-28B accession number: NM_172139.2). See, for example, Donnelly et al., J. Leukoc. Biol. 76:314-321 (2004) and Pestka et al., Immunol. Rev. 202: 8-32 (2004).

Any type of amplification reaction may be used including PCR, RT-PCR, allele-specific PCR, nested PCR, cell cloning, or any other type of amplification known to a skilled artisan. In some embodiments, such as when the sample comprises RNA, the RT-PCR comprises two steps: a reverse transcription (RT) reaction and an amplification reaction (PCR). In other embodiments, such as when the sample contains DNA, only the amplification step (PCR) is required. In some embodiments the number of amplification cycles is at least 10 cycles, at least 15 cycles, at least 20 cycles, at least 25 cycles, at least 30 cycles, at least 35 cycles, at least 40 cycles, at least 45 cycles, or any integer in between.

Methods of the invention may optionally also comprise contacting the sample or the amplification product with a probe corresponding to the IFN subtype of interest and/or a DS-agent to identify the presence of the IFN subtype of interest. In some embodiments, detection of the amplification products depends on the type of detectable label employed and whether a probe is employed. If a probe is employed, detecting may be based on the molecular beacon technology or the binding of affinity based molecule such as biotin or an aptamer. Dyes such as fluorescent dyes may also be detected using standard optical methods. In other embodiments, the amplification products may be separated on a gel and different size products detected.

The amount of an IFN subtype expressed in a sample can be determined using standard curves with known amounts of IFN subtypes. Densitometry tracing of gels may also be used. In some embodiments, the amount of IFN subtype may also be determined using a standard house keeping gene (HKG) common to the sample being tested. In a certain preferred embodiment, IFN subtype expression may be quantified as a function of a cDNA template's standard curve. This "absolute concentration" yields a more meaningful interpretation of quantity of IFN-alpha subtypes because it allows the actual number of molecules of the template of interest to be determined, rather than showing relative amounts.

In some embodiments, robotics is used to increase precision in using the assay kit. Those skilled in the art are familiar with robotics, such as liquid handlers, that dispense reagents automatically, thus reducing the possibility of human error. In one embodiment, such methods also allow reduction in overall reaction volume to, for example, as little as 5 ul without significant loss in sensitivity.

In one embodiment, the method may be useful for diagnosing a condition or detecting a condition or susceptibility to a condition in a subject. The condition may include, for example, cancer, viral infections, inflammation and autoimmune conditions. Viral infections include Hepatitis A, B, and C, Ebola, Dengue, HIV, HPV, Herpes, and the like. Autoimmune conditions include systemic lupus erythematosus (SLE), rheumatoid arthritis, Sjogrens, psoriasis, multiple sclerosis, and the like. Inflammatory conditions include irritable bowel conditions such as ulcerative colitis, and Crohn's disease having cancer, a viral infection, or an autoimmune disease. These methods may additionally include generating a gene expression profile of IFN subtypes for the sample and comparing the gene expression profile of the sample to one or more known gene expression profiles of IFN subtypes associated with a disease. The sample expression profile may be correlated to the known expression profile to indicate the presence of the disease in the sample.

In a related embodiment, the method may be useful for identifying regions of diseased tissue or diseased cells by their IFN subtype expression patterns. In such embodiments, the method may be performed with multiple samples comprising different regions of cells or tissue such that the expression patterns from each sample may be compared and diseased regions identified. This would be helpful for treating conditions that are not systemic, and instead effect specific areas of tissue. Examples of such conditions are cutaneous lupus and dermatomyositis, which effect regions of the epithelium and muscle tissue, respectively. In some embodiments, the method may be used to determine the site of pathogen infection in tissue or cells. A pathogen may elevate the expression levels of IFN subtypes in the affected area, or, in some conditions, a pathogen may block IFN expression.

In another embodiment, the method may be useful for detecting or verifying the presence of a condition in which local IFN subtype expression patterns play a role in phenotype.

In another embodiment, the method may be useful for monitoring the efficacy of a therapy for a condition characterized by a gene expression profile of different IFN subtypes. A more specific embodiment provides a method for evaluating the efficacy of an immunomodulatory drug. Efficacy may be evaluated by correlation to known IFN expression patterns at different stages of disease progression or therapy. Thus, a standard therapeutic index may be generated and sample results may be correlated to the index to monitor or evaluate drug or therapy efficacy. Diseases that may be used with these methods include, for example, cancer, viral infections, inflammation, and autoimmune conditions. Viral infections include Hepatitis A, B, and C, Ebola, Dengue, HIV, HPV, Herpes, and the like. Autoimmune conditions include SLE, rheumatoid arthritis, Sjogrens, psoriasis, multiple sclerosis, and the like. Inflammatory conditions include irritable bowel conditions such as ulcerative colitis and Crohn's disease, for example. In one embodiment, samples may be taken from the patient periodically during treatment to determine whether the IFN subtype profile changes during the course of therapy.

In another embodiment, the method may be useful for monitoring efficacy of a vaccine, in particular, vaccines for viral infections. Viral infections include Hepatitis A, B, and C, Ebola, Dengue, HIV, HPV, Herpes, and the like. Samples may be taken from the patient periodically after vaccination to determine whether the IFN subtype profile changes during the course of developing an immune response.

Samples from the subject can include, for example, tissue sample, cell sample, bodily fluid, urine, blood, serum, plasma, leukocytes, monocytes, peripheral blood leukocytes (PBL), lymph, saliva, cerebrospinal fluid (CSF), synovial fluid, bronchoalveolar lavage (BAL), pericardial fluid, spinal fluid, pleural fluid, pleural effusion, mucus, breast milk, amniotic fluid, vaginal fluid, semen, prostatic fluid, ascites, ascitic fluid, peritoneal fluid, aqueous humor, vitreous humor, tears, rheum, perspiration, cystic fluid, gastric acid, and tumor tissue sample. In some embodiments, the samples may be processed prior to contacting them with primers of the invention in order to extract and purify nucleic acids for amplification using standard methods.

In another aspect of the invention, a method for designing primers for IFN subtypes is provided. Using IFN-alpha subtype primer design as an exemplary embodiment, first coding sequences of each of the IFN-alpha subtypes may be aligned determine which portions of each subtype's sequence are unique to that subtypes and not found in any of the other subtypes. While computer software may be used to aid in identifying the IFN subtypes' unique sequences and generating potential primer pairs, it cannot predict whether a primer pair will actually function experimentally. In particular, in silico primer design cannot select appropriate primer sensitivity and specificity. Accordingly, an embodiment of the invention includes experimentally verifying that primer sets are functional. A further embodiment includes optimizing primer sets through experimentation. Neither of these steps may be accurately performed in silico.

In one embodiment, potential primer pairs may be first tested for sensitivity to small amounts of sequences encoding the target IFN subtype (IFN subtype of interest). In certain preferred embodiments, primer pairs that have a sensitivity sufficient to detect at least about 1-10 copies of reverse transcribed cDNA of the IFN subtype of interest per reaction are selected for further testing.

Primer pairs with satisfactory sensitivity may then be tested for specificity to the specific target IFN subtype sequence (as opposed to other IFN subtypes with similar sequences). In some embodiments, the primer sequences may be shifted 5' or 3' with respect to the unique sequence to enhance specificity. In other embodiments, a LNA probe may be used to enhance specificity to the target IFN subtype sequence. LNA probes may be designed to selectively block the competing IFN subtype cDNA. Incorporation of this blocking LNA oligo into the reaction mix for a specific IFN subtype will result in selective binding of the LNA to the undesired cDNA, thus effectively blocking its ability to be amplified by the primer pair while allowing the desired specificity for the IFN subtype of interest. In some embodiments, primer pairs with a specificity of at least 5, at least 6, at least 7 or at least 8 cycles difference between amplification of specific and nonspecific template are selected for further testing. In certain preferred embodiments, primer pairs with a specificity of at least about 9 amplification cycles or more difference between specific and nonspecific amplification, which corresponds to about a 500-fold difference between on-target and off-target template being amplified, are selected for further testing. In some embodiments, secondary experiments may be performed to optimize the selected primer pairs' sensitivity and specificity profiles. at least 9 cycles difference between primers amplifying specific and nonspecific template Next, primer pairs with satisfactory sensitivity and specificity may then be tested for efficiency. In certain preferred embodiments, primer pairs with an efficiency of at least about 1.90, more preferably at least about 1.95, are selected. In one embodiment, primer pair efficiency may be tested by testing the originally selected primer pairs as well as those primer pairs modified to contain molecular beacon(s) and/or LNA(s) in a side by side comparison. Such experiments may include extensive titration of target IFN subtype sequences, oligos and reaction components to optimize the sensitivity of the primer pairs to the target subtype, while simultaneously creating the largest separation (i.e., Ct values) from the other subtypes to result in optimal specificity.

In other embodiments, further primer design includes optimizing for criteria such as melting temperature, GC content, and length. Primers may incorporate modified bases that provide for enhanced stability and duplex formation. In some embodiments, primers are designed and selected that have a primer extension temperature in the range of 50° C. to 60° C., more preferably 55° C. to 60° C., and most preferably 58° C. to 60° C. One skilled in the art will recognize that various modifications may be made to the primers, such as adding various moieties or shifting, lengthening or shortening the length of IFN-subtype to which a primer hybridizes, while keeping within the scope and spirit of the invention.

In certain preferred embodiments, primer pairs may be further tested and optimized to obtain primer pairs for sequences encoding each IFN subtype that retain their desirable characteristics under the same PCR reaction conditions. Selecting primers that perform well consistently under the same reaction conditions allows a panel of primers for amplification of sequences encoding various IFN subtypes to be used simultaneously in an IFN subtype panel assay, such as a panel assay comprising all of the IFN-alpha subtypes. In certain preferred embodiments, the PCR reaction conditions may be: Stage 1: 50° C. for two minutes; Stage 2: 95° C. for three minutes; Stage 3: 40 repeats of 95° C. for 15 seconds followed by 59° C. for one minute.

In another aspect of the invention, the principals employed for designing primers, probes, assay kits, and methods of their use may be applied to other biological molecules for which different, highly related subtypes occur in the body. One skilled in the art would understand that such molecules may include, without limitation, allelic variants (such as MHC class I and II variants) or viral strains with high sequence identity.

EXAMPLES

Example 1

Designing and Testing Primers for IFN-Subtypes

IFN-Alpha Sequences.

Sequences of the IFN-alpha genotypes and the two allotypic variants were obtained from the website of the National Center for Biotechnology Information (NCBI) Entrez Nucleotide database (ncbi.nlm.nih.gov/sites). As explained above, there are two sets of nomenclature for the IFN-alpha genotypes, neither of which is systematic or intuitive. Table 2 shows accession and GI numbers for the DNA and immature proteins with the nomenclature for the IFN-alpha genotype. Table 2 further shows the two sets of nomenclature that are commonly used ("Name 1" and "Name 2"), and the set that is used herein ("Name 3"), along with accession numbers of the genotypes.

TABLE 2

| Accession # | GI # | Name 1 | Name 2 | Name 3 * |
|---|---|---|---|---|
| V00538 | 32713 | αD | α1 | α1b |
| J00210 | 184593 | α1 | αD | α1a |

TABLE 2-continued

| Accession # | GI # | Name 1 | Name 2 | Name 3 * |
|---|---|---|---|---|
| V00549 | 32744 | αA | α2a | α2a |
| V00548 | 32740 | α2 | α2b | α2b |
| NM_021068 | 209413721 | α4a | αM1 | α4a |
| X02955 | 32656 | α4b | α4 | α4b |
| X02956 | 32659 | αG | α5 | α5 |
| X02958 | 32662 | αK | α6 | α6 |
| X02960 | 32665 | αJ1 | α7 | α7 |
| X03125 | 32668 | αB2 | α8 | α8 |
| X02961 | 32710 | αC | α10 | α10 |
| X02959 | 32650 | αH2 | α14 | α14 |
| X02957 | 32653 | αWA | α16 | α16 |
| V00532 | 32633 | αI | α17 | α17 |
| V00540 | 32716 | α4F | α21 | α21 |

* nomenclature used herein

Table 3 depicts the sequence alignment and nucleotide sequence for IFN-alpha subtypes. As shown in the table, gene coding sequences for mature IFN-alpha subtype proteins were aligned by codon with identifiers for sequence homology: regular font for consensus; small capital letters for unique non-consensus codons; bold and underlined for shared non-consensus codons; and bold and italicized for groups of codons unique to one subtype. In addition, bold nucleotides were identified for potential forward primers specific to multiple IFN alpha subtypes, and italicized nucleotides were identified for potential probes to multiple IFN alpha subtypes. In Table 4, the mature protein sequences are presented for the Gene coding sequences of Table 3.

TABLE 3

| SEQ ID NO: | Codon Position | 1 / 1 | 2 / 4 | 3 / 7 | 4 / 10 | 5 / 13 | 6 / 16 | 7 / 19 | 8 / 22 | 9 / 25 | 10 / 28 |
|---|---|---|---|---|---|---|---|---|---|---|---|
| 73 | Consensus | tgt | gat | ctg | cct | cag | acc | cac | agc | ctg | ggt |
| 1 | IFN-α1b | tgt | gat | ctc | cct | gag | acc | cac | agc | ctg | gat |
| 2 | IFN-α1a | tgt | gat | ctc | cct | gag | acc | cac | agc | ctg | gat |
| 3 | IFN-α2A | tgt | gat | ctg | *cct* | *caa* | *acc* | cac | agc | ctg | ggt |
| 4 | IFN-α3b | tgt | gat | ctg | *cct* | *caa* | *acc* | cac | agc | ctg | ggt |
| 5 | IFN-α4a | tgt | gat | ctg | cct | cag | acc | cac | agc | ctg | ggt |
| 6 | IFN-α4b | tgt | gat | ctg | cct | cag | acc | cac | agc | ctg | ggt |
| 7 | IFN-α5 | tgt | gat | ctg | cct | cag | acc | cac | agc | ctg | AGT |
| 8 | IFN-α6 | tgt | gat | ctg | cct | cag | acc | cac | agc | ctg | ggt |
| 9 | IFN-α7 | tgt | gat | ctg | cct | cag | acc | cac | agc | ctg | CGT |
| 10 | IFN-α8 | tgt | gat | ctg | cct | cag | act | cac | agc | ctg | ggt |
| 11 | IFN-α10 | tgt | gat | ctg | cct | cag | acc | cac | agc | CTC | ggt |
| 12 | IFN-α14 | tgt | AAT | ctg | TCT | caa | acc | cac | agc | ctg | AAT |
| 13 | IFN-α16 | tgt | gat | ctg | cct | cag | act | cac | agc | ctg | ggt |
| 14 | IFN-α17 | tgt | gat | ctg | cct | cag | acc | cac | agc | ctg | ggt |
| 15 | IFN-α21 | tgt | gat | ctg | cct | cag | acc | cac | agc | ctg | ggt |

| SEQ ID NO: | Codon Position | 11 / 31 | 12 / 34 | 13 / 37 | 14 / 40 | 15 / 43 | 16 / 46 | 17 / 49 | 18 / 51 | 19 / 55 | 20 / 58 |
|---|---|---|---|---|---|---|---|---|---|---|---|
| 73 | Concensus | aat | agg | agg | gcc | ttg | ata | ctc | ctg | gca | caa |
| 1 | IFN-α1b | aac | agg | agg | acc | ttg | atg | ctc | ctg | gca | caa |
| 2 | IFN-α1a | aac | agg | agg | acc | ttg | atg | ctc | ctg | gca | caa |
| 3 | IFN-α2A | agc | agg | agg | acc | ttg | atg | ctc | ctg | gca | *cag* |
| 4 | IFN-α2b | agc | agg | agg | acc | ttg | atg | ctc | ctg | gca | *cag* |
| 5 | IFN-α4a | aat | agg | agg | gcc | ttg | ata | ctc | ctg | gca | caa |
| 6 | IFN-α4b | aat | agg | agg | gcc | ttg | ata | ctc | ctg | gca | caa |
| 7 | IFN-α5 | aac | agg | agg | act | ttg | atg | ATA | atg | gca | caa |
| 8 | IFN-α6 | CAC | agg | agg | acc | ATG | atg | ctc | ctg | gca | caa |
| 9 | IFN-α7 | aat | agg | agg | gcc | ttg | ata | ctc | ctg | gca | caa |
| 10 | IFN-α8 | aac | agg | agg | gcc | ttg | ata | ctc | ctg | gca | caa |
| 11 | IFN-α10 | aat | agg | agg | gcc | ttg | ata | ctc | GGA | gca | caa |
| 12 | IFN-α14 | aac | agg | agg | act | ttg | atg | ctc | atg | gca | caa |
| 13 | IFN-α16 | aat | agg | agg | gcc | ttg | ata | ctc | ctg | gca | caa |
| 14 | IFN-α17 | aat | agg | agg | gcc | ttg | ata | ctc | ctg | gca | caa |
| 15 | IFN-α21 | aat | agg | agg | gcc | ttg | ata | ctc | ctg | gca | caa |

TABLE 3-continued

| SEQ ID NO: | | Codon<br>Position | 21<br>61 | 22<br>64 | 23<br>67 | 24<br>70 | 25<br>73 | 26<br>76 | 27<br>79 | 28<br>82 | 29<br>85 | 30<br>88 |
|---|---|---|---|---|---|---|---|---|---|---|---|---|
| 73 | Consensus | | atg | gga | aga | atc | tct | cct | ttc | tcc | tgc | ctg |
| 1 | IFN-α1b | | atg | agc | aga | atc | tct | cct | *tcc* | *tcc* | *tgt* | ctg |
| 2 | IFN-α1a | | atg | agc | aga | atc | tct | cct | *tcc* | *tcc* | *tgt* | ctg |
| 3 | IFN-α2A | | *atg* | *agg* | AAA | atc | tct | ctt | ttc | tcc | tgc | ttg |
| 4 | IFN-α2b | | *atg* | *agg* | *aga* | atc | tct | ctt | ttc | tcc | tgc | ttg |
| 5 | IFN-α4a | | atg | gga | aga | atc | tct | cat | ttc | tcc | tgc | ctg |
| 6 | IFN-α4b | | atg | gga | aga | atc | tct | cat | ttc | tcc | tgc | ctg |
| 7 | IFN-α5 | | atg | gga | aga | atc | tct | cct | ttc | tcc | tgc | ctg |
| 8 | IFN-α6 | | atg | agg | aga | atc | tct | ctt | ttc | tcc | tgt | ctg |
| 9 | IFN-α7 | | atg | gga | aga | atc | tct | cct | ttc | tcc | tgc | ttg |
| 10 | IFN-α8 | | atg | CGA | aga | atc | tct | cct | ttc | tcc | tgc | ctg |
| 11 | IFN-α10 | | atg | gga | aga | atc | tct | cct | ttc | tcc | tgc | ctg |
| 12 | IFN-α14 | | atg | agg | aga | atc | tct | cct | ttc | tcc | tgc | ctg |
| 13 | IFN-α16 | | atg | gga | aga | atc | tct | cat | ttc | tcc | tgc | ctg |
| 14 | IFN-α17 | | atg | gga | aga | atc | tct | cct | ttc | tcc | tgc | ctg |
| 15 | IFN-α21 | | atg | gga | aga | atc | tct | cct | ttc | tcc | tgc | ctg |

| SEQ ID NO: | | Codon<br>Position | 31<br>91 | 32<br>94 | 33<br>97 | 34<br>100 | 35<br>103 | 36<br>106 | 37<br>109 | 38<br>112 | 39<br>115 | 40<br>118 |
|---|---|---|---|---|---|---|---|---|---|---|---|---|
| 73 | Consensus | | aag | gac | aga | cat | gac | ttt | gga | ttc | ccc | cag |
| 1 | IFN-α1b | | atg | gac | aga | cat | gac | ttt | gga | ttt | ccc | cag |
| 2 | IFN-α1a | | atg | gac | aga | cat | gac | ttt | gga | ttt | ccc | cag |
| 3 | IFN-α2A | | aag | gac | aga | cat | gac | ttt | gga | ttt | ccc | cag |
| 4 | IFN-α2b | | aag | gac | aga | cat | gat | ttc | gga | ttt | ccc | gag |
| 5 | IFN-α4a | | aag | gac | aga | *cat* | *gat* | *ttc* | *gga* | *ttc* | *ccc* | *gag* |
| 6 | IFN-α4b | | aag | gac | aga | *cat* | *gat* | *ttc* | *gga* | *ttc* | *ccc* | *gag* |
| 7 | IFN-α5 | | aag | gac | aga | cat | gac | ttt | gga | ttt | CCT | cag |
| 8 | IFN-α6 | | aag | gac | aga | cat | gac | ttc | aga | ttt | ccc | cag |
| 9 | IFN-α7 | | aag | gac | aga | cat | GAA | ttc | aga | ttc | CCA | gag |
| 10 | IFN-α8 | | aag | gac | aga | cat | gac | ttt | gaa | ttc | ccc | cag |
| 11 | IFN-α10 | | aag | gac | aga | cat | gat | ttc | CGA | ATC | ccc | cag |
| 12 | IFN-α14 | | aag | gac | aga | cat | gac | ttt | gaa | ttt | ccc | cag |
| 13 | IFN-α16 | | aag | gac | aga | TAT | gat | ttc | gga | ttc | ccc | cag |
| 14 | IFN-α17 | | aag | gac | aga | CCT | gac | ttt | gga | CTT | ccc | cag |
| 15 | IFN-α21 | | aag | gac | aga | cat | gac | ttt | gga | ttc | ccc | CAA |

| SEQ ID NO: | | Codon<br>Position | 41<br>121 | 42<br>124 | 43<br>127 | 44<br>130 | 45<br>133 | 46<br>136 | 47<br>139 | 48<br>142 | 49<br>145 | 50<br>148 |
|---|---|---|---|---|---|---|---|---|---|---|---|---|
| 73 | Consensus | | gag | gag | ttt | gat | ggc | aac | cag | ttc | cag | aag |
| 1 | IFN-α1b | | gag | gag | ttt | gat | ggc | aac | cag | ttc | cag | aag |
| 2 | IFN-α1a | | gag | gag | ttt | gat | ggc | aac | cag | ttc | cag | aag |
| 3 | IFN-α2A | | gag | gag | ttt | | ggc | aac | cag | ttc | caa | aag |
| 4 | IFN-α2b | | gag | gag | ttt | | ggc | aac | cag | ttc | caa | aag |
| 5 | IFN-α4a | | *gag* | gag | ttt | gat | ggc | cac | cag | ttc | cag | aag |
| 6 | IFN-α4b | | *gag* | gag | ttt | gat | ggc | cac | cag | ttc | cag | aag |
| 7 | IFN-α5 | | gag | gag | ttt | gat | ggc | aac | cag | ttc | cag | aag |
| 8 | IFN-α6 | | gag | gag | ttt | gat | ggc | aac | cag | ttc | cag | aag |
| 9 | IFN-α7 | | gag | gag | ttt | gat | ggc | cac | cag | ttc | cag | aag |
| 10 | IFN-α8 | | gag | gag | ttt | gat | GAT | AAA | cag | ttc | cag | aag |
| 11 | IFN-α10 | | gag | gag | ttt | gat | ggc | aac | cag | ttc | cag | aag |
| 12 | IFN-α14 | | gag | GAA | ttt | gat | ggc | aac | cag | ttc | cag | AAA |
| 13 | IFN-α16 | | gag | GTG | ttt | gat | ggc | aac | cag | ttc | cag | aag |
| 14 | IFN-α17 | | gag | gag | ttt | gat | ggc | aac | cag | ttc | cag | aag |
| 15 | IFN-α21 | | gag | gag | ttt | gat | ggc | aac | cag | ttc | cag | aag |

| SEQ ID NO: | | Codon<br>Position | 51<br>151 | 52<br>154 | 53<br>157 | 54<br>160 | 55<br>163 | 56<br>166 | 57<br>169 | 58<br>172 | 59<br>175 | 60<br>178 |
|---|---|---|---|---|---|---|---|---|---|---|---|---|
| 73 | Consensus | | gct | caa | gcc | atc | tct | gtc | ctc | cat | gag | atg |
| 1 | IFN-α1b | | gct | cca | gcc | atc | tct | gtc | ctc | cat | gag | ctg |
| 2 | IFN-α1a | | gct | cca | gcc | atc | tct | gtc | ctc | cat | gag | ctg |
| 3 | IFN-α2A | | gct | gaa | acc | atc | cct | gtc | ctc | cat | gag | atg |
| 4 | IFN-α2b | | gct | gaa | acc | atc | cct | gtc | ctc | cat | gag | atg |
| 5 | IFN-α4a | | gct | caa | gcc | atc | tct | gtc | ctc | cat | gag | atg |
| 6 | IFN-α4b | | act | caa | gcc | atc | tct | gtc | ctc | cat | gag | atg |
| 7 | IFN-α5 | | gct | caa | gcc | atc | tct | gtc | ctc | cat | gag | atg |
| 8 | IFN-α6 | | gct | gaa | gcc | atc | tct | gtc | ctc | cat | gag | GTG |
| 9 | IFN-α7 | | act | caa | gcc | atc | tct | gtc | ctc | cat | gag | atg |
| 10 | IFN-α8 | | gct | caa | gcc | atc | tct | gtc | ctc | cat | gag | atg |
| 11 | IFN-α10 | | gct | caa | gcc | atc | tct | gtc | ctc | cat | gag | atg |
| 12 | IFN-α14 | | gct | caa | gcc | atc | tct | gtc | ctc | cat | gag | atg |

TABLE 3-continued

| SEQ ID NO: | | Codon<br>Position | 51<br>? | 52<br>? | 53<br>? | 54<br>? | 55<br>? | 56<br>? | 57<br>? | 58<br>? | 59<br>? | 60<br>? |
|---|---|---|---|---|---|---|---|---|---|---|---|---|
| 13 | IFN-α16 | | gct | caa | gcc | atc | tct | GCC | TTC | cat | gag | atg |
| 14 | IFN-α17 | | act | caa | gcc | atc | tct | gtc | ctc | cat | gag | atg |
| 15 | IFN-α21 | | gct | caa | gcc | atc | tct | gtc | ctc | cat | gag | atg |

| SEQ ID NO: | | Codon<br>Position | 61<br>181 | 62<br>184 | 63<br>187 | 64<br>190 | 65<br>193 | 66<br>196 | 67<br>199 | 68<br>202 | 69<br>205 | 70<br>208 |
|---|---|---|---|---|---|---|---|---|---|---|---|---|
| 73 | Consensus | | atc | cag | cag | acc | ttc | aat | ctc | ttc | agc | aca |
| 1 | IFN-α1b | | atc | cag | cag | atc | ttc | aac | ctc | ttt | acc | aca |
| 2 | IFN-α1a | | atc | cag | cag | atc | ttc | aac | ctc | ttt | acc | aca |
| 3 | IFN-α2A | | atc | cag | cag | atc | ttc | aat | ctc | ttc | agc | aca |
| 4 | IFN-α2b | | atc | cag | cag | atc | ttc | aat | ctc | ttt | agc | aca |
| 5 | IFN-α4a | | atc | cag | cag | acc | ttc | aat | ctc | ttc | agc | aca |
| 6 | IFN-α4b | | atc | cag | cag | acc | ttc | aat | ctc | ttc | agc | aca |
| 7 | IFN-α5 | | atc | cag | cag | acc | ttc | aat | ctc | ttc | agc | aca |
| 8 | IFN-α6 | | ATT | cag | cag | acc | ttc | aat | ctc | ttc | agc | aca |
| 9 | IFN-α7 | | atc | cag | cag | acc | ttc | aat | ctc | ttc | agc | aca |
| 10 | IFN-α8 | | atc | cag | cag | acc | ttc | aac | ctc | ttc | agc | aca |
| 11 | IFN-α10 | | atc | cag | cag | acc | ttc | aat | ctc | ttc | agc | aca |
| 12 | IFN-α14 | | ATG | cag | cag | acc | ttc | aat | ctc | ttc | agc | aca |
| 13 | IFN-α16 | | atc | cag | cag | acc | ttc | aat | ctc | ttc | agc | aca |
| 14 | IFN-α17 | | atc | cag | cag | acc | ttc | aat | ctc | ttc | agc | aca |
| 15 | IFN-α21 | | atc | cag | cag | acc | ttc | aat | ctc | ttc | agc | aca |

| SEQ ID NO: | | Codon<br>Position | 71<br>211 | 72<br>214 | 73<br>217 | 74<br>220 | 75<br>223 | 76<br>226 | 77<br>229 | 78<br>232 | 79<br>235 | 80<br>238 |
|---|---|---|---|---|---|---|---|---|---|---|---|---|
| 73 | Consensus | | aag | gac | tca | tct | gct | gct | tgg | gat | gag | agc |
| 1 | IFN-α1b | | aaa | gat | tca | tct | gct | gct | tgg | gat | gag | gac |
| 2 | IFN-α1a | | aaa | gat | tca | tct | gct | gct | tgg | gat | gag | gac |
| 3 | IFN-α2A | | aag | gac | tca | tct | gct | gct | tgg | gat | gag | acc |
| 4 | IFN-α2b | | aag | gac | tca | tct | gct | gct | tgg | gat | gag | acc |
| 5 | IFN-α4a | | gag | gac | tca | tct | gct | gct | tgg | gaa | cag | agc |
| 6 | IFN-α4b | | gag | gac | tca | tct | gct | gct | tgg | gaa | cag | agc |
| 7 | IFN-α5 | | aag | gac | tca | tct | gct | act | tgg | gat | gag | ACA |
| 8 | IFN-α6 | | aag | gac | tca | tct | GTT | gct | tgg | gat | gag | AGG |
| 9 | IFN-α7 | | gag | gac | tca | tct | gct | gct | tgg | gaa | cag | agc |
| 10 | IFN-α8 | | aag | gac | tca | tct | gct | gct | TTG | gat | gag | acc |
| 11 | IFN-α10 | | gag | gac | tca | tct | gct | gct | tgg | gaa | cag | agc |
| 12 | IFN-α14 | | aag | AAC | tca | tct | gct | gct | tgg | gat | gag | acc |
| 13 | IFN-α16 | | aag | gat | tca | tct | gct | gct | tgg | gat | gag | acc |
| 14 | IFN-α17 | | gag | gac | tca | tct | gct | gct | tgg | gaa | cag | agc |
| 15 | IFN-α21 | | aag | gac | tca | tct | gct | act | tgg | gaa | cag | agc |

| SEQ ID NO: | | Codon<br>Position | 81<br>241 | 82<br>244 | 83<br>247 | 84<br>250 | 85<br>253 | 86<br>256 | 87<br>259 | 88<br>262 | 89<br>265 | 90<br>268 |
|---|---|---|---|---|---|---|---|---|---|---|---|---|
| 73 | Consensus | | ctc | cta | gac | aaa | ttt | tac | act | gaa | ctt | tac |
| 1 | IFN-α1b | | ctc | cta | gac | aaa | ttc | tgc | acc | gaa | ctc | tac |
| 2 | IFN-α1a | | ctc | cta | gac | aaa | ttc | tgc | acc | gaa | ctc | tac |
| 3 | IFN-α2A | | ctc | cta | gac | aaa | ttc | tac | act | gaa | ctc | tac |
| 4 | IFN-α2b | | ctc | cta | gac | aaa | ttc | tac | act | gaa | ctc | tac |
| 5 | IFN-α4a | | ctc | cta | gaa | aaa | ttt | tcc | act | gaa | ctt | tac |
| 6 | IFN-α4b | | ctc | cta | gaa | aaa | ttt | tcc | act | gaa | ctt | tac |
| 7 | IFN-α5 | | ctt | cta | gac | aaa | ttc | tac | act | gaa | ctt | tac |
| 8 | IFN-α6 | | ctt | cta | gac | aaa | CTC | TAT | act | gaa | ctt | tac |
| 9 | IFN-α7 | | ctc | cta | gaa | aaa | ttt | tcc | act | gaa | ctt | tac |
| 10 | IFN-α8 | | ctt | cta | GAT | GAA | ttc | tac | ATC | gaa | ctt | GAC |
| 11 | IFN-α10 | | ctc | cta | gaa | aaa | ttt | tcc | act | gaa | ctt | tac |
| 12 | IFN-α14 | | ctc | cta | gaa | aaa | ttt | tcc | att | gaa | ctt | ttc |
| 13 | IFN-α16 | | ctc | cta | gac | aaa | ttc | tac | att | gaa | ctt | ttc |
| 14 | IFN-α17 | | ctc | cta | gaa | aaa | ttt | tcc | act | gaa | ctt | tac |
| 15 | IFN-α21 | | ctc | cta | gaa | aaa | ttt | tcc | act | gaa | ctt | AAC |

| SEQ ID NO: | | Codon<br>Position | 91<br>271 | 92<br>274 | 93<br>277 | 94<br>280 | 95<br>283 | 96<br>286 | 97<br>289 | 98<br>292 | 99<br>295 | 100<br>298 |
|---|---|---|---|---|---|---|---|---|---|---|---|---|
| 73 | Consensus | | cag | caa | ctg | aat | gac | ctg | gaa | gca | tgt | gtg |
| 1 | IFN-α1b | | cag | cag | ctg | aat | gac | ttg | gaa | gcc | tgt | gtg |
| 2 | IFN-α1a | | cag | cag | ctg | aat | gac | ttg | gaa | gcc | tgt | gtg |
| 3 | IFN-α2A | | cag | cag | ctg | aat | gac | ctg | gaa | gcc | tgt | gtg |
| 4 | IFN-α2b | | cag | cag | ctg | aat | gac | ctg | gaa | gcc | tgt | gtg |
| 5 | IFN-α4a | | cag | caa | ctg | aat | gac | ctg | gaa | gca | tgt | gtg |
| 6 | IFN-α4b | | cag | caa | ctg | aat | gac | ctg | gaa | gca | tgt | gtg |
| 7 | IFN-α5 | | cag | cag | ctg | aat | gac | ctg | gaa | gcc | tgt | ATG |
| 8 | IFN-α6 | | cag | cag | ctg | aat | gac | ctg | gaa | gcc | tgt | gtg |

TABLE 3-continued

| SEQ ID NO: | | Codon Position | 91 271 | 92 274 | 93 277 | 94 280 | 95 283 | 96 286 | 97 289 | 98 292 | 99 295 | 100 298 |
|---|---|---|---|---|---|---|---|---|---|---|---|---|
| 9 | IFN-α7 | | cag | caa | ctg | aat | gac | ctg | gaa | gca | tgt | gtg |
| 10 | IFN-α8 | | cag | cag | ctg | aat | gac | ctg | GAG | TCC | tgt | gtg |
| 11 | IFN-α10 | | cag | caa | ctg | aat | gac | ctg | gaa | gca | tgt | gtg |
| 12 | IFN-α14 | | cag | caa | ATG | aat | gac | ctg | gaa | gca | tgt | gtg |
| 13 | IFN-α16 | | cag | caa | ctg | aat | gac | CTA | gaa | gcc | tgt | gtg |
| 14 | IFN-α17 | | cag | caa | ctg | aat | AAC | CTA | gaa | gca | tgt | gtg |
| 15 | IFN-α21 | | cag | cag | ctg | aat | gac | ATG | gaa | gcc | TGC | gtg |

| SEQ ID NO: | | Codon Position | 101 301 | 102 304 | 103 307 | 104 310 | 105 213 | 106 316 | 107 319 | 108 322 | 109 325 | 110 328 |
|---|---|---|---|---|---|---|---|---|---|---|---|---|
| 73 | Consensus | | ata | cag | gag | gtt | ggg | gtg | gaa | gag | act | ccc |
| 1 | IFN-α1b | | atg | cag | gag | gag | agg | gtg | gga | gaa | act | ccc |
| 2 | IFN-α1a | | atg | cag | gag | gag | agg | gtg | gga | gaa | act | ccc |
| 3 | IFN-α2A | | ata | cag | ggg | gtg | ggg | gtg | aca | gag | act | ccc |
| 4 | IFN-α2b | | ata | cag | ggg | gtg | ggg | gtg | aca | gag | act | ccc |
| 5 | IFN-α4a | | ata | cag | gag | gtt | ggg | gtg | gaa | gag | act | ccc |
| 6 | IFN-α4b | | ata | cag | gag | gtt | ggg | gtg | gaa | gag | act | ccc |
| 7 | IFN-α5 | | atg | cag | gag | gtt | GGA | gtg | gaa | GAC | act | CCT |
| 8 | IFN-α6 | | atg | cag | gtg | TGG | gtg | gga | GGG | act | ccc | |
| 9 | IFN-α7 | | ata | cag | gag | gtt | ggg | gtg | gaa | gag | act | ccc |
| 10 | IFN-α8 | | atg | cag | GAA | gtg | ggg | gtg | ATA | gag | TCT | ccc |
| 11 | IFN-α10 | | ata | cag | gag | gtt | ggg | gtg | gaa | gag | act | ccc |
| 12 | IFN-α14 | | ata | cag | gag | gtt | ggg | gtg | gaa | gag | act | ccc |
| 13 | IFN-α16 | | ACA | cag | gag | gtt | ggg | gtg | gaa | gag | ATT | GCC |
| 14 | IFN-α17 | | ata | cag | gag | gtt | ggg | ATG | gaa | gag | act | ccc |
| 15 | IFN-α21 | | ata | cag | gag | gtt | ggg | gtg | gaa | gag | act | ccc |

| SEQ ID NO: | | Codon Position | 111 331 | 112 334 | 113 337 | 114 340 | 115 343 | 116 346 | 117 349 | 118 352 | 119 355 | 120 358 |
|---|---|---|---|---|---|---|---|---|---|---|---|---|
| 73 | Consensus | | ctg | atg | aat | gag | gac | tcc | atc | ctg | gct | gtg |
| 1 | IFN-α1b | | ctg | atg | aat | gtg | gac | tcc | atc | ttg | gct | gtg |
| 2 | IFN-α1a | | ctg | atg | aat | GCG | gac | tcc | atc | ttg | gct | gtg |
| 3 | IFN-α2A | | ctg | atg | aag | gag | gac | tcc | att | ctg | gct | gtg |
| 4 | IFN-α2b | | ctg | atg | aag | gag | gac | tcc | att | ctg | gct | gtg |
| 5 | IFN-α4a | | ctg | atg | aag | gag | gac | tcc | atc | ctg | gct | gtg |
| 6 | IFN-α4b | | ctg | atg | aat | gtg | gac | tcc | atc | ctg | gct | gtg |
| 7 | IFN-α5 | | ctg | atg | aat | gtg | gac | TCT | atc | ctg | act | gtg |
| 8 | IFN-α6 | | ctg | atg | aat | gag | gac | tcc | atc | ctg | gct | gtg |
| 9 | IFN-α7 | | ctg | atg | aat | gag | gac | TTC | atc | ctg | gct | gtg |
| 10 | IFN-α8 | | ctg | atg | TAC | gag | gac | TTC | atc | ctg | gct | gtg |
| 11 | IFN-α10 | | ctg | atg | aat | gag | gac | tcc | atc | ctg | gct | gtg |
| 12 | IFN-α14 | | ctg | atg | aat | gag | gac | tcc | atc | ctg | gct | gtg |
| 13 | IFN-α16 | | ctg | atg | aat | gag | gac | tcc | atc | ctg | gct | gtg |
| 14 | IFN-α17 | | ctg | atg | aat | gag | gac | tcc | atc | ctg | gct | gtg |
| 15 | IFN-α21 | | ctg | atg | aat | gtg | gac | tcc | atc | ttg | gct | gtg |

| SEQ ID NO: | | Codon Position | 121 361 | 122 364 | 123 367 | 124 370 | 125 373 | 126 376 | 127 379 | 128 382 | 129 385 | 130 388 |
|---|---|---|---|---|---|---|---|---|---|---|---|---|
| 73 | Consensus | | agg | aaa | tac | ttc | caa | aga | atc | act | ctt | tat |
| 1 | IFN-α1b | | aag | aaa | tac | ttc | cga | aga | atc | act | ctc | tat |
| 2 | IFN-α1a | | aag | aaa | tac | ttc | cga | aga | atc | act | ctc | tat |
| 3 | IFN-α2A | | agg | aaa | tac | ttc | caa | aga | atc | act | ctc | tat |
| 4 | IFN-α2b | | agg | aaa | tac | ttc | caa | aga | atc | act | ctc | tat |
| 5 | IFN-α4a | | agg | aaa | tac | ttc | caa | aga | atc | act | ctt | tat |
| 6 | IFN-α4b | | agg | aaa | tac | ttc | caa | aga | atc | act | ctt | tat |
| 7 | IFN-α5 | | AGA | aaa | tac | ttt | caa | aga | atc | ACC | ctc | tat |
| 8 | IFN-α6 | | AGA | aaa | tac | ttc | caa | aga | atc | act | ctc | TAC |
| 9 | IFN-α7 | | agg | aaa | tac | ttc | caa | aga | atc | act | ctt | tat |
| 10 | IFN-α8 | | agg | aaa | tac | ttc | caa | aga | atc | act | CTA | tat |
| 11 | IFN-α10 | | agg | aaa | tac | ttc | caa | aga | atc | act | ctt | tat |
| 12 | IFN-α14 | | aag | aaa | tac | ttc | caa | aga | atc | act | ctt | tat |
| 13 | IFN-α16 | | agg | aaa | tac | ttt | caa | aga | atc | act | ctt | tat |
| 14 | IFN-α17 | | agg | aaa | tac | ttc | caa | aga | atc | act | ctt | tat |
| 15 | IFN-α21 | | aag | aaa | tac | ttc | caa | aga | atc | act | ctt | tat |

| SEQ ID NO: | | Codon Position | 131 391 | 132 394 | 133 397 | 134 400 | 135 403 | 136 406 | 137 409 | 138 412 | 139 415 | 140 418 |
|---|---|---|---|---|---|---|---|---|---|---|---|---|
| 73 | Consensus | | cta | aca | gag | aag | aaa | tac | agc | cct | tgt | gcc |
| 1 | IFN-α1b | | ctg | aca | gag | aag | aaa | tac | agc | cct | tgt | gcc |
| 2 | IFN-α1a | | ctg | aca | gag | aag | aaa | tac | agc | cct | tgt | gcc |
| 3 | IFN-α2A | | ctg | aaa | gag | aag | aaa | tac | agc | cct | tgt | gcc |
| 4 | IFN-α2b | | ctg | aaa | gag | aag | aaa | tac | agc | cct | tgt | gcc |

TABLE 3-continued

| SEQ ID NO: | | 132 | 133 | 134 | 135 | 136 | 137 | 138 | 139 | 140 |
|---|---|---|---|---|---|---|---|---|---|---|
| 5 | IFN-α4a | cta | aca | gag | aag | aaa | tac | agc | cct | tgt | gcc |
| 6 | IFN-α4b | cta | aca | gag | aag | aaa | tac | agc | cct | tgt | gcc |
| 7 | IFN-α5 | ctg | aca | gag | aag | aaa | tac | agc | cct | tgt | GCA |
| 8 | IFN-α6 | ctg | aca | gag | AAA | AAG | tac | agc | cct | tgt | gcc |
| 9 | IFN-α7 | cta | atg | gag | aag | aaa | tac | agc | cct | tgt | gcc |
| 10 | IFN-α8 | ctg | aca | gag | aag | aaa | tac | agc | cct | TCT | gcc |
| 11 | IFN-α10 | cta | ATA | gag | AGG | aaa | tac | agc | cct | tgt | gcc |
| 12 | IFN-α14 | ctg | atg | gag | aag | aaa | tac | agc | cct | tgt | gcc |
| 13 | IFN-α16 | ctg | atg | GGG | aaa | aaa | tac | agc | cct | tgt | gcc |
| 14 | IFN-α17 | cta | aca | gag | aag | aaa | tac | agc | cct | tgt | gcc |
| 15 | IFN-α21 | ctg | aca | gag | aag | aaa | tac | agc | cct | tgt | GCT |

| SEQ ID NO: | Codon | 141 | 142 | 143 | 144 | 145 | 146 | 147 | 148 | 149 | 150 |
|---|---|---|---|---|---|---|---|---|---|---|---|
| | Position | 421 | 424 | 427 | 430 | 433 | 436 | 439 | 442 | 445 | 448 |
| 73 | Consensus | tgg | gag | gtt | gtc | aga | gca | gaa | atc | atg | aga |
| 1 | IFN-α1b | tgg | gag | gtt | gtc | aga | gca | gaa | atc | atg | aga |
| 2 | IFN-α1a | tgg | gag | gtt | gtc | aga | gca | gaa | atc | atg | aga |
| 3 | IFN-α2A | tgg | gag | gtt | gtc | aga | gca | gaa | atc | atg | aga |
| 4 | IFN-α2b | tgg | gag | gtt | gtc | aga | gca | gaa | atc | atg | aga |
| 5 | IFN-α4a | tgg | gag | gtt | gtc | aga | gca | gaa | atc | atg | aga |
| 6 | IFN-α4b | tgg | gag | gtt | gtc | aga | gca | gaa | atc | atg | aga |
| 7 | IFN-α5 | tgg | gag | gtt | gtc | aga | gca | gaa | atc | atg | aga |
| 8 | IFN-α6 | tgg | gag | gtt | gtc | aga | gca | gaa | atc | atg | aga |
| 9 | IFN-α7 | tgg | gag | gtt | gtc | aga | gca | gaa | atc | atg | aga |
| 10 | IFN-α8 | tgg | gag | gtt | gtc | aga | gca | gaa | atc | atg | aga |
| 11 | IFN-α10 | tgg | gag | gtt | gtc | aga | gca | gaa | atc | atg | aga |
| 12 | IFN-α14 | tgg | gag | gtt | gtc | aga | gca | gaa | atc | atg | aga |
| 13 | IFN-α16 | tgg | gag | gtt | gtc | aga | gca | gaa | atc | atg | aga |
| 14 | IFN-α17 | tgg | gag | gtt | gtc | aga | gca | gaa | atc | atg | aga |
| 15 | IFN-α21 | tgg | gag | gtt | gtc | aga | gca | gaa | atc | atg | aga |

| SEQ ID NO: | Codon | 151 | 152 |
|---|---|---|---|
| | Position | 451 | 454 |
| 73 | Consensus | tcc | ttc |
| 1 | IFN-α1b | tcc | ctc |
| 2 | IFN-α1a | tcc | ctc |
| 3 | IFN-α2A | tct | ttt |
| 4 | IFN-α2b | tct | ttt |
| 5 | IFN-α4a | tcc | ctc |
| 6 | IFN-α4b | tcc | ctc |
| 7 | IFN-α5 | tcc | ttc |
| 8 | IFN-α6 | tcc | ttc |
| 9 | IFN-α7 | tcc | ttc |
| 10 | IFN-α8 | tcc | ttc |
| 11 | IFN-α10 | tcc | ctc |
| 12 | IFN-α14 | tcc | ctc |
| 13 | IFN-α16 | tcc | ttc |
| 14 | IFN-α17 | tct | ctc |
| 15 | IFN-α21 | tcc | ttc |

Table 4, below, depicts the mature protein sequence for IFN-alpha subtypes.

TABLE 4

| SEQ ID NO: | Codon | 1 | 2 | 3 | 4 | 5 | 6 | 7 | 8 | 9 | 10 |
|---|---|---|---|---|---|---|---|---|---|---|---|
| 75 | Consensus | Cys | Asp | Leu | Pro | Gln | Thr | His | Ser | Leu | Gly |
| 16 | IFN-α1b | Cys | Asp | Leu | Pro | Glu | Thr | His | Ser | Leu | Asp |
| 17 | IFN-α1a | Cys | Asp | Leu | Pro | Glu | Thr | His | Ser | Leu | Asp |
| 18 | IFN-α2a | Cys | Asp | Leu | Pro | Glu | Thr | His | Ser | Leu | Gly |
| 19 | IFN-α2b | Cys | Asp | Leu | Pro | Gln | Thr | His | Ser | Leu | Gly |
| 20 | IFN-α4a | Cys | Asp | Leu | Pro | Gln | Thr | His | Ser | Leu | Gly |
| 21 | IFN-α4b | Cys | Asp | Leu | Pro | Gln | Thr | His | Ser | Leu | Gly |
| 22 | IFN-α5 | Cys | Asp | Leu | Pro | Gln | Thr | His | Ser | Leu | Ser |
| 23 | IFN-α6 | Cys | Asp | Leu | Pro | Gln | Thr | His | Ser | Leu | Gly |
| 24 | IFN-α7 | Cys | Asp | Leu | Pro | Gln | Thr | His | Ser | Leu | Arg |
| 25 | IFN-α8 | Cys | Asp | Leu | Pro | Gln | Thr | His | Ser | Leu | Gly |
| 26 | IFN-α10 | Cys | Asp | Leu | Pro | Gln | Thr | His | Ser | Leu | Gly |
| 27 | IFN-α14 | Cys | Asn | Leu | Ser | Gln | Thr | His | Ser | Leu | Asn |
| 28 | IFN-α16 | Cys | Asp | Leu | Pro | Gln | Thr | His | Ser | Leu | Gly |
| 29 | IFN-α17 | Cys | Asp | Leu | Pro | Gln | Thr | His | Ser | Leu | Gly |
| 74 | IFN-α21 | Cys | Asp | Leu | Pro | Gln | Thr | His | Ser | Leu | Gly |

| SEQ ID NO: | Codon | 11 | 12 | 13 | 14 | 15 | 16 | 17 | 18 | 19 | 20 |
|---|---|---|---|---|---|---|---|---|---|---|---|
| 75 | Consensus | Asn | Arg | Arg | Ala | Leu | Ile | Leu | Leu | Ala | Gln |
| 16 | IFN-α1b | Asn | Arg | Arg | Thr | Leu | Met | Leu | Leu | Ala | Gln |
| 17 | IFN-α1a | Asn | Arg | Arg | Thr | Leu | Met | Leu | Leu | Ala | Gln |
| 18 | IFN-α2a | Ser | Arg | Arg | Thr | Leu | Met | Leu | Leu | Ala | Gln |
| 19 | IFN-α2b | Ser | Arg | Arg | Thr | Leu | Met | Leu | Leu | Ala | Gln |
| 20 | IFN-α4a | Asn | Arg | Arg | Ala | Leu | Ile | Leu | Leu | Ala | Gln |
| 21 | IFN-α4b | Asn | Arg | Arg | Ala | Leu | Ile | Leu | Leu | Ala | Gln |
| 22 | IFN-α5 | Asn | Arg | Arg | Thr | Leu | Met | Ile | Met | Ala | Gln |
| 23 | IFN-α6 | His | Arg | Arg | Thr | Leu | Met | Leu | Leu | Ala | Gln |
| 24 | IFN-α7 | Asn | Arg | Arg | Ala | Leu | Ile | Leu | Leu | Ala | Gln |
| 25 | IFN-α8 | Asn | Arg | Arg | Ala | Leu | Ile | Leu | Leu | Ala | Gln |
| 26 | IFN-α10 | Asn | Arg | Arg | Ala | Leu | Ile | Leu | Leu | Gly | Gln |
| 27 | IFN-α14 | Asn | Arg | Arg | Thr | Leu | Met | Leu | Met | Ala | Gln |
| 28 | IFN-α16 | Asn | Arg | Arg | Ala | Leu | Ile | Leu | Leu | Ala | Gln |

TABLE 4-continued

| SEQ ID NO: | Name | 21 | 22 | 23 | 24 | 25 | 26 | 27 | 28 | 29 | 30 |
|---|---|---|---|---|---|---|---|---|---|---|---|
| 29 | IFN-α17 | Asn | Arg | Arg | Ala | Leu | Ile | Leu | Leu | Ala | Gln |
| 74 | IFN-α21 | Asn | Arg | Arg | Ala | Leu | Ile | Leu | Leu | Ala | Gln |

| SEQ ID NO: | Codon | 21 | 22 | 23 | 24 | 25 | 26 | 27 | 28 | 29 | 30 |
|---|---|---|---|---|---|---|---|---|---|---|---|
| 75 | Consensus | Met | Gly | Arg | Ile | Ser | Pro | Phe | Ser | Cys | Leu |
| 16 | IFN-α1b | Met | Ser | Arg | Ile | Ser | Pro | Ser | Ser | Cys | Leu |
| 17 | IFN-α1a | Met | Ser | Arg | Ile | Ser | Pro | Ser | Ser | Cys | Leu |
| 18 | IFN-α2a | Met | Arg | Lys | Ile | Ser | Leu | Phe | Ser | Cys | Leu |
| 19 | IFN-α2b | Met | Arg | Arg | Ile | Ser | Leu | Phe | Ser | Cys | Leu |
| 20 | IFN-α4a | Met | Gly | Arg | Ile | Ser | His | Phe | Ser | Cys | Leu |
| 21 | IFN-α4b | Met | Gly | Arg | Ile | Ser | His | Phe | Ser | Cys | Leu |
| 22 | IFN-α5 | Met | Gly | Arg | Ile | Ser | Pro | Phe | Ser | Cys | Leu |
| 23 | IFN-α6 | Met | Arg | Arg | Ile | Ser | Leu | Phe | Ser | Cys | Leu |
| 24 | IFN-α7 | Met | Gly | Arg | Ile | Ser | Pro | Phe | Ser | Cys | Leu |
| 25 | IFN-α8 | Met | Arg | Arg | Ile | Ser | Pro | Phe | Ser | Cys | Leu |
| 26 | IFN-α10 | Met | Gly | Arg | Ile | Ser | Pro | Phe | Ser | Cys | Leu |
| 27 | IFN-α14 | Met | Arg | Arg | Ile | Ser | Pro | Phe | Ser | Cys | Leu |
| 28 | IFN-α16 | Met | Gly | Arg | Ile | Ser | His | Phe | Ser | Cys | Leu |
| 29 | IFN-α17 | Met | Gly | Arg | Ile | Ser | Pro | Phe | Ser | Cys | Leu |
| 74 | IFN-α21 | Met | Gly | Arg | Ile | Ser | Pro | Phe | Ser | Cys | Leu |

| SEQ ID NO: | Codon | 31 | 32 | 33 | 34 | 35 | 36 | 37 | 38 | 39 | 40 |
|---|---|---|---|---|---|---|---|---|---|---|---|
| 75 | Consensus | Lys | Asp | Arg | His | Asp | Phe | Gly | Phe | Pro | Gln |
| 16 | IFN-α1b | Met | Asp | Arg | His | Asp | Phe | Gly | Phe | Pro | Gln |
| 17 | IFN-α1a | Met | Asp | Arg | His | Asp | Phe | Gly | Phe | Pro | Gln |
| 18 | IFN-α2a | Lys | Asp | Arg | His | Asp | Phe | Gly | Phe | Pro | Gln |
| 19 | IFN-α2b | Lys | Asp | Arg | His | Asp | Phe | Gly | Phe | Pro | Glu |
| 20 | IFN-α4a | Lys | Asp | Arg | His | Asp | Phe | Gly | Phe | Pro | Glu |
| 21 | IFN-α4b | Lys | Asp | Arg | His | Asp | Phe | Gly | Phe | Pro | Glu |
| 22 | IFN-α5 | Lys | Asp | Arg | His | Asp | Phe | Gly | Phe | Pro | Gln |
| 23 | IFN-α6 | Lys | Asp | Arg | His | Asp | Phe | Arg | Phe | Pro | Gln |
| 24 | IFN-α7 | Lys | Asp | Arg | His | Glu | Phe | Arg | Phe | Pro | Glu |
| 25 | IFN-α8 | Lys | Asp | Arg | His | Asp | Phe | Glu | Phe | Pro | Gln |
| 26 | IFN-α10 | Lys | Asp | Arg | His | Asp | Phe | Arg | Ile | Pro | Gln |
| 27 | IFN-α14 | Lys | Asp | Arg | His | Asp | Phe | Glu | Phe | Pro | Gln |
| 28 | IFN-α16 | Lys | Asp | Arg | Tyr | Asp | Phe | Gly | Phe | Pro | Gln |
| 29 | IFN-α17 | Lys | Asp | Arg | Pro | Asp | Phe | Gly | Leu | Pro | Gln |
| 74 | IFN-α21 | Lys | Asp | Arg | His | Asp | Phe | Gly | Phe | Pro | Gln |

| SEQ ID NO: | Codon | 41 | 42 | 43 | 44 | 45 | 46 | 47 | 48 | 49 | 50 |
|---|---|---|---|---|---|---|---|---|---|---|---|
| 75 | Consensus | Glu | Glu | Phe | Asp | Gly | Asn | Gln | Phe | Gln | Lys |
| 16 | IFN-α1b | Glu | Glu | Phe | Asp | Gly | Asn | Gln | Phe | Gln | Lys |
| 17 | IFN-α1a | Glu | Glu | Phe | Asp | Gly | Asn | Gln | Phe | Gln | Lys |
| 18 | IFN-α2a | Glu | Glu | Phe | Gly | Asn | Gln | Phe | Gln | Lys | Ala |
| 19 | IFN-α2b | Glu | Glu | Phe | Gly | Asn | Gln | Phe | Gln | Lys | Ala |
| 20 | IFN-α4a | Glu | Glu | Phe | Asp | Gly | His | Gln | Phe | Gln | Lys |
| 21 | IFN-α4b | Glu | Glu | Phe | Asp | Gly | His | Gln | Phe | Gln | Lys |
| 22 | IFN-α5 | Glu | Glu | Phe | Asp | Gly | Asn | Gln | Phe | Gln | Lys |
| 23 | IFN-α6 | Glu | Glu | Phe | Asp | Gly | Asn | Gln | Phe | Gln | Lys |
| 24 | IFN-α7 | Glu | Glu | Phe | Asp | Gly | His | Gln | Phe | Gln | Lys |
| 25 | IFN-α8 | Glu | Glu | Phe | Asp | Asp | Lys | Gln | Phe | Gln | Lys |
| 26 | IFN-α10 | Glu | Glu | Phe | Asp | Gly | Asn | Gln | Phe | Gln | Lys |
| 27 | IFN-α14 | Glu | Glu | Phe | Asp | Gly | Asn | Gln | Phe | Gln | Lys |
| 28 | IFN-α16 | Glu | Val | Phe | Asp | Gly | Asn | Gln | Phe | Gln | Lys |
| 29 | IFN-α17 | Glu | Glu | Phe | Asp | Gly | Asn | Gln | Phe | Gln | Lys |
| 74 | IFN-α21 | Glu | Glu | Phe | Asp | Gly | Asn | Gln | Phe | Gln | Lys |

| SEQ ID NO: | Codon | 51 | 52 | 53 | 54 | 55 | 56 | 57 | 58 | 59 | 60 |
|---|---|---|---|---|---|---|---|---|---|---|---|
| 75 | Consensus | Ala | Gln | Ala | Ile | Ser | Val | Leu | His | Glu | Met |
| 16 | IFN-α1b | Ala | Pro | Ala | Ile | Ser | Val | Leu | His | Glu | Leu |
| 17 | IFN-α1a | Ala | Pro | Ala | Ile | Ser | Val | Leu | His | Glu | Leu |
| 18 | IFN-α2a | Glu | Thr | Ile | Pro | Val | Leu | His | Glu | Met | Ile |
| 19 | IFN-α2b | Glu | Thr | Ile | Pro | Val | Leu | His | Glu | Met | Ile |
| 20 | IFN-α4a | Ala | Gln | Ala | Ile | Ser | Val | Leu | His | Glu | Met |
| 21 | IFN-α4b | Thr | Gln | Ala | Ile | Ser | Val | Leu | His | Glu | Met |
| 22 | IFN-α5 | Ala | Gln | Ala | Ile | Ser | Val | Leu | His | Glu | Met |
| 23 | IFN-α6 | Ala | Glu | Ala | Ile | Ser | Val | Leu | His | Glu | Val |
| 24 | IFN-α7 | Thr | Gln | Ala | Ile | Ser | Val | Leu | His | Glu | Met |
| 25 | IFN-α8 | Ala | Gln | Ala | Ile | Ser | Val | Leu | His | Glu | Met |
| 26 | IFN-α10 | Ala | Gln | Ala | Ile | Ser | Val | Leu | His | Glu | Met |
| 27 | IFN-α14 | Ala | Gln | Ala | Ile | Ser | Val | Leu | His | Glu | Met |
| 28 | IFN-α16 | Ala | Gln | Ala | Ile | Ser | Ala | Phe | His | Glu | Met |
| 29 | IFN-α17 | Thr | Gln | Ala | Ile | Ser | Val | Leu | His | Glu | Met |
| 74 | IFN-α21 | Ala | Gln | Ala | Ile | Ser | Val | Leu | His | Glu | Met |

| SEQ ID NO: | Codon | 61 | 62 | 63 | 64 | 65 | 66 | 67 | 68 | 69 | 70 |
|---|---|---|---|---|---|---|---|---|---|---|---|
| 75 | Consensus | Ile | Gln | Gln | Thr | Phe | Asn | Leu | Phe | Ser | Thr |
| 16 | IFN-α1b | Ile | Gln | Gln | Thr | Phe | Asn | Leu | Phe | Thr | Thr |
| 17 | IFN-α1a | Ile | Gln | Gln | Ile | Phe | Asn | Leu | Phe | Thr | Thr |
| 18 | IFN-α2a | Gln | Gln | Ile | Phe | Asn | Leu | Phe | Ser | Thr | Lys |
| 19 | IFN-α2b | Gln | Gln | Ile | Phe | Asn | Leu | Phe | Ser | Thr | Lys |
| 20 | IFN-α4a | Ile | Gln | Gln | Thr | Phe | Asn | Leu | Phe | Ser | Thr |
| 21 | IFN-α4b | Ile | Gln | Gln | Thr | Phe | Asn | Leu | Phe | Ser | Thr |
| 22 | IFN-α5 | Ile | Gln | Gln | Thr | Phe | Asn | Leu | Phe | Ser | Thr |
| 23 | IFN-α6 | Ile | Gln | Gln | Thr | Phe | Asn | Leu | Phe | Ser | Thr |
| 24 | IFN-α7 | Ile | Gln | Gln | Thr | Phe | Asn | Leu | Phe | Ser | Thr |
| 25 | IFN-α8 | Ile | Gln | Gln | Thr | Phe | Asn | Leu | Phe | Ser | Thr |
| 26 | IFN-α10 | Ile | Gln | Gln | Thr | Phe | Asn | Leu | Phe | Ser | Thr |
| 27 | IFN-α14 | Met | Gln | Gln | Thr | Phe | Asn | Leu | Phe | Ser | Thr |
| 28 | IFN-α16 | Ile | Gln | Gln | Thr | Phe | Asn | Leu | Phe | Ser | Thr |
| 29 | IFN-α17 | Ile | Gln | Gln | Thr | Phe | Asn | Leu | Phe | Ser | Thr |
| 74 | IFN-α21 | Ile | Gln | Gln | Thr | Phe | Asn | Leu | Phe | Ser | Thr |

| SEQ ID NO: | Codon | 71 | 72 | 73 | 74 | 75 | 76 | 77 | 78 | 79 | 80 |
|---|---|---|---|---|---|---|---|---|---|---|---|
| 75 | Consensus | Lys | Asp | Ser | Ser | Ala | Ala | Trp | Asp | Glu | Ser |
| 16 | IFN-α1b | Lys | Asp | Ser | Ser | Ala | Ala | Trp | Asp | Glu | Asp |
| 17 | IFN-α1a | Lys | Asp | Ser | Ser | Ala | Ala | Trp | Asp | Glu | Asp |
| 18 | IFN-α2a | Asp | Ser | Ser | Ala | Ala | Trp | Asp | Glu | Thr | Leu |
| 19 | IFN-α2b | Asp | Ser | Ser | Ala | Ala | Trp | Asp | Glu | Thr | Leu |
| 20 | IFN-α4a | Glu | Asp | Ser | Ser | Ala | Ala | Trp | Glu | Gln | Ser |
| 21 | IFN-α4b | Glu | Asp | Ser | Ser | Ala | Ala | Trp | Glu | Gln | Ser |
| 22 | IFN-α5 | Lys | Asp | Ser | Ser | Ala | Thr | Trp | Asp | Glu | Thr |
| 23 | IFN-α6 | Lys | Asp | Ser | Ser | Val | Ala | Trp | Asp | Glu | Arg |
| 24 | IFN-α7 | Glu | Asp | Ser | Ser | Ala | Ala | Trp | Asp | Glu | Thr |
| 25 | IFN-α8 | Lys | Asp | Ser | Ser | Ala | Ala | Leu | Asp | Glu | Thr |
| 26 | IFN-α10 | Glu | Asp | Ser | Ser | Ala | Ala | Trp | Glu | Gln | Ser |
| 27 | IFN-α14 | Lys | Asn | Ser | Ser | Ala | Ala | Trp | Asp | Glu | Thr |
| 28 | IFN-α16 | Lys | Asp | Ser | Ser | Ala | Ala | Trp | Asp | Glu | Thr |
| 29 | IFN-α17 | Glu | Asp | Ser | Ser | Ala | Ala | Trp | Glu | Gln | Ser |
| 74 | IFN-α21 | Lys | Asp | Ser | Ser | Ala | Thr | Trp | Glu | Gln | Ser |

| SEQ ID NO: | Codon | 81 | 82 | 83 | 84 | 85 | 86 | 87 | 88 | 89 | 90 |
|---|---|---|---|---|---|---|---|---|---|---|---|
| 75 | Consensus | Leu | Leu | Asp | Lys | Phe | Tyr | Thr | Glu | Leu | Tyr |
| 16 | IFN-α1b | Leu | Leu | Asp | Lys | Phe | Cys | Thr | Glu | Leu | Tyr |
| 17 | IFN-α1a | Leu | Leu | Asp | Lys | Phe | Cys | Thr | Glu | Leu | Tyr |
| 18 | IFN-α2a | Leu | Asp | Lys | Phe | Tyr | Thr | Glu | Leu | Tyr | Gln |
| 19 | IFN-α2b | Leu | Asp | Lys | Phe | Tyr | Thr | Glu | Leu | Tyr | Gln |
| 20 | IFN-α4a | Leu | Leu | Glu | Lys | Phe | Ser | Thr | Glu | Leu | Tyr |
| 21 | IFN-α4b | Leu | Leu | Glu | Lys | Phe | Ser | Thr | Glu | Leu | Tyr |
| 22 | IFN-α5 | Leu | Leu | Asp | Lys | Phe | Thr | Thr | Glu | Leu | Tyr |
| 23 | IFN-α6 | Leu | Leu | Asp | Lys | Leu | Tyr | Thr | Glu | Leu | Tyr |
| 24 | IFN-α7 | Leu | Leu | Glu | Lys | Phe | Ser | Thr | Glu | Leu | Tyr |
| 25 | IFN-α8 | Leu | Leu | Asp | Glu | Phe | Tyr | Ile | Glu | Leu | Asp |
| 26 | IFN-α10 | Leu | Leu | Glu | Lys | Phe | Ser | Thr | Glu | Leu | Tyr |
| 27 | IFN-α14 | Leu | Leu | Glu | Lys | Phe | Tyr | Ile | Glu | Leu | Phe |
| 28 | IFN-α16 | Leu | Leu | Asp | Lys | Phe | Tyr | Ile | Glu | Leu | Phe |
| 29 | IFN-α17 | Leu | Leu | Glu | Lys | Phe | Ser | Thr | Glu | Leu | Tyr |
| 74 | IFN-α21 | Leu | Leu | Glu | Lys | Phe | Ser | Thr | Glu | Leu | Asn |

| SEQ ID NO: | Codon | 91 | 92 | 93 | 94 | 95 | 96 | 97 | 98 | 99 | 100 |
|---|---|---|---|---|---|---|---|---|---|---|---|
| 75 | Consensus | Gln | Gln | Leu | Asn | Asp | Leu | Glu | Ala | Cys | Val |
| 16 | IFN-α1b | Gln | Gln | Leu | Asn | Asp | Leu | Glu | Ala | Cys | Val |
| 17 | IFN-α1a | Gln | Gln | Leu | Asn | Asp | Leu | Glu | Ala | Cys | Val |
| 18 | IFN-α2a | Gln | Leu | Asn | Asp | Leu | Glu | Ala | Cys | Val | Ile |
| 19 | IFN-α2b | Gln | Leu | Asn | Asp | Leu | Glu | Ala | Cys | Val | Ile |
| 20 | IFN-α4a | Gln | Gln | Leu | Asn | Asp | Leu | Glu | Ala | Cys | Val |

TABLE 4-continued

| SEQ ID NO: | | 101 | 102 | 103 | 104 | 105 | 106 | 107 | 108 | 109 | 110 |
|---|---|---|---|---|---|---|---|---|---|---|---|
| 21 | IFN-α4b | Gln | Gln | Leu | Asn | Asp | Leu | Glu | Ala | Cys | Val |
| 22 | IFN-α5 | Gln | Gln | Leu | Asn | Asp | Leu | Glu | Ala | Cys | Met |
| 23 | IFN-α6 | Gln | Gln | Leu | Asn | Asp | Leu | Glu | Ala | Cys | Val |
| 24 | IFN-α7 | Gln | Gln | Leu | Asn | Asp | Leu | Glu | Ala | Cys | Val |
| 25 | IFN-α8 | Gln | Gln | Leu | Asn | Asp | Leu | Glu | Ser | Cys | Val |
| 26 | IFN-α10 | Gln | Gln | Leu | Asn | Asp | Leu | Glu | Ala | Cys | Val |
| 27 | IFN-α14 | Gln | Gln | Met | Asn | Asp | Leu | Glu | Ala | Cys | Val |
| 28 | IFN-α16 | Gln | Gln | Leu | Asn | Asp | Leu | Glu | Ala | Cys | Val |
| 29 | IFN-α17 | Gln | Gln | Leu | Asn | Asn | Leu | Glu | Ala | Cys | Val |
| 74 | IFN-α21 | Gln | Gln | Leu | Asn | Asp | Met | Glu | Ala | Cys | Val |

| SEQ ID NO: | Codon | 101 | 102 | 103 | 104 | 105 | 106 | 107 | 108 | 109 | 110 |
|---|---|---|---|---|---|---|---|---|---|---|---|
| 75 | Consensus | Ile | Gln | Glu | Val | Gly | Val | Glu | Glu | Thr | Pro |
| 16 | IFN-α1b | Met | Gln | Glu | Glu | Arg | Val | Gly | Glu | Thr | Pro |
| 17 | IFN-α1a | Met | Gln | Glu | Glu | Arg | Val | Gly | Glu | Thr | Pro |
| 18 | IFN-α2a | Gln | Gly | Val | Gly | Val | Thr | Glu | Thr | Pro | Leu |
| 19 | IFN-α2b | Gln | Gly | Val | Gly | Val | Thr | Glu | Thr | Pro | Leu |
| 20 | IFN-α4a | Ile | Gln | Glu | Val | Gly | Val | Glu | Glu | Thr | Pro |
| 21 | IFN-α4b | Ile | Gln | Glu | Val | Gly | Val | Glu | Glu | Thr | Pro |
| 22 | IFN-α5 | Met | Gln | Glu | Val | Gly | Val | Glu | Asp | Thr | Pro |
| 23 | IFN-α6 | Met | Gln | Glu | Val | Trp | Val | Gly | Gly | Thr | Pro |
| 24 | IFN-α7 | Ile | Gln | Glu | Val | Gly | Val | Glu | Glu | Thr | Pro |
| 25 | IFN-α8 | Met | Gln | Glu | Val | Gly | Val | Ile | Glu | Ser | Pro |
| 26 | IFN-α10 | Ile | Gln | Glu | Val | Gly | Val | Glu | Glu | Thr | Pro |
| 27 | IFN-α14 | Ile | Gln | Glu | Val | Gly | Val | Glu | Glu | Thr | Pro |
| 28 | IFN-α16 | Thr | Gln | Glu | Val | Gly | Val | Glu | Glu | Ile | Ala |
| 29 | IFN-α17 | Ile | Gln | Glu | Val | Gly | Met | Glu | Glu | Thr | Pro |
| 74 | IFN-α21 | Ile | Gln | Glu | Val | Gly | Val | Glu | Glu | Thr | Pro |

| SEQ ID NO: | Codon | 111 | 112 | 113 | 114 | 115 | 116 | 117 | 118 | 119 | 120 |
|---|---|---|---|---|---|---|---|---|---|---|---|
| 75 | Consensus | Leu | Met | Asn | Glu | Asp | Ser | Ile | Leu | Ala | Val |
| 16 | IFN-α1b | Leu | Met | Asn | Val | Asp | Ser | Ile | Leu | Ala | Val |
| 17 | IFN-α1a | Leu | Met | Asn | Ala | Asp | Ser | Ile | Leu | Ala | Val |
| 18 | IFN-α2a | Met | Lys | Glu | Asp | Ser | Ile | Leu | Ala | Val | Arg |
| 19 | IFN-α2b | Met | Lys | Glu | Asp | Ser | Ile | Leu | Ala | Val | Arg |
| 20 | IFN-α4a | Leu | Met | Asn | Glu | Asp | Ser | Ile | Leu | Ala | Val |
| 21 | IFN-α4b | Leu | Met | Asn | Val | Asp | Ser | Ile | Leu | Ala | Val |
| 22 | IFN-α5 | Leu | Met | Asn | Val | Asp | Ser | Ile | Leu | Thr | Val |
| 23 | IFN-α6 | Leu | Met | Asn | Glu | Asp | Ser | Ile | Leu | Ala | Val |
| 24 | IFN-α7 | Leu | Met | Asn | Glu | Asp | Phe | Ile | Leu | Ala | Val |
| 25 | IFN-α8 | Leu | Met | Tyr | Glu | Asp | Ser | Ile | Leu | Ala | Val |
| 26 | IFN-α10 | Leu | Met | Asn | Glu | Asp | Ser | Ile | Leu | Ala | Val |
| 27 | IFN-α14 | Leu | Met | Asn | Glu | Asp | Ser | Ile | Leu | Ala | Val |
| 28 | IFN-α16 | Leu | Met | Asn | Glu | Asp | Ser | Ile | Leu | Ala | Val |
| 29 | IFN-α17 | Leu | Met | Asn | Glu | Asp | Ser | Ile | Leu | Ala | Val |
| 74 | IFN-α21 | Leu | Met | Asn | Val | Asp | Ser | Ile | Leu | Ala | Val |

| SEQ ID NO: | Codon | 121 | 122 | 123 | 124 | 125 | 126 | 127 | 128 | 129 | 130 |
|---|---|---|---|---|---|---|---|---|---|---|---|
| 75 | Consensus | Arg | Lys | Tyr | Phe | Gln | Arg | Ile | Thr | Leu | Tyr |
| 16 | IFN-α1b | Lys | Lys | Tyr | Phe | Arg | Arg | Ile | Thr | Leu | Tyr |
| 17 | IFN-α1a | Lys | Lys | Tyr | Phe | Arg | Arg | Ile | Thr | Leu | Tyr |
| 18 | IFN-α2a | Lys | Tyr | Phe | Gln | Arg | Ile | Thr | Leu | Tyr | Leu |
| 19 | IFN-α2b | Lys | Tyr | Phe | Gln | Arg | Ile | Thr | Leu | Tyr | Leu |
| 20 | IFN-α4a | Arg | Lys | Tyr | Phe | Gln | Arg | Ile | Thr | Leu | Tyr |
| 21 | IFN-α4b | Arg | Lys | Tyr | Phe | Gln | Arg | Ile | Thr | Leu | Tyr |
| 22 | IFN-α5 | Arg | Lys | Tyr | Phe | Gln | Arg | Ile | Thr | Leu | Tyr |
| 23 | IFN-α6 | Arg | Lys | Tyr | Phe | Gln | Arg | Ile | Thr | Leu | Tyr |
| 24 | IFN-α7 | Arg | Lys | Tyr | Phe | Gln | Arg | Ile | Thr | Leu | Tyr |
| 25 | IFN-α8 | Arg | Lys | Tyr | Phe | Gln | Arg | Ile | Thr | Leu | Tyr |
| 26 | IFN-α10 | Arg | Lys | Tyr | Phe | Gln | Arg | Ile | Thr | Leu | Tyr |
| 27 | IFN-α14 | Lys | Lys | Tyr | Phe | Gln | Arg | Ile | Thr | Leu | Tyr |
| 28 | IFN-α17 | Arg | Lys | Tyr | Phe | Gln | Arg | Ile | Thr | Leu | Tyr |
| 29 | IFN-α21 | Arg | Lys | Tyr | Phe | Gln | Arg | Ile | Thr | Leu | Tyr |
| 74 | IFN-α21 | Lys | Lys | Tyr | Phe | Gln | Arg | Ile | Thr | Leu | Tyr |

| SEQ ID NO: | Codon | 131 | 132 | 133 | 134 | 135 | 136 | 137 | 138 | 139 | 140 |
|---|---|---|---|---|---|---|---|---|---|---|---|
| 75 | Consensus | Leu | Thr | Glu | Lys | Lys | Tyr | Ser | Pro | Cys | Ala |
| 16 | IFN-α1b | Leu | Thr | Glu | Lys | Lys | Tyr | Ser | Pro | Cys | Ala |
| 17 | IFN-α1a | Leu | Thr | Glu | Lys | Lys | Tyr | Ser | Pro | Cys | Ala |
| 18 | IFN-α2a | Lys | Glu | Lys | Lys | Tyr | Ser | Pro | Cys | Ala | Trp |
| 19 | IFN-α2b | Lys | Glu | Lys | Lys | Tyr | Ser | Pro | Cys | Ala | Trp |
| 20 | IFN-α4a | Leu | Thr | Glu | Lys | Lys | Tyr | Ser | Pro | Cys | Ala |
| 21 | IFN-α4b | Leu | Thr | Glu | Lys | Lys | Tyr | Ser | Pro | Cys | Ala |
| 22 | IFN-α5 | Leu | Thr | Glu | Lys | Lys | Tyr | Ser | Pro | Cys | Ala |
| 23 | IFN-α6 | Leu | Thr | Glu | Lys | Lys | Tyr | Ser | Pro | Cys | Ala |
| 24 | IFN-α7 | Leu | Met | Glu | Lys | Lys | Tyr | Ser | Pro | Cys | Ala |
| 25 | IFN-α8 | Leu | Thr | Glu | Lys | Lys | Tyr | Ser | Ser | Cys | Ala |
| 26 | IFN-α10 | Leu | Ile | Glu | Arg | Lys | Tyr | Ser | Pro | Cys | Ala |
| 27 | IFN-α14 | Leu | Met | Glu | Lys | Lys | Tyr | Ser | Pro | Cys | Ala |
| 28 | IFN-α16 | Leu | Met | Gly | Lys | Lys | Tyr | Ser | Pro | Cys | Ala |
| 29 | IFN-α17 | Leu | Thr | Glu | Lys | Lys | Tyr | Ser | Pro | Cys | Ala |
| 74 | IFN-α21 | Leu | Thr | Glu | Lys | Lys | Tyr | Ser | Pro | Cys | Ala |

| SEQ ID NO: | Codon | 141 | 142 | 143 | 144 | 145 | 146 | 147 | 148 | 149 | 150 |
|---|---|---|---|---|---|---|---|---|---|---|---|
| 75 | Consensus | Trp | Glu | Val | Val | Arg | Ala | Glu | Ile | Met | Arg |
| 16 | IFN-α1b | Trp | Glu | Val | Val | Arg | Ala | Glu | Ile | Met | Arg |
| 17 | IFN-α1a | Trp | Glu | Val | Val | Arg | Ala | Glu | Ile | Met | Arg |
| 18 | IFN-α2a | Glu | Val | Val | Arg | Ala | Glu | Ile | Met | Arg | Ser |
| 19 | IFN-α2b | Glu | Val | Val | Arg | Ala | Glu | Ile | Met | Arg | Ser |
| 20 | IFN-α4a | Trp | Glu | Val | Val | Arg | Ala | Glu | Ile | Met | Arg |
| 21 | IFN-α4b | Trp | Glu | Val | Val | Arg | Ala | Glu | Ile | Met | Arg |
| 22 | IFN-α5 | Trp | Glu | Val | Val | Arg | Ala | Glu | Ile | Met | Arg |
| 23 | IFN-α6 | Trp | Glu | Val | Val | Arg | Ala | Glu | Ile | Met | Arg |
| 24 | IFN-α7 | Trp | Glu | Val | Val | Arg | Ala | Glu | Ile | Met | Arg |
| 25 | IFN-α8 | Trp | Glu | Val | Val | Arg | Ala | Glu | Ile | Met | Arg |
| 26 | IFN-α10 | Trp | Glu | Val | Val | Arg | Ala | Glu | Ile | Met | Arg |
| 27 | IFN-α14 | Trp | Glu | Val | Val | Arg | Ala | Glu | Ile | Met | Arg |
| 28 | IFN-α16 | Trp | Glu | Val | Val | Arg | Ala | Glu | Ile | Met | Arg |
| 29 | IFN-α17 | Trp | Glu | Val | Val | Arg | Ala | Glu | Ile | Met | Arg |
| 74 | IFN-α21 | Trp | Glu | Val | Val | Arg | Ala | Glu | Ile | Met | Arg |

| SEQ ID NO: | Codon | 151 | 152 |
|---|---|---|---|
| 75 | Consensus | Ser | Phe |
| 16 | IFN-α1b | Ser | Leu |
| 17 | IFN-α1a | Ser | Leu |
| 18 | IFN-α2a | Phe | |
| 19 | IFN-α2b | Phe | |
| 20 | IFN-α4a | Ser | Leu |
| 21 | IFN-α4b | Ser | Leu |
| 22 | IFN-α5 | Ser | Phe |
| 23 | IFN-α6 | Ser | Phe |
| 24 | IFN-α7 | Ser | Phe |
| 25 | IFN-α8 | Ser | Phe |
| 26 | IFN-α10 | Ser | Leu |
| 27 | IFN-α14 | Ser | Leu |
| 28 | IFN-α16 | Ser | Phe |
| 29 | IFN-α17 | Ser | Leu |
| 74 | IFN-α21 | Ser | Phe |

IFN-Lambda Sequences.

Table 5, below, depicts nucleotide sequences and sequence alignment and for IFN-lambda subtypes. Bold and underlined sequences represent unique nonconsensus codons.

TABLE 5

| SEQ ID NO: | | Codon | 1 | 2 | 3 | 4 | 5 | 6 | 7 | 8 | 9 | 10 |
|---|---|---|---|---|---|---|---|---|---|---|---|---|
| | | Position | 1 | 4 | 7 | 10 | 13 | 16 | 19 | 22 | 25 | 28 |
| 76 | IFN-l1 | | atg | gct | gca | gct | tgg | acc | gtg | gtg | ctg | gtg |
| 77 | IFN-l2 | | atg | act | ggg | gac | tgc | acg | cca | gtg | ctg | gtg |
| 78 | IFN-l3 | | atg | acc | ggg | gac | tgc | atg | cca | gtg | ctg | gtg |

TABLE 5-continued

| SEQ ID NO: | Codon Position | 11 31 | 12 34 | 13 37 | 14 40 | 15 43 | 16 46 | 17 49 | 18 52 | 19 55 | 20 58 |
|---|---|---|---|---|---|---|---|---|---|---|---|
| 76 | IFN-11 | act | ttg | gtg | cta | ggc | ttg | gcc | gtg | gca | ggc |
| 77 | IFN-12 | ctg | atg | gcc | gca | gtg | ctg | acc | gtg | act | gga |
| 78 | IFN-13 | ctg | atg | gcc | gca | gtg | ctg | acc | gtg | act | gga |

| SEQ ID NO: | Codon Position | 21 61 | 22 64 | 23 67 | 24 70 | 25 73 | 26 76 | 27 79 | 28 82 | 29 85 | 30 88 |
|---|---|---|---|---|---|---|---|---|---|---|---|
| 76 | IFN-11 | cct | gtc | ccc | act | tcc | aag | | | | ccc |
| 77 | IFN-12 | gca | gtt | cct | gtc | gcc | agg | ctc | cac | ggg | gct |
| 78 | IFN-13 | gca | gtt | cct | gtc | gcc | agg | ctc | cgc | ggg | gct |

| SEQ ID NO: | Codon Position | 31 91 | 32 94 | 33 97 | 34 100 | 35 103 | 36 106 | 37 109 | 38 112 | 39 115 | 40 118 |
|---|---|---|---|---|---|---|---|---|---|---|---|
| 76 | IFN-11 | acc | aca | act | ggg | aag | ggc | tgc | cac | att | ggc |
| 77 | IFN-12 | ctc | ccg | gat | gca | agg | ggc | tgc | cac | ata | gcc |
| 78 | IFN-13 | ctc | ccg | gat | gca | agg | ggc | tgc | cac | ata | gcc |

| SEQ ID NO: | Codon Position | 41 121 | 42 124 | 43 127 | 44 130 | 45 133 | 46 136 | 47 139 | 48 142 | 49 145 | 50 148 |
|---|---|---|---|---|---|---|---|---|---|---|---|
| 76 | IFN-11 | agg | ttc | aaa | tct | ctg | tca | cca | cag | gag | cta |
| 77 | IFN-12 | cag | ttc | aag | tcc | ctg | tct | cca | cag | gag | ctg |
| 78 | IFN-13 | cag | ttc | aag | tcc | ctg | tct | cca | cag | gag | ctg |

| SEQ ID NO: | Codon Position | 51 151 | 52 154 | 53 157 | 54 160 | 55 163 | 56 166 | 57 169 | 58 172 | 59 175 | 60 178 |
|---|---|---|---|---|---|---|---|---|---|---|---|
| 76 | IFN-11 | gcg | agc | ttc | aag | aag | gcc | agg | gac | gcc | ttg |
| 77 | IFN-12 | cag | gcc | ttt | aag | agg | gcc | aaa | gat | gcc | tta |
| 78 | IFN-13 | cag | gcc | ttt | aag | agg | gcc | aaa | gat | gcc | tta |

| SEQ ID NO: | Codon Position | 61 181 | 62 184 | 63 187 | 64 190 | 65 193 | 66 196 | 67 199 | 68 202 | 69 205 | 70 208 |
|---|---|---|---|---|---|---|---|---|---|---|---|
| 76 | IFN-11 | gaa | gag | tca | ctc | aag | ctg | aaa | aac | tgg | agt |
| 77 | IFN-12 | gaa | gag | tcg | ctt | ctg | ctg | aag | gac | tgc | agg |
| 78 | IFN-13 | gaa | gag | tcg | ctt | ctg | ctg | aag | gac | tgc | aag |

| SEQ ID NO: | Codon Position | 71 211 | 72 214 | 73 217 | 74 220 | 75 223 | 76 226 | 77 229 | 78 232 | 79 235 | 80 238 |
|---|---|---|---|---|---|---|---|---|---|---|---|
| 76 | IFN-11 | tgc | agc | tct | cct | gtc | ttc | ccc | ggg | aat | tgg |
| 77 | IFN-12 | tgc | cac | tcc | cgc | ctc | ttc | ccc | agg | acc | tgg |
| 78 | IFN-13 | tgc | cgc | tcc | cgc | ctc | ttc | ccc | agg | acc | tgg |

| SEQ ID NO: | Codon Position | 81 241 | 82 244 | 83 247 | 84 250 | 85 253 | 86 256 | 87 259 | 88 262 | 89 265 | 90 268 |
|---|---|---|---|---|---|---|---|---|---|---|---|
| 76 | IFN-11 | gac | ctg | agg | ctt | ctc | cag | gtg | agg | gag | cgc |
| 77 | IFN-12 | gac | ctg | agg | cag | ctg | cag | gtg | agg | gag | cgc |
| 78 | IFN-13 | gac | ctg | agg | cag | ctg | cag | gtg | agg | gag | cgc |

| SEQ ID NO: | Codon Position | 91 271 | 92 274 | 93 277 | 94 280 | 95 283 | 96 286 | 97 289 | 98 292 | 99 295 | 100 298 |
|---|---|---|---|---|---|---|---|---|---|---|---|
| 76 | IFN-11 | cct | gtg | gcc | ttg | gag | gct | gag | ctg | gcc | ctg |
| 77 | IFN-12 | ccc | atg | gct | ttg | gag | gct | gag | ctg | gcc | ctg |
| 78 | IFN-13 | ccc | gtg | gct | ttg | gag | gct | gag | ctg | gcc | ctg |

| SEQ ID NO: | Codon Position | 101 301 | 102 304 | 103 307 | 104 310 | 105 313 | 106 316 | 107 319 | 108 322 | 109 325 | 110 328 |
|---|---|---|---|---|---|---|---|---|---|---|---|
| 76 | IFN-11 | acg | ctg | aag | gtc | ctg | gag | gcc | gct | gct | |
| 77 | IFN-12 | acg | ctg | aag | gtt | ctg | gag | gcc | acc | gct | gac |
| 78 | IFN-13 | acg | ctg | aag | gtt | ctg | gag | gcc | acc | gct | gac |

| SEQ ID NO: | Codon Position | 111 331 | 112 334 | 113 337 | 114 340 | 115 343 | 116 346 | 117 349 | 118 352 | 119 355 | 120 358 |
|---|---|---|---|---|---|---|---|---|---|---|---|
| 76 | IFN-11 | | ggc | cca | gcc | ctg | gag | gac | gtc | cta | gac |
| 77 | IFN-12 | act | gac | cca | gcc | ctg | gtg | gac | gtc | ctt | gac |
| 78 | IFN-13 | act | gac | cca | gcc | ctg | ggg | gat | gtc | ctt | gac |

| SEQ ID NO: | Codon Position | 121 361 | 122 364 | 123 367 | 124 370 | 125 373 | 126 376 | 127 379 | 128 382 | 129 385 | 130 388 |
|---|---|---|---|---|---|---|---|---|---|---|---|
| 76 | IFN-11 | cag | ccc | ctt | cac | acc | ctg | cac | cac | atc | ctc |
| 77 | IFN-12 | cag | ccc | ctt | cac | acc | ctg | cac | cat | atc | ctc |
| 78 | IFN-13 | cag | ccc | ctt | cac | acc | ctg | cac | cat | atc | ctc |

| SEQ ID NO: | Codon Position | 131 391 | 132 394 | 133 397 | 134 400 | 135 403 | 136 406 | 137 409 | 138 412 | 139 415 | 140 418 |
|---|---|---|---|---|---|---|---|---|---|---|---|
| 76 | IFN-11 | tcc | cag | ctc | cag | gcc | tgt | atc | cag | cct | cag |
| 77 | IFN-12 | tcc | cag | ttc | cgg | gcc | tgt | atc | cag | cct | cag |
| 78 | IFN-13 | tcc | cag | ctc | cgg | gcc | tgt | atc | cag | cct | cag |

| SEQ ID NO: | Codon Position | 141 421 | 142 424 | 143 427 | 144 430 | 145 433 | 146 436 | 147 439 | 148 442 | 149 445 | 150 448 |
|---|---|---|---|---|---|---|---|---|---|---|---|
| 76 | IFN-11 | ccc | aca | gca | ggg | ccc | agg | ccc | cgg | ggc | cgc |
| 77 | IFN-12 | ccc | acg | gca | ggg | ccc | agg | acc | cgg | ggc | cgc |
| 78 | IFN-13 | ccc | acg | gca | ggg | ccc | agg | acc | cgg | ggc | cgc |

| SEQ ID NO: | Codon Position | 151 451 | 152 454 | 153 457 | 154 460 | 155 463 | 156 466 | 157 469 | 158 472 | 159 475 | 160 478 |
|---|---|---|---|---|---|---|---|---|---|---|---|
| 76 | IFN-11 | ctc | cac | cac | tgg | ctg | cac | cgg | ctc | cag | gag |
| 77 | IFN-12 | ctc | cac | cat | tgg | ctg | tac | cgg | ctc | cag | gag |
| 78 | IFN-13 | ctc | cac | cat | tgg | ctg | cac | cgg | ctc | cag | gag |

| SEQ ID NO: | Codon Position | 161 481 | 162 484 | 163 487 | 164 490 | 165 493 | 166 496 | 167 499 | 168 502 | 169 505 | 170 508 |
|---|---|---|---|---|---|---|---|---|---|---|---|
| 76 | IFN-11 | gcc | ccc | aaa | aag | gag | tcc | gct | ggc | tgc | ctg |
| 77 | IFN-12 | gcc | cca | aaa | aag | gag | tcc | cct | ggc | tgc | ctc |
| 78 | IFN-13 | gcc | cca | aaa | aag | gag | tcc | cct | ggc | tgc | ctc |

| SEQ ID NO: | Codon Position | 171 511 | 172 514 | 173 | 174 | 175 | 176 | 177 | 178 | 179 | 180 |
|---|---|---|---|---|---|---|---|---|---|---|---|
| 76 | IFN-11 | gag | gca | tct | gtc | acc | ttc | aac | ctc | ttc | cgc |
| 77 | IFN-12 | gag | gcc | tct | gtc | acc | ttc | aac | ctc | ttc | cgc |
| 78 | IFN-13 | gag | gcc | tct | gtc | acc | ttc | aac | ctc | ttc | cgc |

| SEQ ID NO: | Codon Position | 181 | 182 | 183 | 184 | 185 | 186 | 187 | 188 | 189 | 190 |
|---|---|---|---|---|---|---|---|---|---|---|---|
| 76 | IFN-11 | ctc | ctc | acg | cga | gac | ctc | aaa | tat | gtg | gcc |
| 77 | IFN-12 | ctc | ctc | acg | cga | gac | ctg | aat | tgt | gtt | gcc |
| 78 | IFN-13 | ctc | ctc | acg | cga | gac | ctg | aat | tgt | gtt | gcc |

| SEQ ID NO: | Codon Position | 191 | 192 | 193 | 194 | 195 | 196 | 197 | 198 | 199 | 200 |
|---|---|---|---|---|---|---|---|---|---|---|---|
| 76 | IFN-11 | gat | ggg | aac | ctg | tgt | ctg | aga | acg | tca | acc |
| 77 | IFN-12 | agt | ggg | gac | ctg | tgt | gtc | tga | ccc | tcc | cac |
| 78 | IFN-13 | agc | ggg | gac | ctg | tgt | gtc | tga | | | |

| SEQ ID NO: | Codon Position | 201 | 202 | 203 | 204 | 205 | 206 | 207 | 208 | 209 | 210 |
|---|---|---|---|---|---|---|---|---|---|---|---|
| 76 | IFN-11 | cac | cct | gag | tcc | acc | tga | cac | ccc | aca | cct |
| 77 | IFN-12 | cag | tca | tgc | aac | ctg | aga | ttt | tat | tta | taa |
| 78 | IFN-13 | | | | | | | | | | |

TABLE 5-continued

| SEQ ID NO: | Codon Position | 211 | 212 | 213 | 214 | 215 | 216 | 217 | 218 | 219 | 220 |
|---|---|---|---|---|---|---|---|---|---|---|---|
| 76 | IFN-11 | tat | tta | tgc | gct | gag | ccc | tac | | | |
| 77 | IFN-12 | att | agc | cac | ttg | tct | taa | ttt | att | gcc | acc |
| 78 | IFN-13 | | | | | | | | | | |

| SEQ ID NO: | Codon Position | 221 | 222 | 223 |
|---|---|---|---|---|
| 76 | IFN-11 | | | |
| 77 | IFN-12 | cag | tcg | cta |
| 78 | IFN-13 | | | |

Primer/Probe Set Design and Synthesis

Sequences for the genotypes and the allotypic variants were loaded into Beacon Designer (Versions 5-7.2, Premier Biosoft, Palo Alto, Calif.) and interrogated for MB and LNA primer/probe sets to target unique sequences in each subtype. Each subtype generated an LNA and/or MB primer/probe set. When both types of sets were generated, both were synthesized and tested to determine which exhibited better performance. Following these initial screens, secondary experiments were performed to determine selectivity to the targeted subtype. Oligo sequences were then edited to optimize their sensitivity/selectivity profiles. Oligo sequences were also edited to account for PCR conditions, and specifically to obtain primers for each IFN-alpha subtype that could perform well under the same PCR conditions and thus be used in an IFN-alpha subtype panel assay. In some cases, the primer(s) or probe sequence was shifted 5' to 3' to the unique codon sequence to enhance specificity. For one set, in which non-specific binding occurred, primer/probe specificity was enhanced with an LNA oligomer inhibitor to block primer or probe annealing to the errantly amplified subtype(s). Incorporation of this blocking oligo into the reaction mix for this specific subtype resulted in selective binding of the LNA to the undesired cDNA, effectively blocking its ability to be amplified by the oligo set. This resulted in the desired selectivity for the target subtype.

After the desired target sequences were identified, further studies were conducted comparing their overall efficiencies by designing and testing molecular beacons and LNA oligos in a side-by-side comparison. This included titration of target sequences, oligos and reaction components to optimize the sensitivity to the target subtype, while creating the largest separation (cycle count values) from the other subtypes to result in optimal selectivity. Sequences for primers, probes, and LNA inhibitors for IFN-alpha subtypes are shown in FIG. 1.

Primers were synthesized on a MerMade 6 (Bioautomation Corp, Plano Tex.) synthesizer. MB probes were synthesized on an 394 DNA/RNA synthesizer (Applied Biosciences, Foster City, Calif.) and labeled with 6-carboxyfluorescein (FAM) as the 5' reporter, and 6-carboxytetramethylrhodamine (TAMRA) as the 3' quencher. Primers and FAM/TAMRA modified MB were synthesized at the Facility for Biotechnology Research at the Center for Biologics Evaluation and Research in the U.S. Food and Drug Administration. LNA probes and inhibitor oligomers were synthesized by either Sigma Proligo (St. Louis, Mo.) or Eurogentec North America (San Diego, Calif.).

Template for Testing Primer/Probe Sets

DNA for each IFN-alpha gene template excised from its bacterial plasmid expression vector was purified by Pestka Biomedical Laboratories, Inc. (Piscataway, N.J.) and quantified using the Quant-IT PicoGreen dsDNA Assay Kit (Invitrogen, Carlsbad, Calif.).

In vitro synthesized RNA for each alpha subtype was provided by Pestka Biomedical Laboratories, Inc. Four cell lines were transfected with 2.5 micrograms of either control empty plasmid or with expression plasmids, each containing the coding sequence for an IFN-alpha subtype. Total cellular RNA was isolated using RNAeasy spin columns (Qiagen, Germantown, Md.) and chromosomal DNA was digested with DNAse prior to reverse transcription of RNA.

Generation of First Strand cDNA

First-strand cDNA was generated from either in vitro transcribed RNA or total RNA from transfected cells using Superscript III (Invitrogen) according to the manufacturer instructions for a final reaction volume of 20 microliters (µl).

Real-Time Polymerase Chain Reaction (RT-PCR)

Purified DNA template was used to test primer/probe set sensitivity. TaqMan Fast Universal PCR Master Mix (Applied Biosystems) was used to achieve a final reaction volume of 20 µl. Optimal primer concentrations were determined by 5×5 checkerboard assays varying forward and reverse primer concentrations from 100 nM to 500 nM with probe concentration constant at 100 nM. Next, optimal probe concentration was determined by titration from 250 nM to 15.6 nM, under fixed optimal primer concentration.

RT-PCR was performed using an Applied Biosystems 7900HT Fast Real Time PCR System. The PCR protocol consisted of: initiation at 1 cycle at 50° C. for two minute and 1 cycle at 95° C. for ten minutes, followed by amplification for 40 cycles, each consisting of 15 seconds of denaturation (95° C.) and 1 minute of extension. Extension temperature for each primer/probe set was initially guided by Beacon Designer before testing for a common temperature at which all primer/probe sets could be simultaneously used.

Results

Primer/Probe Sequence Design and Testing

MB primer/probe sets were generated for all subtypes, and LNA primer/probe sets for all but IFN-alpha7 and IFN-alpha21. After determining optimal primer/probe concentration, each set was tested against purified serial 10-fold IFN-alpha subtype template dilution series in triplicate with a starting concentration of 10.0 pM template (FIG. 2). After plotting the template concentration vs. Ct. value (PCR cycle count by which the fluorescence signal of the target sequence rises above threshold value), the PCR sensitivity was determined by calculating the number of molecules of template in the starting reaction that gave a reliable signal over background. In some cases, quantitative sensitivity (i.e. the number of molecules present in the starting reaction) was one or two dilutions below qualitative sensitivity (i.e. presence or absence of template). PCR sensitivity for IFN-alpha primers was typically between 1-10 molecules of template per reaction (FIG. 2).

PCR efficiency (perfect efficiency=2.0 amplicons/template/cycle) was determined by the formula:

$$\text{Efficiency} = [10^{(-1/slope)}]$$

FIG. 2 shows the efficiency calculations for each of the IFN-alpha subtypes' PCR reactions. In general, the LNA sets were more sensitive and efficient than the MB sets.

Figure 3:
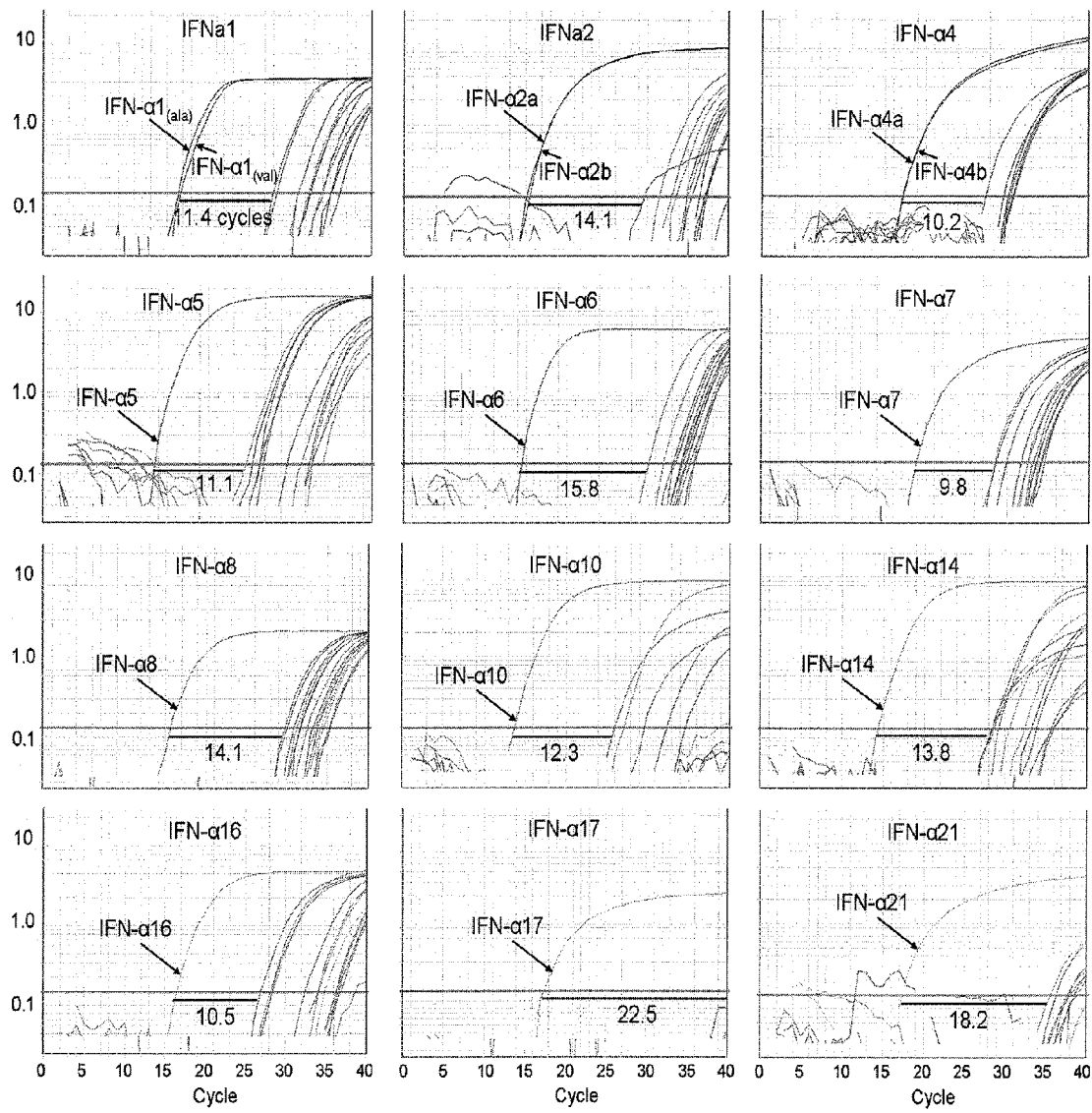
FIG. 3 is a panel of graphs depicting template dilutions for each IFN-alpha primer/probe set for measuring specificity. The interval (in cycles) between amplification of specific template and highest non-specific signal is indicated beneath the horizontal bar.

Specificity was determined by testing the primer/probe sets with 1.0 pM of each of the IFN-alpha subtype cDNAs (FIG. 3). A primer/probe set is considered specific if the target sequence and non-specific sequences were separated by at least nine cycles (i.e. 512-fold difference in signal). If specificity was inadequate, the primer/probe set was redesigned, or LNA oligomer inhibitors complementary to the non-specific target sequence were designed. The template specific to its primer/probe set consistently amplified earliest. The IFN-alpha subtypes' PCR reactions typically had about a 10-cycle (1,000-fold) discrimination between target and non-target isoforms (FIG. 3).

Figure 4:
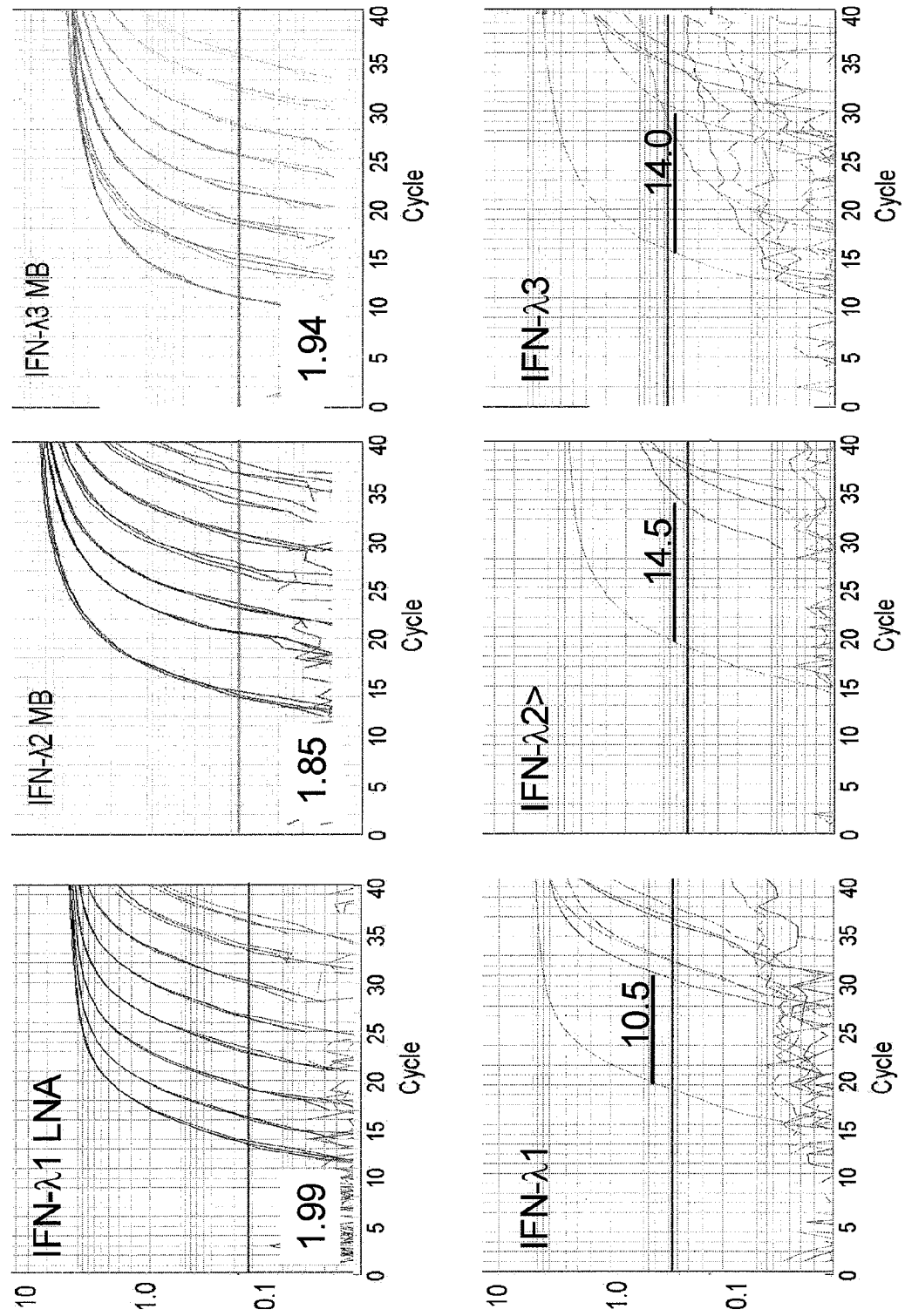
FIG. 4 is a panel of graphs depicting template dilutions for IFN-lambda subtype primer/probe sets for measuring efficiency (top row) and specificity (bottom row). Efficiency of each primer/probe set shown in the lower left hand corner of the graph. The interval (in cycles) between amplification of specific template and highest non-specific signal is indicated beneath the horizontal bar. Specificity was tested against all other IFN-alpha subtypes (except IFN-alpha4b), all other rIFN-lambda subtypes, IFN-beta and IFN-gamma.
Figure 5:
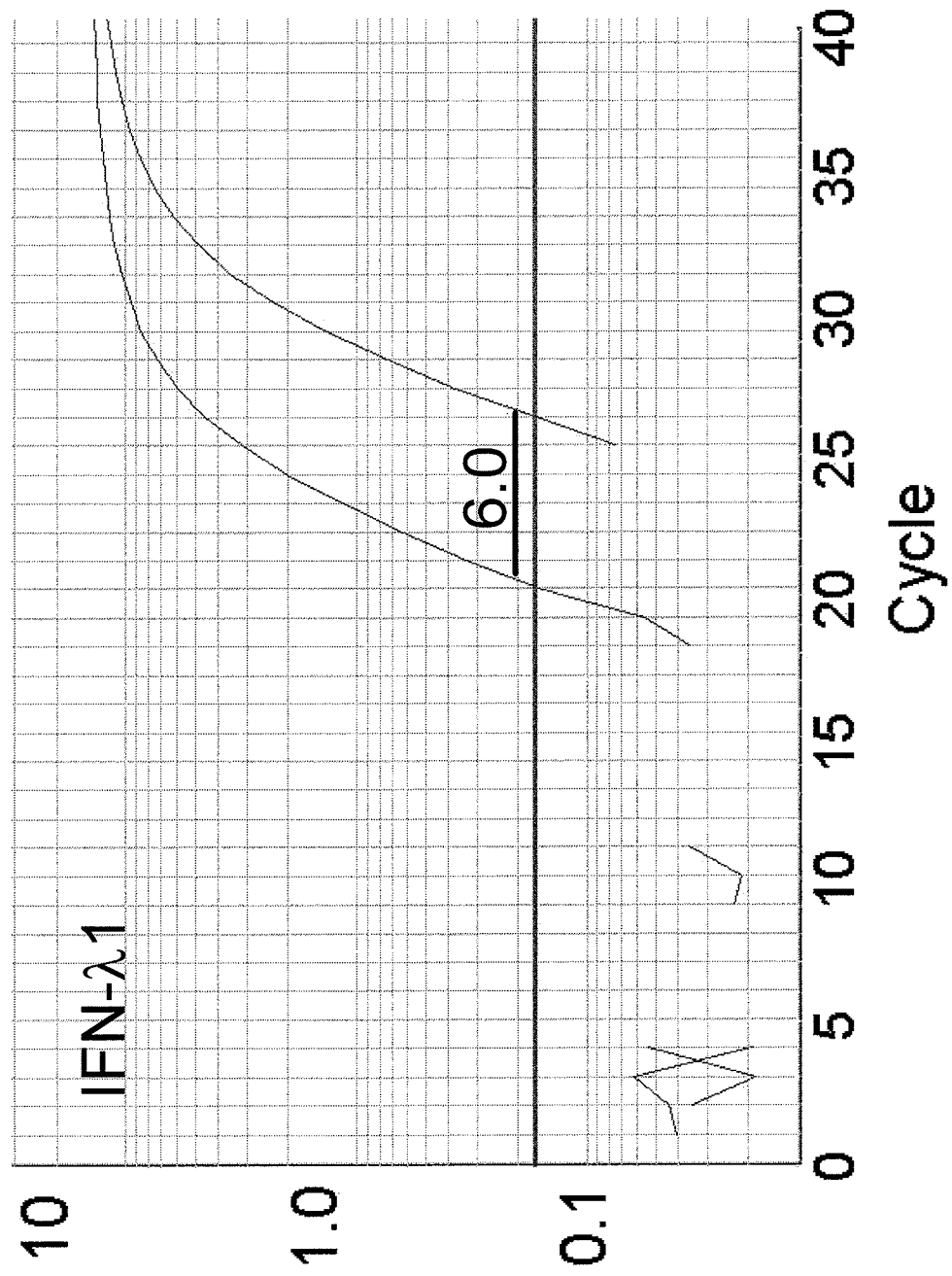
FIG. 5 is a graph depicting the specificity of the primer/probe set for IFN-lambda1. Specificity was tested against IFN-alpha4b.

Sensitivity, specificity and efficiency were determined for IFN-lambda subtype primer sets as described above for IFN-alpha subtype primer sets. Efficiency of each IFN-lambda primer/probe set is shown in the lower left hand corner of the graphs on the top row of FIG. 4. Specificity is shown in the bottom row of graphs in FIG. 4. In each graph, the curve to the left represents amplification of the IFN-lambda template specific to the primer/probe set, and the bar and number indicate the number of cycles of the most non-specifically amplified template. The IFN-alpha4 template tested in these experiments was the allelic variant IFN-alpha4b. As shown in FIG. 4, the IFN-lambda1 primer/probe set was less specific for IFN-alpha4b than any other tested template in this experiment. A subsequent experiment, however, demonstrated high specificity for IFN-lambda1 even in the presence of IFN-alpha4b template (data not shown). Both templates were amplified with the primer/probe set for detecting IFN-lambda1 at starting concentration of 10 fM for each template. FIG. 5 shows amplification of IFN-lambda1 in the curve to the left. The bar and number indicate the separation between the non-specifically amplified IFN-alpha4b template and the specifically amplified IFN-lambda1.

Sensitivity and specificity of each primer/probe set was determined at its "optimal" temperature, as determined by Beacon Designer software. Specificity and sensitivity of all sets were tested at a series of PCR extension temperatures ranging from 52° C. to 59.5° C. to identify a single temperature at which the complete set of subtypes could be measured concurrently on one plate. Table 6 compares sensitivity and specificity at "optimal" temperature to 58.5° C., and demonstrates that sensitivity and specificity typically improved at a PCR extension temperature of 58.5° C., as compared to the "optimal" temperature as determined by the software. Therefore, 58.5° C. was designated as a common temperature for simultaneous testing of all alpha primer/probe sets.

Figure 6:
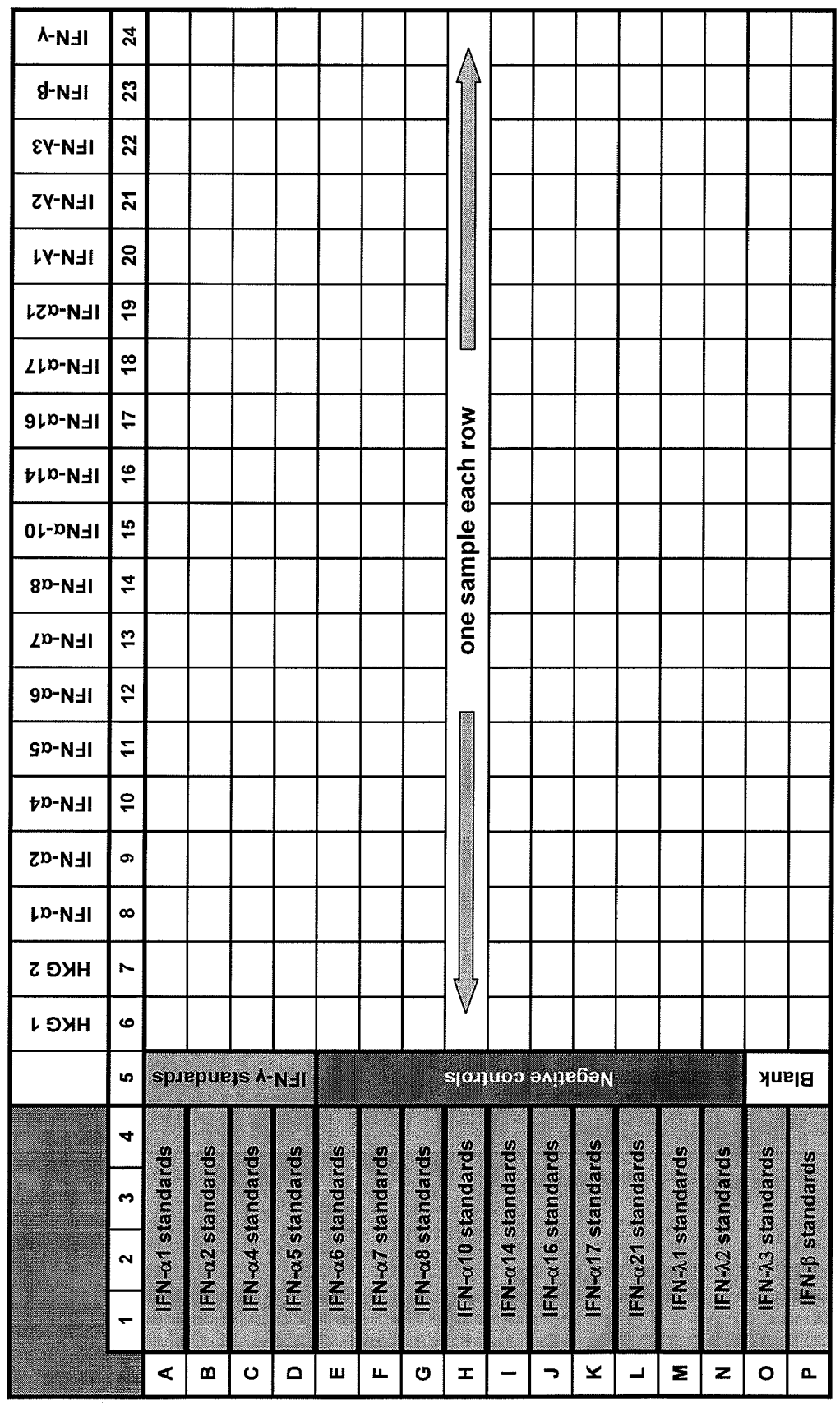
FIG. 6 depicts an exemplary physical layout of a 384-well plate format of an IFN-alpha and IFN-lambda RT-PCR detection kit. The wells in columns 1-4 represent fixed template concentrations while the designated wells in column 5 serve as IFN-lambda standards and no-template controls from which standard curves will be derived. The concentrations of the standards vary among subtypes due to differences in quantitative concentration range. Each plate holds sixteen samples, one sample per row, in rows through P.

An exemplary layout of a 384-well reaction plate for analysis of the subtypes of IFN-alpha and lambda is shown in FIG. 6.

Figure 7:
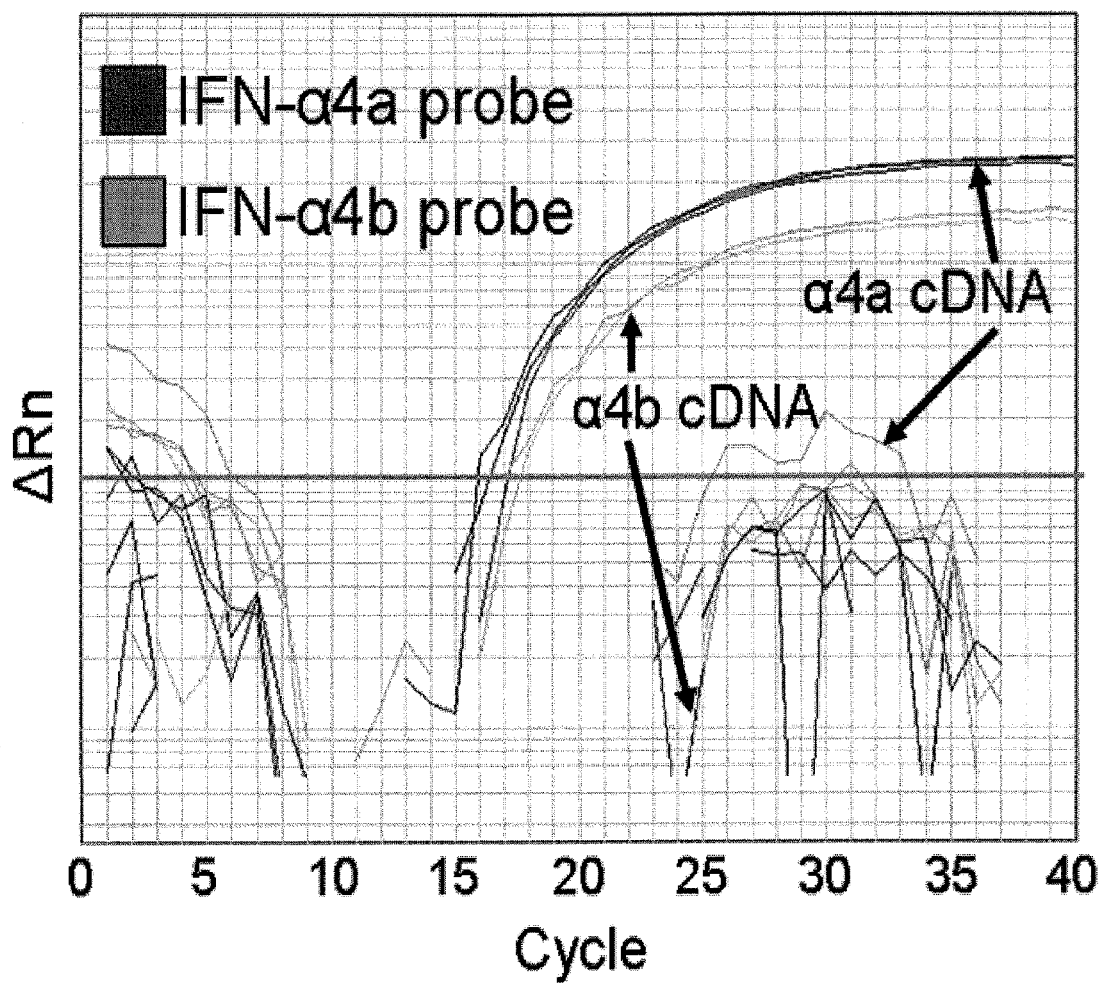
FIG. 7 is a graph showing that the IFN-alpha4a primer/probe set amplifies IFN-alpha4a cDNA but not IFN-alpha4b cDNA, and that the IFN-a4b primer/probe set amplifies IFN-alpha4b cDNA but not IFN-alpha4a cDNA.

MB primer/probe sets were designed and tested to discriminate between the allotypic variants of IFN-alpha4 (FIG. 7). The IFN-alpha4a primer/probe set amplified IFN-alpha4a cDNA but not IFN-alpha4b cDNA. Conversely, the IFN-a4b primer/probe set amplifies IFN-alpha4b cDNA but not IFN-alpha4a cDNA. The probes for the allelic variants of IFN-alpha4 are MB, while the probe that detects either variant of IFN-alpha4 is an LNA. Thus, the IFN-alpha4a set successfully detected IFN-alpha4a but not IFN-alpha4b, and the IFN-alpha4b set conversely detected IFN-alpha4b but not IFN-alpha4a.

Synthesis of cDNA from In Vitro Transcribed and Total Cellular RNA

Because secondary structure in the 3' untranslated region of the IFN-alpha messenger RNA transcripts may impair reverse transcription, reverse transcription reactions were carried out at either 50° C. or 55° C., using transfected cell line RNA as the input. Although the higher reaction temperature was expected to resolve secondary structures, interrogation of the resulting cDNA using the its IFN-alpha primer/probe set demonstrated that RT-PCR amplification of IFN-alpha subtypes was slightly earlier and more consistent when the reverse transcription reaction was 50° C. (data not shown). Thus, a temperature of 50° C. was designated as the reverse transcription incubation temperature.

Figure 8:
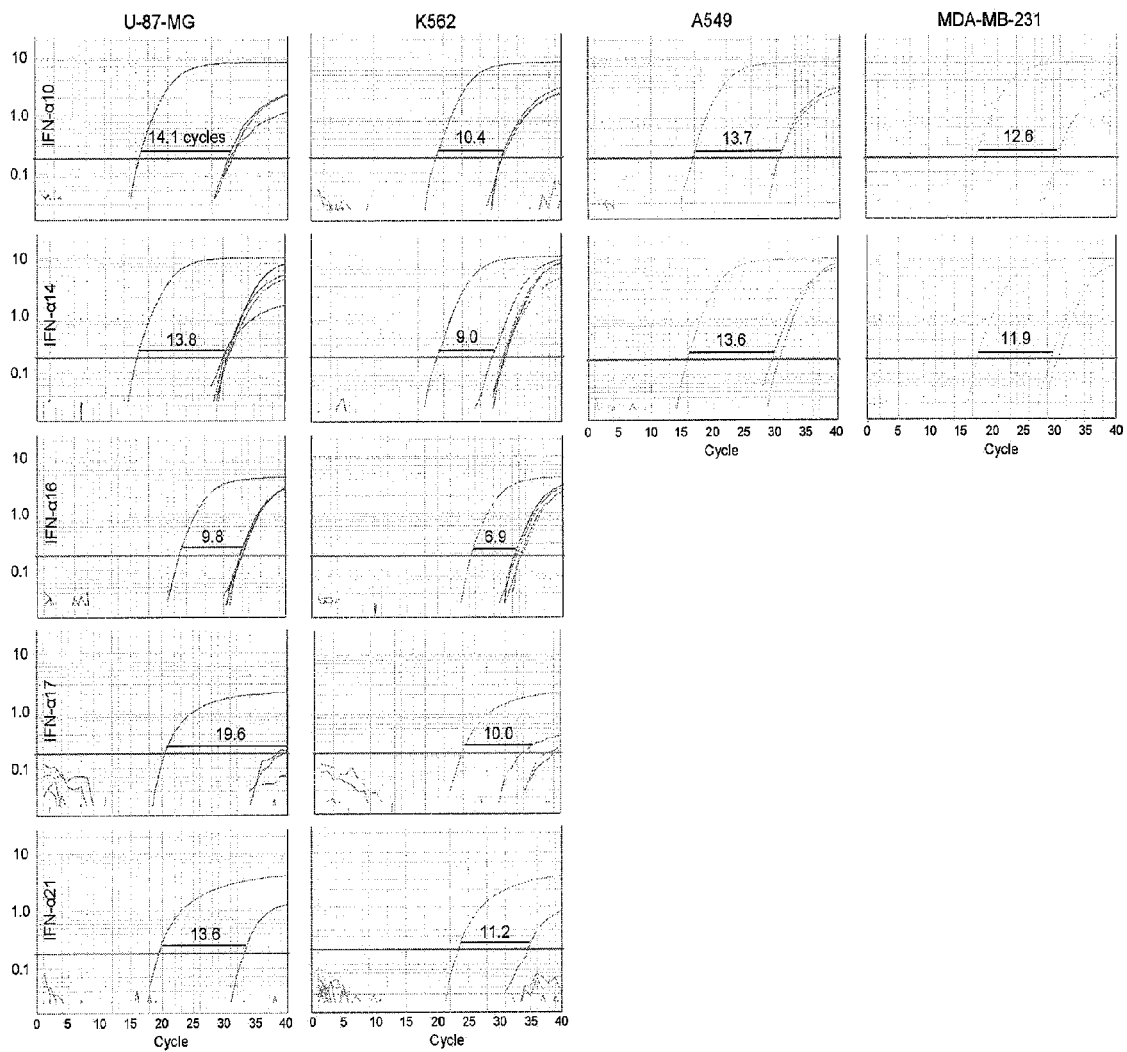
FIG. 8 shows a series of graphs showing the specificity of IFN-alpha primer/probe sets towards total cellular RNA. The interval (in cycles) between amplification of specific template and highest non-specific signal is indicated beneath the horizontal bar.

Finally, the specificity of IFN-alpha primer/probe sets was tested on transfected cell line RNA samples. Four cell lines (indicated across the top of the figure) were transfected with a plasmid encoding a single IFN-alpha subtype (indicated across the left vertical axis). Thus, the corresponding IFN-alpha primer/probe set should generate signal while the other sets would not. Total RNA was extracted from the cell lines. The cell sample expressing the cDNA corresponding to the IFN-alpha primer/probe set consistently amplified earliest. The interval (in cycles) between amplification of specific template and highest non-specific signal is indicated beneath the horizontal bar. Thus, FIG. 8 shows that specificity was maintained when testing the primer/probe sets against reverse-transcribed mRNA from transfected cell lines.

TABLE 6

| | | Optimal temperature | | | Common temp (58.5° C.) | | |
|---|---|---|---|---|---|---|---|
| | | Sensitivity | | | Sensitivity | | |
| Gene | Opt. Temp (° C.) | Qual | Quant | Efficiency | Qual | Quant | Efficiency |
| IFN-α1a (α1ala cDNA) | 55.5 | 2 | 2 | 1.99 | 15 | 15 | 1.92 |
| IFN-α1b (α1val cDNA) | 55.5 | 2 | 2 | | 2 | 2 | 2.00 |
| IFN-α2 | 53.1 | 15 | 15 | 1.99 | 2 | 2 | 1.97 |
| IFN-α4 (α4a cDNA) | 55.5 | 150 | 150 | 1.93 | 150 | 150 | 2.00 |
| IFN-α4 (α4b cDNA) | 55.5 | 150 | 150 | 1.92 | 150 | 150 | 1.93 |
| IFN-α5 | 53.7 | 1 | 2 | 1.98 | 1 | 2 | 2.00 |
| IFN-α6 | 52.2 | 1 | 2 | 1.99 | 2 | 2 | 1.98 |
| IFN-α7 | 54.2 | 2 | 2 | 2.00 | 15 | 150 | 2.00 |
| IFN-α8 | 55.4 | 15 | 15 | 1.87 | 2 | 2 | 1.96 |
| IFN-α10 | 54.9 | 2 | 2 | 2.00 | 1 | 2 | 2.00 |
| IFN-α14 | 54.1 | 15 | 15 | 1.92 | 1 | 2 | 2.00 |
| IFN-α16 | 52.3 | 15 | 15 | 1.89 | 1 | 2 | 2.00 |
| IFN-α17 | 55.6 | 15 | 15 | 1.86 | 2 | 2 | 1.99 |
| IFN-α21 | 53.6 | 15 | 15 | 1.94 | 1 | 2 | 2.00 |

Example 2

Differential Expression of IFNs by Primary Monocytes, B Cells, Dendritic Cells (DC) and Monocyte Derived DC (MDDC) and Macrophages (MDM)

To test whether expression of IFN subtypes varied among different cell types, the primers of the invention were used to determine expression patterns of IFN-alpha, IFN-lambda, IFN-beta and IFN-gamma in response to ligands of TLR 3 (poly I:C), 4 (LPS), 7 (imiquimod) and 9 (CpG). LPS (*E. coli* O111:B4), imiquimod, and poly I:C were purchased from EMD Chemicals (Gibbstown, N.J.). CpG types D35, K, and C, and control D35 GpC oligonucleotides were synthesized by the Food and Drug Administration Center for Biologics Evaluation and Research Facility for Biotechnology Resources. For both the D35 CpG and control GpC, the two bases at the 5' and 3' ends had nuclease-resistant phosphorothioate linkages.

Human peripheral blood monocytes, myeloid DC (mDC), plasmacytoid DC (pDC), and B cells were isolated. Elutriated monocytes and lymphocytes were obtained from the NIH Clinical Center Department of Transfusion Medicine (Bethesda, Md.) and the preparation was subjected to Ficoll-Hypaque (Sigma-Aldrich, St. Louis, Mo.) density centrifugation. Monocytes, mDC and pDC were purified with magnetic beads specific for CD14, CD1c, and CD303, respectively using an AutoMACS magnetic cell sorter (Miltenyi Biotec, Auburn, Calif.). B cells were purified from elutriated lymphocytes by negative selection using bi-functional antibodies (RosetteSep, StemCell Technologies, Vancouver, BC) and Ficoll-Hypaque density centrifugation. Purity of primary cells was verified by flow cytometry.

Monocytes were cultured for seven days in 100 ng/mL M-CSF (eBioscience, San Diego, Calif.) to generate monocyte-derived macrophages (MDM), and 1000 U/mL of IL-4 (Peprotech, Rocky Hill, N.J.), 800 U/mL of GM-CSF (Amgen, Thousand Oaks, Calif.) and 0.05 mM β-mercaptoethanol (Sigma Aldrich) to generate monocyte-derived dendritic cells (MDDC). Cells were cultured in RPMI 1640 medium (Gibco, Carlsbad, Calif.), 10% FBS (Hyclone, Logan Utah), and 20 μg/mL gentamicin (Invitrogen, Carlsbad, Calif.).

Primary and derived cells were cultured at $1 \times 10^6$ cells/mL and stimulated with TLR ligands at the following concentrations: 25 ug/ml Poly I:C, 10 ng/ml LPS; 6.5 ug/ml CpG A; and 10 uM Imiquimod. Stimulation lasted for 1, 4 or 24 hours and supernatants were harvested for measurement of secreted products, and cells were lysed for RNA purification and cDNA synthesis. The PCR reaction conditions were: Stage 1: 50° C. for two minutes; Stage 2: 95° C. for three minutes; Stage 3: 40 repeats of 95° C. for 15 seconds followed by 59° C. for one minute.

Figures 9A, 9B, 9C:
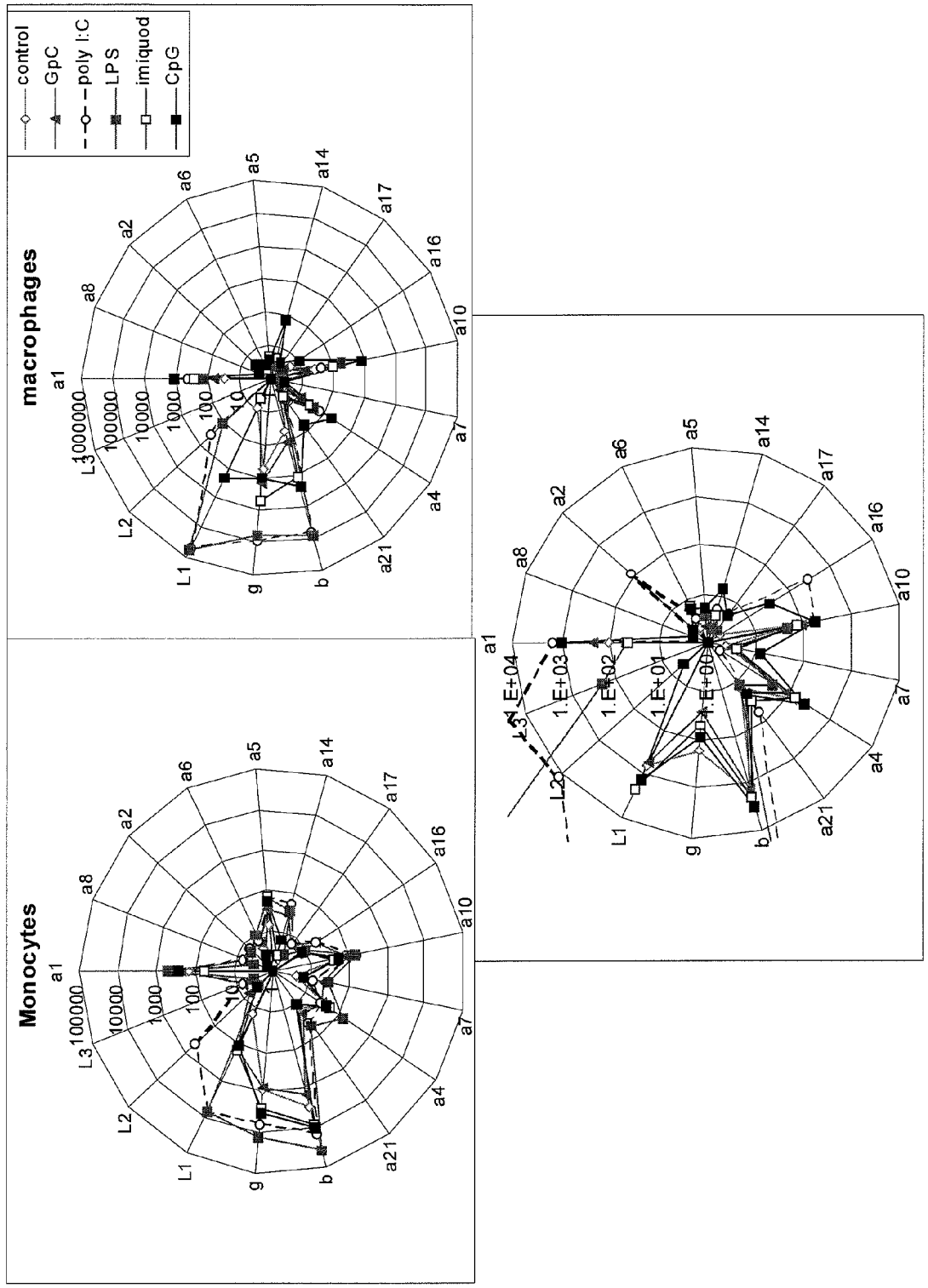
FIG. 9 is a series of graphs depicting expression profiles of various IFN-alpha, IFN-beta, IFN-gamma, and IFN-lambda subtypes in monocytes (FIG. 9A), monocyte-derived macrophages (MDM) (FIG. 9B), monocyte-derived dendritic cells (MDDC) (FIG. 9C), plasmacytoid dendritic cells (pDC) (FIG. 9D), myeloid dendritic cells (mDC) (FIG. 9E) and human B cells (FIG. 9F).

Patterns of expression by monocytes, MDM and MDDC were similar but not identical in quality, but quantitatively different (MDDC>monocyte=MDM) (FIG. 9A-C). In response to poly I:C (TLR3) and LPS (TLR4), these three cell types expressed high levels of IFN-b, IFN-g, IFN-l1, and to a lesser extent, IFN-l2 and IFN-a1. In addition, mDC expressed most IFN-a subtypes in response to TLR7 and TLR9 ligands (imiquimod and CpG, respectively) although responses to these ligands by mDC varied with donor (FIG. 9E). pDC also expressed most IFN (with variation among donors) in response to imiquimod and CpG, but at much higher levels than mDC (FIG. 9E).

Figure 9F:
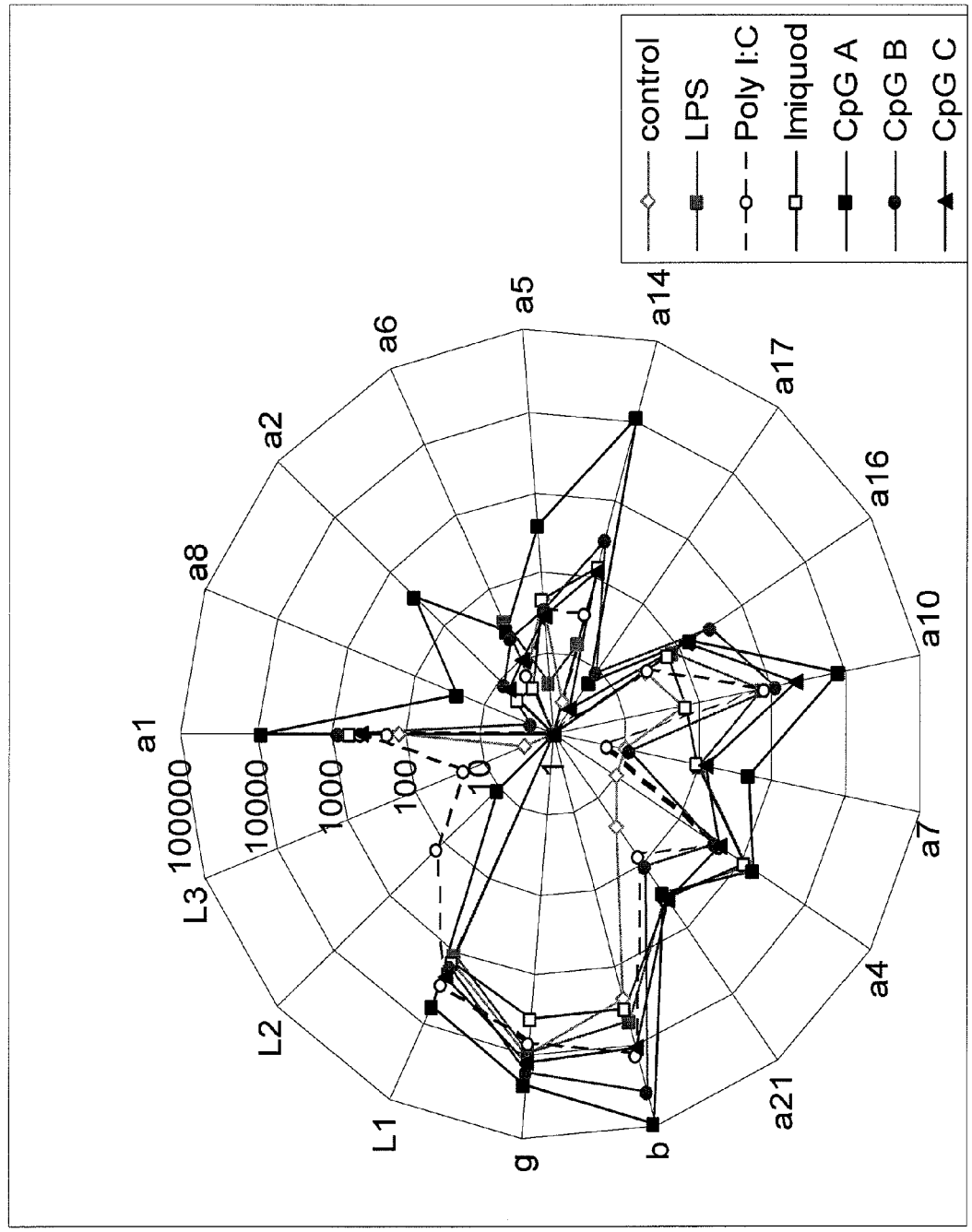

The profile of the B cells differed from that in the other cells: B cells expressed low levels of IFN-alpha4, and also IFN-alpha 5, -alpha 7, -alpha10, -alpha14, and -lambda1 (FIG. 9F). As a group, expression of these IFN subtypes was consistent, but expression patterns varied among the donors.

These data indicate that expression patterns of Types I, II, and III IFN are both stimuli (e.g., ligand) and cell-type specific. More specifically, among the cell types tested, the pattern of expression of IFN appears to be ligand dependent, while the levels of expression appear to be cell dependent. No one IFN-a or -l subtype appears to be dominant. These results suggest that individual subtypes and/or combinations of subtypes have unique roles in the innate immune response.

Example 3

In Situ Expression Profiles of IFN-Subtypes in Human Tonsil

To investigate whether IFN subtypes were differentially in different locations within the same organ, different anatomical locations of human tonsil were assessed for IFN-subtype expression using the primer/probe/inhibitor sets shown in FIG. 1 and the plate shown in FIG. 3. PCR reaction conditions were: Stage 1: 50° C. for two minutes; Stage 2: 95° C. for three minutes; Stage 3: 40 repeats of 95° C. for 15 seconds followed by 59° C. for one minute.

Figure 10:
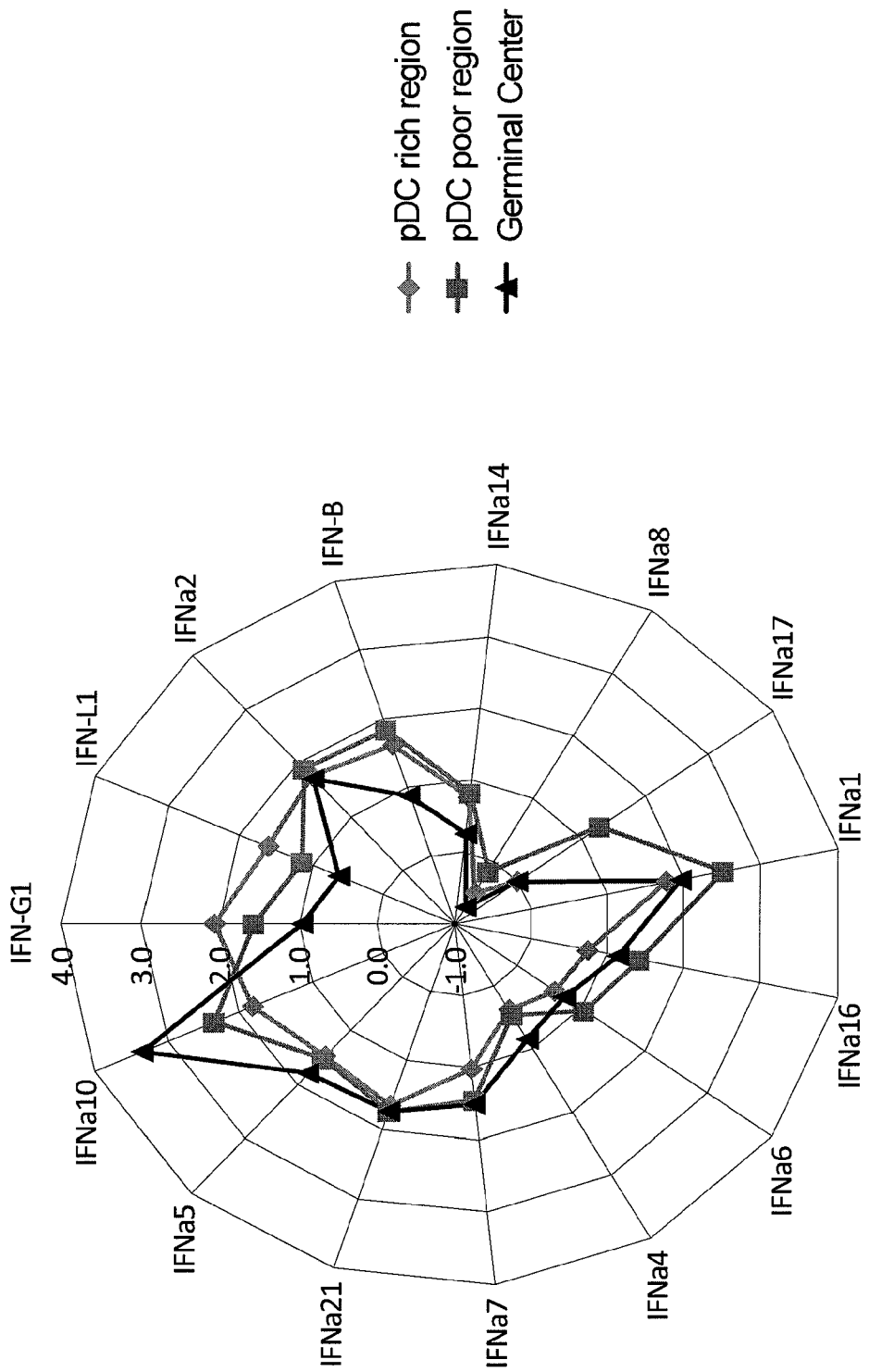
FIG. 10 is a graph depicting the expression profiles (log 10 of linear dCt) of various IFN-alpha, -beta, -gamma, and lambda subtypes in three sections of tonsil tissue: germinal center B cells (GBC), T cell zones rich in plasmacytoid dendritic cells, and T cell zones poor in plasmacytoid dendritic cells.

Tonsil is a readily available mucosal immune organ with ongoing innate and adaptive responses to challenges from organisms that have access to the oral cavity through the mouth and nose. Laser capture microdissection (LCM) was used to remove three anatomical areas from 10 μm thick sections of human tonsil: germinal center and T cell zones rich in pDC (pDC rich) and poor in pDC (pDC poor). Because the pDC are known to express the highest levels of IFN-alpha, it was predicted that the most expression of IFN would be in the pDC rich region. However, this was not the case (FIG. 10). Although the highest levels of IFN-gamma and IFN-lambda1 were in the pDC rich region, IFN-alpha1 and -alpha17 were expressed at the highest levels in the pDC poor area, and IFN-alpha10 was expressed most highly in the germinal center B cells (GCB). Because microarray data suggest that the pDC poor region is associated with regulation of T cell function, these data suggest a similar function for IFN-alpha1 and alpha17. In addition, these data suggest that there are tissue and zonal differences in IFN subtype expression patterns.

All publications and patent applications in this specification are indicative of the level of ordinary skill in the art and are incorporated herein by reference in their entireties.

The various embodiments described above are provided by way of illustration only and should not be construed to limit the invention. Those skilled in the art will readily recognize various modifications and changes that may be made to the present invention without following the example embodiments and applications illustrated and described herein, and without departing from the true spirit and scope of the present invention without following the example embodiments and applications illustrated and described herein, and without departing from the true spirit and scope of the present invention, which is set forth in the following claims.

We claim:

1. A method of categorizing an immune response of an individual according to levels of a set of at least two IFN subtype transcripts, comprising the steps of:
    obtaining a sample from the individual;
    purifying RNA from the sample obtained from the individual and performing reverse transcription on the RNA from the sample to obtain cDNA;
    contacting the cDNA with a composition comprising at least a first oligonucleotide pair and a second oligonucleotide pair, wherein each oligonucleotide pair is capable of specifically binding to a single subtype of IFN transcript, wherein the first oligonucleotide pair is selected from the list of oligonucleotide pairs consisting of: SEQ ID NO: 30 and SEQ ID NO: 45; SEQ ID NO: 31 and SEQ ID NO: 46; SEQ ID NO: 32 and SEQ ID NO: 47; SEQ ID NO: 33 and SEQ ID NO: 48; SEQ ID NO: 34 and SEQ ID NO: 49; SEQ ID NO: 35 and SEQ ID NO: 50; SEQ ID NO: 36 and SEQ ID NO: 51; SEQ ID NO: 37 and SEQ ID NO: 52; SEQ ID NO: 38 and SEQ ID NO: 53; SEQ ID NO: 39 and SEQ ID NO: 54; SEQ ID NO: 40 and SEQ ID NO: 55; SEQ ID NO: 41 and SEQ ID NO: 56; SEQ ID NO: 42 and SEQ ID NO: 57; and SEQ ID NO: 43 and SEQ ID NO: 58;
    performing polymerase chain reaction on the cDNA, thereby simultaneously obtaining IFN transcript levels of the set of IFN transcripts from the sample obtained from the individual;
    determining a pattern of IFN transcript levels;
    comparing the pattern of IFN transcript levels of the individual to a pattern of IFN transcript levels of a known immune response; and
    categorizing the immune response of the individual as corresponding to the known immune response if the pattern of IFN transcript levels of the individual substantially match the pattern of IFN transcript levels of the known immune response; or
    categorizing the immune response of the individual as not corresponding to the known immune response if the pattern of IFN transcript levels of the individual do not substantially match the pattern of IFN transcript levels of the known immune response.

2. The method of claim 1, wherein the set of IFN subtype transcripts comprises IFN-alpha1 transcripts.

3. The method of claim 1, wherein the set of IFN subtype transcripts comprises at least four IFN subtype transcripts.

4. The method of claim 1, wherein the set comprises at least six IFN subtype transcripts.

5. The method of claim 1, wherein the set comprises at least eight IFN subtype transcripts.

6. The method of claim 1, wherein the set comprises at least eleven IFN subtype transcripts.

7. The method of claim 1, wherein the composition comprising at least the first and second oligonucleotide pairs further comprises reverse-transcriptase.

8. The method of claim 1, wherein the composition further comprises a probe selected from the list of probes consisting of SEQ ID NO: 59; SEQ ID NO: 60; SEQ ID NO: 61; SEQ ID NO: 62; SEQ ID NO: 63; SEQ ID NO: 64; SEQ ID NO: 65; SEQ ID NO: 66; SEQ ID NO: 67; SEQ ID NO: 68; SEQ ID NO: 69; SEQ ID NO: 70; SEQ ID NO: 71; and SEQ ID NO: 72.

9. The method of claim 1, wherein the sample comprises at least one cell type selected from the list consisting of monocytes, monocyte-derived macrophages, monocyte-derived dendritic cells, plasmacytoid dendritic cells, myeloid dendritic cells and human B cells.

10. The method of claim 1, wherein, the sample comprises bodily fluid.

11. The method of claim 1, wherein the sample comprises tumor tissue.

12. The method of claim 1, comprising selecting a treatment corresponding to the known immune response.

13. The method of claim 12, wherein the known immune response is an immune response to at least one of cancer, a viral infection, inflammation and an autoimmune disorder.

14. The method of claim 1, wherein the comparing comprises comparing patterns of transcript levels.

15. The method of claim 1, wherein the set of IFN subtype transcripts comprises at least thirteen IFN subtype transcripts.

* * * * *

SEQUENCE LISTING

<160> NUMBER OF SEQ ID NOS: 90

<210> SEQ ID NO 1
<211> LENGTH: 456
<212> TYPE: DNA
<213> ORGANISM: Homo sapiens

<400> SEQUENCE: 1
tgtgatctcc ctgagaccca cagcctggat aacaggagga ccttgatgct cctggcacaa      60
atgagcagaa tctctccttc ctcctgtctg atggacagac atgactttgg atttccccag     120
gaggagtttg atggcaacca gttccagaag gctccagcca tctctgtcct ccatgagctg     180
atccagcaga tcttcaacct ctttaccaca aaagattcat ctgctgcttg ggatgaggac     240
ctcctagaca aattctgcac cgaactctac cagcagctga tgacttgga agcctgtgtg      300 atgcaggagg agagggtggg agaaactccc ctgatgaatg tggactccat cttggctgtg     360
aagaaatact tccgaagaat cactctctat ctgacagaga gaaatacag ccttgtgcc       420 tgggaggttg tcagagcaga atcatgaga tccctc                                456

<210> SEQ ID NO 2
<211> LENGTH: 456
<212> TYPE: DNA
<213> ORGANISM: Homo sapiens

<400> SEQUENCE: 2
tgtgatctcc ctgagaccca cagcctggat aacaggagga ccttgatgct cctggcacaa      60
atgagcagaa tctctccttc ctcctgtctg atggacagac atgactttgg atttccccag     120
gaggagtttg atggcaacca gttccagaag gctccagcca tctctgtcct ccatgagctg     180
atccagcaga tcttcaacct ctttaccaca aaagattcat ctgctgcttg ggatgaggac     240
ctcctagaca aattctgcac cgaactctac cagcagctga tgacttgga agcctgtgtg      300 atgcaggagg agagggtggg agaaactccc ctgatgaatg cggactccat cttggctgtg     360
aagaaatact tccgaagaat cactctctat ctgacagaga gaaatacag ccttgtgcc       420 tgggaggttg tcagagcaga atcatgaga tccctc                                456

<210> SEQ ID NO 3
<211> LENGTH: 453
<212> TYPE: DNA
<213> ORGANISM: Homo sapiens

<400> SEQUENCE: 3
tgtgatctgc ctcaaaccca cagcctgggt agcaggagga ccttgatgct cctggcacag      60
atgaggaaaa tctctctttt ctcctgcttg aaggacagac atgactttgg atttccccag     120
gaggagtttg gcaaccagtt ccaaaaggct gaaaccatcc ctgtcctcca tgagatgatc     180
cagcagatct tcaatctctt cagcacaaag gactcatctg ctgcttggga tgagaccctc     240
ctagacaaat tctacactga actctaccag cagctgaatg acctggaagc ctgtgtgata     300 caggggggtgg gggtgacaga gactcccctg atgaaggagg actccattct ggctgtgagg     360
aaatacttcc aaagaatcac tctctatctg aaagagaaga atacagccc ttgtgcctgg      420 gaggttgtca gagcagaaat catgagatct ttt                                  453

<210> SEQ ID NO 4
<211> LENGTH: 453
<212> TYPE: DNA
<213> ORGANISM: Homo sapiens

<400> SEQUENCE: 4

```
tgtgatctgc ctcaaaccca cagcctgggt agcaggagga ccttgatgct cctggcacag    60
atgaggagaa tctctctttt ctcctgcttg aaggacagac atgactttgg atttccccag   120
gaggagtttg gcaaccagtt ccaaaaggct gaaaccatcc ctgtcctcca tgagatgatc   180
cagcagatct tcaatctctt cagcacaaag gactcatctg ctgcttggga tgagaccctc   240
ctagacaaat tctacactga actctaccag cagctgaatg acctggaagc ctgtgtgata   300
caggggtgg gggtgacaga gactcccctg atgaaggagg actccattct ggctgtgagg   360
aaatacttcc aaagaatcac tctctatctg aaagagaaga atacagcccc ttgtgcctgg   420
gaggttgtca gagcagaaat catgagatct ttt                                 453
```

<210> SEQ ID NO 5
<211> LENGTH: 456
<212> TYPE: DNA
<213> ORGANISM: Homo sapiens

<400> SEQUENCE: 5

```
tgtgatctgc ctcagaccca cagcctgggt aataggaggg ccttgatact cctggcacaa    60
atgggaagaa tctctcattt ctcctgcctg aaggacagac atgatttcgg attccccgag   120
gaggagtttg atggccacca gttccagaag gctcaagcca tctctgtcct ccatgagatg   180
atccagcaga ccttcaatct cttcagcaca gaggactcat ctgctgcttg ggaacagagc   240
ctcctagaaa aatttttccac tgaactttac cagcaactga atgacctgga agcatgtgtg   300
atacaggagg ttggggtgga agagactccc ctgatgaatg aggactccat cctggctgtg   360
aggaaatact ccaaagaat cactctttat ctaacagaga gaaatacag cccttgtgcc    420
tgggaggttg tcagagcaga aatcatgaga tccctc                              456
```

<210> SEQ ID NO 6
<211> LENGTH: 456
<212> TYPE: DNA
<213> ORGANISM: Homo sapiens

<400> SEQUENCE: 6

```
tgtgatctgc ctcagaccca cagcctgggt aataggaggg ccttgatact cctggcacaa    60
atgggaagaa tctctcattt ctcctgcctg aaggacagac atgatttcgg attccccgag   120
gaggagtttg atggccacca gttccagaag actcaagcca tctctgtcct ccatgagatg   180
atccagcaga ccttcaatct cttcagcaca gaggactcat ctgctgcttg ggaacagagc   240
ctcctagaaa aatttttccac tgaactttac cagcaactga atgacctgga agcatgtgtg   300
atacaggagg ttggggtgga agagactccc ctgatgaatg tggactccat cctggctgtg   360
aggaaatact ccaaagaat cactctttat ctaacagaga gaaatacag cccttgtgcc    420
tgggaggttg tcagagcaga aatcatgaga tccctc                              456
```

<210> SEQ ID NO 7
<211> LENGTH: 456
<212> TYPE: DNA
<213> ORGANISM: Homo sapiens

<400> SEQUENCE: 7

```
tgtgatctgc ctcagaccca cagcctgagt aacaggagga ctttgatgat aatggcacaa    60
atgggaagaa tctctccttt ctcctgcctg aaggacagac atgactttgg atttcctcag   120
```

-continued

| | |
|---|---|
| gaggagtttg atggcaacca gttccagaag gctcaagcca tctctgtcct ccatgagatg | 180 |
| atccagcaga ccttcaatct cttcagcaca aaggactcat ctgctacttg ggatgagaca | 240 |
| cttctagaca aattctacac tgaactttac cagcagctga atgacctgga agcctgtatg | 300 |
| atgcaggagg ttggagtgga agacactcct ctgatgaatg tggactctat cctgactgtg | 360 |
| agaaaatact ttcaaagaat caccctctat ctgacagaga gaaatacag cccttgtgca | 420 |
| tgggaggttg tcagagcaga aatcatgaga tccttc | 456 |

<210> SEQ ID NO 8
<211> LENGTH: 456
<212> TYPE: DNA
<213> ORGANISM: Homo sapiens

<400> SEQUENCE: 8

| | |
|---|---|
| tgtgatctgc ctcagaccca cagcctgggt cacaggagga ccatgatgct cctggcacaa | 60 |
| atgaggagaa tctctctttt ctcctgtctg aaggacagac atgacttcag atttccccag | 120 |
| gaggagtttg atggcaacca gttccagaag gctgaagcca tctctgtcct ccatgaggtg | 180 |
| attcagcaga ccttcaatct cttcagcaca aaggactcat ctgttgcttg ggatgagagg | 240 |
| cttctagaca aactctatac tgaactttac cagcagctga atgacctgga agcctgtgtg | 300 |
| atgcaggagg tgtgggtggg agggactccc ctgatgaatg aggactccat cctggctgtg | 360 |
| agaaaatact tccaaagaat cactctctac ctgacagaga aaaagtacag cccttgtgcc | 420 |
| tgggaggttg tcagagcaga aatcatgaga tccttc | 456 |

<210> SEQ ID NO 9
<211> LENGTH: 456
<212> TYPE: DNA
<213> ORGANISM: Homo sapiens

<400> SEQUENCE: 9

| | |
|---|---|
| tgtgatctgc ctcagaccca cagcctgcgt aataggaggg ccttgatact cctggcacaa | 60 |
| atgggaagaa tctctccttt ctcctgcttg aaggacagac atgaattcag attcccagag | 120 |
| gaggagtttg atggcaacca gttccagaag actcaagcca tctctgtcct ccatgagatg | 180 |
| atccagcaga ccttcaatct cttcagcaca gaggactcat ctgctgcttg ggaacagagc | 240 |
| ctcctagaaa aattttccac tgaactttac cagcaactga atgacctgga agcatgtgtg | 300 |
| atacaggagg ttggggtgga agagactccc ctgatgaatg aggacttcat cctggctgtg | 360 |
| aggaaatact tccaaagaat cactctttat ctaatggaga gaaatacag cccttgtgcc | 420 |
| tgggaggttg tcagagcaga aatcatgaga tccttc | 456 |

<210> SEQ ID NO 10
<211> LENGTH: 456
<212> TYPE: DNA
<213> ORGANISM: Homo sapiens

<400> SEQUENCE: 10

| | |
|---|---|
| tgtgatctgc ctcagactca cagcctgggt aacaggaggg ccttgatact cctggcacaa | 60 |
| atgcgaagaa tctctccttt ctcctgcctg aaggacagac atgactttga attccccag | 120 |
| gaggagtttg atgataaaca gttccagaag gctcaagcca tctctgtcct ccatgagatg | 180 |
| atccagcaga ccttcaacct cttcagcaca aaggactcat ctgctgcttt ggatgagacc | 240 |
| cttctagatg aattctacat cgaacttgac cagcagctga atgacctgga gtcctgtgtg | 300 |
| atgcaggaag tgggggtgat agagtctccc ctgatgtacg aggactccat cctggctgtg | 360 | aggaaatact tccaaagaat cactctatat ctgacagaga agaaatacag ctcttgtgcc  420 tgggaggttg tcagagcaga aatcatgaga tccttc  456

<210> SEQ ID NO 11
<211> LENGTH: 456
<212> TYPE: DNA
<213> ORGANISM: Homo sapiens

<400> SEQUENCE: 11
tgtgatctgc ctcagaccca cagcctcggt aataggaggg ccttgatact cctgggacaa  60
atgggaagaa tctctccttt ctcctgcctg aaggacagac atgatttccg aatcccccag  120
gaggagtttg atggcaacca gttccagaag gctcaagcca tctctgtcct ccatgagatg  180
atccagcaga ccttcaatct cttcagcaca gaggactcat ctgctgcttg ggaacagagc  240
ctcctagaaa aattttccac tgaactttac cagcaactga atgacctgga agcatgtgtg  300
atacaggagg ttggggtgga agagactccc ctgatgaatg aggactccat cctggctgtg  360
aggaaatact tccaaagaat cactctttat ctaatagaga ggaaatacag cccttgtgcc  420
tgggaggttg tcagagcaga aatcatgaga tccctc  456

<210> SEQ ID NO 12
<211> LENGTH: 456
<212> TYPE: DNA
<213> ORGANISM: Homo sapiens

<400> SEQUENCE: 12
tgtaatctgt ctcaaaccca cagcctgaat aacaggagga ctttgatgct catggcacaa  60
atgaggagaa tctctccttt ctcctgcctg aaggacagac atgactttga atttccccag  120
gaggaatttg atggcaacca gttccagaaa gctcaagcca tctctgtcct ccatgagatg  180
atgcagcaga ccttcaatct cttcagcaca aagaactcat ctgctgcttg ggatgagacc  240
ctcctagaaa aattctacat tgaacttttc cagcaaatga atgacctgga agcctgtgtg  300
atacaggagg ttggggtgga agagactccc ctgatgaatg aggactccat cctggctgtg  360
aagaaatact tccaaagaat cactctttat ctgatggaga gaaatacag cccttgtgcc  420 tgggaggttg tcagagcaga aatcatgaga tccctc  456

<210> SEQ ID NO 13
<211> LENGTH: 456
<212> TYPE: DNA
<213> ORGANISM: Homo sapiens

<400> SEQUENCE: 13
tgtgatctgc ctcagactca cagcctgggt aataggaggg ccttgatact cctggcacaa  60
atgggaagaa tctctcattt ctcctgcctg aaggacagat atgatttcgg attccccag  120 gaggtgtttg atggcaacca gttccagaag gctcaagcca tctctgcctt ccatgagatg  180
atccagcaga ccttcaatct cttcagcaca aaggattcat ctgctgcttg ggatgagacc  240
ctcctagaca aattctacat tgaactttc cagcaactga atgacctaga agcctgtgtg  300
acacaggagg ttggggtgga agagattgcc ctgatgaatg aggactccat cctggctgtg  360
aggaaatact ttcaaagaat cactctttat ctgatgggga agaaatacag cccttgtgcc  420
tgggaggttg tcagagcaga aatcatgaga tccttc  456

<210> SEQ ID NO 14

-continued

<211> LENGTH: 456
<212> TYPE: DNA
<213> ORGANISM: Homo sapiens

<400> SEQUENCE: 14

```
tgtgatctgc ctcagaccca cagcctgggt aataggaggg ccttgatact cctggcacaa    60
atgggaagaa tctctccttt ctcctgcctg aaggacagac ctgactttgg acttccccag   120
gaggagtttg atggcaacca gttccagaag actcaagcca tctctgtcct ccatgagatg   180
atccagcaga ccttcaatct cttcagcaca gaggactcat ctgctgcttg gaacagagc   240
ctcctagaaa aatttccac tgaactttac cagcaactga ataacctgga agcatgtgtg   300
atacaggagg ttgggatgga agagactccc ctgatgaatg aggactccat cctggctgtg   360
aggaaatact tccaaagaat cactctttat ctaacagaga gaaatacag cccttgtgcc   420
tgggaggttg tcagagcaga aatcatgaga tctctc                            456
```

<210> SEQ ID NO 15
<211> LENGTH: 456
<212> TYPE: DNA
<213> ORGANISM: Homo sapiens

<400> SEQUENCE: 15

```
tgtgatctgc ctcagaccca cagcctgggt aataggaggg ccttgatact cctggcacaa    60
atgggaagaa tctctccttt ctcctgcctg aaggacagac atgactttgg attccccaa   120
gaggagtttg atggcaacca gttccagaag gctcaagcca tctctgtcct ccatgagatg   180
atccagcaga ccttcaatct cttcagcaca aaggactcat ctgctacttg gaacagagc   240
ctcctagaaa aatttccac tgaacttaac cagcagctga atgacatgga agcctgcgtg   300
atacaggagg ttggggtgga agagactccc ctgatgaatg tggactccat cttggctgtg   360
aagaaatact tccaaagaat cactctttat ctgacagaga gaaatacag cccttgtgct   420
tgggaggttg tcagagcaga aatcatgaga tccttc                            456
```

<210> SEQ ID NO 16
<211> LENGTH: 152
<212> TYPE: PRT
<213> ORGANISM: Homo sapiens

<400> SEQUENCE: 16

```
Cys Asp Leu Pro Glu Thr His Ser Leu Asp Asn Arg Arg Thr Leu Met
 1               5                  10                  15
Leu Leu Ala Gln Met Ser Arg Ile Ser Pro Ser Ser Cys Leu Met Asp
            20                  25                  30
Arg His Asp Phe Gly Phe Pro Gln Glu Glu Phe Asp Gly Asn Gln Phe
        35                  40                  45
Gln Lys Ala Pro Ala Ile Ser Val Leu His Glu Leu Ile Gln Gln Ile
    50                  55                  60
Phe Asn Leu Phe Thr Thr Lys Asp Ser Ser Ala Ala Trp Asp Glu Asp
65                  70                  75                  80
Leu Leu Asp Lys Phe Cys Thr Glu Leu Tyr Gln Gln Leu Asn Asp Leu
                85                  90                  95
Glu Ala Cys Val Met Gln Glu Glu Arg Val Gly Glu Thr Pro Leu Met
            100                 105                 110
Asn Val Asp Ser Ile Leu Ala Val Lys Lys Tyr Phe Arg Arg Ile Thr
        115                 120                 125
Leu Tyr Leu Thr Glu Lys Lys Tyr Ser Pro Cys Ala Trp Glu Val Val
```

```
              130                 135                 140
Arg Ala Glu Ile Met Arg Ser Leu
145                 150

<210> SEQ ID NO 17
<211> LENGTH: 152
<212> TYPE: PRT
<213> ORGANISM: Homo sapiens

<400> SEQUENCE: 17

Cys Asp Leu Pro Glu Thr His Ser Leu Asp Asn Arg Arg Thr Leu Met
1               5                   10                  15

Leu Leu Ala Gln Met Ser Arg Ile Ser Pro Ser Ser Cys Leu Met Asp
            20                  25                  30

Arg His Asp Phe Gly Phe Pro Gln Glu Glu Phe Asp Gly Asn Gln Phe
        35                  40                  45

Gln Lys Ala Pro Ala Ile Ser Val Leu His Glu Leu Ile Gln Gln Ile
    50                  55                  60

Phe Asn Leu Phe Thr Thr Lys Asp Ser Ser Ala Ala Trp Asp Glu Asp
65                  70                  75                  80

Leu Leu Asp Lys Phe Cys Thr Glu Leu Tyr Gln Gln Leu Asn Asp Leu
                85                  90                  95

Glu Ala Cys Val Met Gln Glu Glu Arg Val Gly Glu Thr Pro Leu Met
            100                 105                 110

Asn Ala Asp Ser Ile Leu Ala Val Lys Lys Tyr Phe Arg Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu
145                 150

<210> SEQ ID NO 18
<211> LENGTH: 151
<212> TYPE: PRT
<213> ORGANISM: Homo sapiens

<400> SEQUENCE: 18

Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe
```

<210> SEQ ID NO 19
<211> LENGTH: 151
<212> TYPE: PRT
<213> ORGANISM: Homo sapiens

<400> SEQUENCE: 19

Cys Asp Leu Pro Gln Thr His Ser Leu Gly Ser Arg Arg Thr Leu Met
1               5                   10                  15

Leu Leu Ala Gln Met Arg Arg Ile Ser Leu Phe Ser Cys Leu Lys Asp
            20                  25                  30

Arg His Asp Phe Gly Phe Pro Gln Glu Glu Phe Gly Asn Gln Phe Gln
        35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe
145                 150

<210> SEQ ID NO 20
<211> LENGTH: 152
<212> TYPE: PRT
<213> ORGANISM: Homo sapiens

<400> SEQUENCE: 20

Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg His Asp Phe Gly Phe Pro Glu Glu Glu Phe Asp Gly His Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu
145                 150

<210> SEQ ID NO 21
<211> LENGTH: 152
<212> TYPE: PRT
<213> ORGANISM: Homo sapiens

<400> SEQUENCE: 21

Cys Asp Leu Pro Gln Thr His Ser Leu Gly Asn Arg Arg Ala Leu Ile
1               5                   10                  15

Leu Leu Ala Gln Met Gly Arg Ile Ser His Phe Ser Cys Leu Lys Asp
            20                  25                  30

Arg His Asp Phe Gly Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Val Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Leu
145                 150

<210> SEQ ID NO 22
<211> LENGTH: 152
<212> TYPE: PRT
<213> ORGANISM: Homo sapiens

<400> SEQUENCE: 22

Cys Asp Leu Pro Gln Thr His Ser Leu Ser Asn Arg Arg Thr Leu Met
1               5                   10                  15

Ile Met Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Asp Glu Thr
65                  70                  75                  80

Leu Leu Asp Lys Phe Tyr Thr Glu Leu Tyr Gln Gln Leu Asn Asp Leu
                85                  90                  95

Glu Ala Cys Met Met Gln Glu Val Gly Val Glu Asp Thr Pro Leu Met
            100                 105                 110

Asn Val Asp Ser Ile Leu Thr Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe
145                 150

<210> SEQ ID NO 23
<211> LENGTH: 152
<212> TYPE: PRT

```
<213> ORGANISM: Homo sapiens

<400> SEQUENCE: 23

Cys Asp Leu Pro Gln Thr His Ser Leu Gly His Arg Arg Thr Met Met
1               5                   10                  15

Leu Leu Ala Gln Met Arg Arg Ile Ser Leu Phe Ser Cys Leu Lys Asp
            20                  25                  30

Arg His Asp Phe Arg Phe Pro Gln Glu Glu Phe Asp Gly Asn Gln Phe
        35                  40                  45

Gln Lys Ala Glu Ala Ile Ser Val Leu His Glu Val Ile Gln Gln Thr
    50                  55                  60

Phe Asn Leu Phe Ser Thr Lys Asp Ser Ser Val Ala Trp Asp Glu Arg
65                  70                  75                  80

Leu Leu Asp Lys Leu Tyr Thr Glu Leu Tyr Gln Gln Leu Asn Asp Leu
                85                  90                  95

Glu Ala Cys Val Met Gln Glu Val Trp Val Gly Gly Thr Pro Leu Met
            100                 105                 110

Asn Glu Asp Ser Ile Leu Ala Val Arg Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe
145                 150

<210> SEQ ID NO 24
<211> LENGTH: 152
<212> TYPE: PRT
<213> ORGANISM: Homo sapiens

<400> SEQUENCE: 24

Cys Asp Leu Pro Gln Thr His Ser Leu Arg Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Glu Phe Arg Phe Pro Glu Glu Glu Phe Asp Gly His Gln Phe
        35                  40                  45

Gln Lys Thr Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Phe Ile Leu Ala Val Arg Lys Tyr Phe Gln Arg Ile Thr
        115                 120                 125

Leu Tyr Leu Met Glu Lys Lys Tyr Ser Pro Cys Ala Trp Glu Val Val
    130                 135                 140

Arg Ala Glu Ile Met Arg Ser Phe
145                 150

<210> SEQ ID NO 25
<211> LENGTH: 152
<212> TYPE: PRT
<213> ORGANISM: Homo sapiens

<400> SEQUENCE: 25
```

```
Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
            115                 120                 125

Leu Tyr Leu Thr Glu Lys Lys Tyr Ser Ser Cys Ala Trp Glu Val Val
    130                 135                 140

Arg Ala Glu Ile Met Arg Ser Phe
145                 150

<210> SEQ ID NO 26
<211> LENGTH: 152
<212> TYPE: PRT
<213> ORGANISM: Homo sapiens

<400> SEQUENCE: 26

Cys Asp Leu Pro Gln Thr His Ser Leu Gly Asn Arg Arg Ala Leu Ile
1               5                   10                  15

Leu Leu Gly Gln Met Gly Arg Ile Ser Pro Phe Ser Cys Leu Lys Asp
            20                  25                  30

Arg His Asp Phe Arg Ile Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Glu Asp Ser Ser Ala Ala Trp Glu Gln Ser
65                  70                  75                  80

Leu Leu Glu Lys Phe Ser Thr Glu Leu Tyr Gln Gln Leu Asn Asp Leu
                85                  90                  95

Glu Ala Cys Val Ile Gln Glu Val Gly Val Glu Glu Thr Pro Leu Met
            100                 105                 110

Asn Glu Asp Ser Ile Leu Ala Val Arg Lys Tyr Phe Gln Arg Ile Thr
            115                 120                 125

Leu Tyr Leu Ile Glu Arg Lys Tyr Ser Pro Cys Ala Trp Glu Val Val
    130                 135                 140

Arg Ala Glu Ile Met Arg Ser Leu
145                 150

<210> SEQ ID NO 27
<211> LENGTH: 152
<212> TYPE: PRT
<213> ORGANISM: Homo sapiens

<400> SEQUENCE: 27

Cys Asn Leu Ser Gln Thr His Ser Leu Asn Asn Arg Arg Thr Leu Met
1               5                   10                  15
```

```
Leu Met Ala Gln Met Arg Arg Ile Ser Pro Phe Ser Cys Leu Lys Asp
                20                  25                  30

Arg His Asp Phe Glu Phe Pro Gln Glu Glu Phe Asp Gly Asn Gln Phe
            35                  40                  45

Gln Lys Ala Gln Ala Ile Ser Val Leu His Glu Met Met Gln Gln Thr
        50                  55                  60

Phe Asn Leu Phe Ser Thr Lys Asn Ser Ser Ala Ala Trp Asp Glu Thr
 65                  70                  75                  80

Leu Leu Glu Lys Phe Tyr Ile Glu Leu Phe Gln Gln Met Asn Asp Leu
                85                  90                  95

Glu Ala Cys Val Ile Gln Glu Val Gly Val Glu Thr Pro Leu Met
            100                 105                 110

Asn Glu Asp Ser Ile Leu Ala Val Lys Lys Tyr Phe Gln Arg Ile Thr
            115                 120                 125

Leu Tyr Leu Met Glu Lys Lys Tyr Ser Pro Cys Ala Trp Glu Val Val
        130                 135                 140

Arg Ala Glu Ile Met Arg Ser Leu
145                 150

<210> SEQ ID NO 28
<211> LENGTH: 152
<212> TYPE: PRT
<213> ORGANISM: Homo sapiens

<400> SEQUENCE: 28

Cys Asp Leu Pro Gln Thr His Ser Leu Gly Asn Arg Arg Ala Leu Ile
 1               5                  10                  15

Leu Leu Ala Gln Met Gly Arg Ile Ser His Phe Ser Cys Leu Lys Asp
                20                  25                  30

Arg Tyr Asp Phe Gly Phe Pro Gln Glu Val Phe Asp Gly Asn Gln Phe
            35                  40                  45

Gln Lys Ala Gln Ala Ile Ser Ala Phe His Glu Met Ile Gln Gln Thr
        50                  55                  60

Phe Asn Leu Phe Ser Thr Lys Asp Ser Ser Ala Ala Trp Asp Glu Thr
 65                  70                  75                  80

Leu Leu Asp Lys Phe Tyr Ile Glu Leu Phe Gln Gln Leu Asn Asp Leu
                85                  90                  95

Glu Ala Cys Val Thr Gln Glu Val Gly Val Glu Ile Ala Leu Met
            100                 105                 110

Asn Glu Asp Ser Ile Leu Ala Val Arg Lys Tyr Phe Gln Arg Ile Thr
            115                 120                 125

Leu Tyr Leu Met Gly Lys Lys Tyr Ser Pro Cys Ala Trp Glu Val Val
        130                 135                 140

Arg Ala Glu Ile Met Arg Ser Phe
145                 150

<210> SEQ ID NO 29
<211> LENGTH: 152
<212> TYPE: PRT
<213> ORGANISM: Homo sapiens

<400> SEQUENCE: 29

Cys Asp Leu Pro Gln Thr His Ser Leu Gly Asn Arg Arg Ala Leu Ile
 1               5                  10                  15

Leu Leu Ala Gln Met Gly Arg Ile Ser Pro Phe Ser Cys Leu Lys Asp
                20                  25                  30
```

Arg Pro Asp Phe Gly Leu Pro Gln Glu Glu Phe Asp Gly Asn Gln Phe
            35                  40                  45

Gln Lys Thr Gln Ala Ile Ser Val Leu His Glu Met Ile Gln Gln Thr
 50                  55                  60

Phe Asn Leu Phe Ser Thr Glu Asp Ser Ser Ala Ala Trp Gln Ser
 65                  70                  75                  80

Leu Leu Glu Lys Phe Ser Thr Glu Leu Tyr Gln Gln Leu Asn Leu
                    85                  90                  95

Glu Ala Cys Val Ile Gln Glu Val Gly Met Glu Glu Thr Pro Leu Met
                100                 105                 110

Asn Glu Asp Ser Ile Leu Ala Val Arg Lys Tyr Phe Gln Arg Ile Thr
                115                 120                 125

Leu Tyr Leu Thr Glu Lys Lys Tyr Ser Pro Cys Ala Trp Glu Val Val
130                 135                 140

Arg Ala Glu Ile Met Arg Ser Leu
145                 150

```
<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
tagacaaatt ctgcaccgaa c                                            21

<210> SEQ ID NO 31
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
ggtagcagga ggaccttgat g                                            21

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
tcatttctcc tgcctgaagg                                              20

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
```

```
gatactcctg gcacaaatgg                                            20

<210> SEQ ID NO 34
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
gatactcctg gcacaaatgg                                            20

<210> SEQ ID NO 35
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
cacttctaga caaattctac actg                                       24

<210> SEQ ID NO 36
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
tgattcagca gaccttcaat c                                          21

<210> SEQ ID NO 37
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
cagacccaca gcctgcgt                                              18

<210> SEQ ID NO 38
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 38
gatgataaac agttccagaa gg                                         22

<210> SEQ ID NO 39
<211> LENGTH: 21
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic primer"

<400> SEQUENCE: 39
gggacaaatg ggaagaatct c                                            21

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
aggaggaatt tgatggcaac                                              20

<210> SEQ ID NO 41
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
attgaacttt tccagcaact g                                            21

<210> SEQ ID NO 42
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
aatgggaaga atctctcctt tc                                           22

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
tcatctgcta cttgggaaca g                                            21

<210> SEQ ID NO 44
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
tcctttctcc                                                         10

<210> SEQ ID NO 45
```

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
<220> FEATURE:
<221> NAME/KEY: modified_base
<222> LOCATION: (12)..(12)
<223> OTHER INFORMATION: Inosine

<400> SEQUENCE: 45
agatggagtc cncattcatc                                               20

<210> SEQ ID NO 46
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
ggaggacagg gatggtttca g                                             21

<210> SEQ ID NO 47
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
gaggacagag atggcttgag                                               20

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
aaggtctgct ggatcatctc                                               20

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
aaggtctgct ggatcatctc                                               20

<210> SEQ ID NO 50
<211> LENGTH: 22
<212> TYPE: DNA
<213> ORGANISM: Artificial Sequence
<220> FEATURE:
<221> NAME/KEY: source
```

<223> OTHER INFORMATION: /note="Description of Artificial Sequence:
      Synthetic primer"

<400> SEQUENCE: 50
ggatagagtc cacattcatc ag                                              22

<210> SEQ ID NO 51
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
tgctggtaaa gttcagtata gag                                             23

<210> SEQ ID NO 52
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
aaactcctcc tctgggaatc tg                                              22

<210> SEQ ID NO 53
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
aagttcgatg tagaattcat ctag                                            24

<210> SEQ ID NO 54
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 54
aactggttgc catcaaactc                                                 20

<210> SEQ ID NO 55
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 55
agcagcagat gagttctttg                                                 20

<210> SEQ ID NO 56

```
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 56
ttcatcaggg caatctcttc                                               20

<210> SEQ ID NO 57
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 57
cttgagtctt ctggaactgg                                               20

<210> SEQ ID NO 58
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 58
cacattcatc agggagtct c                                              21

<210> SEQ ID NO 59
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 59
ctcccaccct ctcctc                                                   16

<210> SEQ ID NO 60
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 60
cgcgatcccc caggaggagt tggcaacga tcgcg                               35

<210> SEQ ID NO 61
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 61
```

```
ctcggggaat ccgaaatc                                                    18

<210> SEQ ID NO 62
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 62
cgcgatcgct tgagccttct ggaactggtg ggatcgcg                              38

<210> SEQ ID NO 63
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 63
cgcgatcgct tgagtcttct ggaactggtg ggatcgcg                              38

<210> SEQ ID NO 64
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 64
ttccactcca acctcct                                                     17

<210> SEQ ID NO 65
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 65
agcctctcat cccaagc                                                     17

<210> SEQ ID NO 66
<211> LENGTH: 42
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 66
cgcgatctgg cacaaatggg aagaatctct cctttgatcg cg                         42

<210> SEQ ID NO 67
<211> LENGTH: 17
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic probe"

<400> SEQUENCE: 67
ctcatccaaa gcagcag                                                     17

<210> SEQ ID NO 68
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 68
agacatgatt tccgaatccc c                                                21

<210> SEQ ID NO 69
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 69
tccagaaagc tcaagcc                                                     17

<210> SEQ ID NO 70
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 70
atgacctaga agcctgt                                                     17

<210> SEQ ID NO 71
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 71
acagacctga ctttggactt                                                  20

<210> SEQ ID NO 72
<211> LENGTH: 37
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 72
cgcgatctcc tgtatcacgc aggcttccat gatcgcg                               37
```

<210> SEQ ID NO 73
<211> LENGTH: 456
<212> TYPE: DNA
<213> ORGANISM: Artificial Sequence
<220> FEATURE:
<221> NAME/KEY: source
<223> OTHER INFORMATION: /note="Description of Artificial Sequence: Synthetic consensus polynucleotide"

<400> SEQUENCE: 73

```
tgtgatctgc ctcagaccca cagcctgggt aataggaggg ccttgatact cctggcacaa      60
atgggaagaa tctctccttt ctcctgcctg aaggacagac atgactttgg attcccccag     120
gaggagtttg atggcaacca gttccagaag gctcaagcca tctctgtcct ccatgagatg     180
atccagcaga ccttcaatct cttcagcaca aaggactcat ctgctgcttg ggatgagagc     240
ctcctagaca aattttacac tgaactttac cagcaactga atgacctgga agcatgtgtg     300
atacaggagg ttggggtgga agagactccc ctgatgaatg aggactccat cctggctgtg     360
aggaaatact tccaaagaat cactctttat ctaacagaga agaaatacag cccttgtgcc     420
tgggaggttg tcagagcaga aatcatgaga tccttc                                456
```

<210> SEQ ID NO 74
<211> LENGTH: 152
<212> TYPE: PRT
<213> ORGANISM: Homo sapiens

<400> SEQUENCE: 74

```
Cys Asp Leu Pro Gln Thr His Ser Leu Gly Asn Arg Arg Ala Leu Ile
1               5                   10                  15

Leu Leu Ala Gln Met Gly Arg Ile Ser Pro Phe Ser Cys Leu Lys Asp
            20                  25                  30

Arg His Asp Phe Gly Phe Pro Gln Glu Glu Phe Asp Gly Asn Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Thr Trp Glu Gln Ser
65                  70                  75                  80

Leu Leu Glu Lys Phe Ser Thr Glu Leu Asn Gln Gln Leu Asn Asp Met
                85                  90                  95

Glu Ala Cys Val Ile Gln Glu Val Gly Val Glu Thr Pro Leu Met
            100                 105                 110

Asn Val Asp Ser Ile Leu Ala Val Lys Lys Tyr Phe Gln Arg Ile Thr
        115                 120                 125

Leu Tyr Leu Thr Glu Lys Lys Tyr Ser Pro Cys Ala Trp Glu Val Val
    130                 135                 140

Arg Ala Glu Ile Met Arg Ser Phe
145                 150
```

<210> SEQ ID NO 75
<211> LENGTH: 152
<212> TYPE: PRT
<213> ORGANISM: Artificial Sequence
<220> FEATURE:
<221> NAME/KEY: source
<223> OTHER INFORMATION: /note="Description of Artificial Sequence: Synthetic consensus polypeptide"

<400> SEQUENCE: 75

```
Cys Asp Leu Pro Gln Thr His Ser Leu Gly Asn Arg Arg Ala Leu Ile
1               5                   10                  15
```

```
Leu Leu Ala Gln Met Gly Arg Ile Ser Pro Phe Ser Cys Leu Lys Asp
             20                  25                  30
Arg His Asp Phe Gly Phe Pro Gln Glu Glu Phe Asp Gly Asn Gln Phe
         35                  40                  45
Gln Lys Ala Gln Ala Ile Ser Val Leu His Glu Met Ile Gln Gln Thr
     50                  55                  60
Phe Asn Leu Phe Ser Thr Lys Asp Ser Ser Ala Ala Trp Asp Glu Ser
 65                  70                  75                  80
Leu Leu Asp Lys Phe Tyr Thr Glu Leu Tyr Gln Gln Leu Asn Asp Leu
                 85                  90                  95
Glu Ala Cys Val Ile Gln Glu Val Gly Val Glu Thr Pro Leu Met
            100                 105                 110
Asn Glu Asp Ser Ile Leu Ala Val Arg Lys Tyr Phe Gln Arg Ile Thr
            115                 120                 125
Leu Tyr Leu Thr Glu Lys Lys Tyr Ser Pro Cys Ala Trp Glu Val Val
130                 135                 140
Arg Ala Glu Ile Met Arg Ser Phe
145                 150
```

<210> SEQ ID NO 76
<211> LENGTH: 636
<212> TYPE: DNA
<213> ORGANISM: Homo sapiens

<400> SEQUENCE: 76

```
atggctgcag cttggaccgt ggtgctggtg actttggtgc taggcttggc cgtggcaggc      60
cctgtcccca cttccaagcc caccacaact gggaagggct gccacattgg caggttcaaa     120
tctctgtcac acaggagct agcgagcttc aagaaggcca gggacgcctt ggaagagtca     180
ctcaagctga aaaactggag ttgcagctct cctgtcttcc ccgggaattg ggacctgagg     240
cttctccagg tgagggagcg ccctgtggcc ttggaggctg agctggccct gacgctgaag     300
gtcctggagg ccgctgctgg cccagccctg gaggacgtcc tagaccagcc cttcacacc     360
ctgcaccaca tcctctccca gctccaggcc tgtatccagc tcagcccac agcagggccc     420
aggccccggg gccgcctcca ccactggctg accggctcc aggaggcccc caaaaaggag     480
tccgctggct gcctggaggc atctgtcacc ttcaacctct ccgcctcct cacgcgagac     540
ctcaaatatg tggccgatgg gaacctgtgt ctgagaacgt caacccaccc tgagtccacc     600
tgacacccca caccttattt atgcgctgag ccctac                              636
```

<210> SEQ ID NO 77
<211> LENGTH: 669
<212> TYPE: DNA
<213> ORGANISM: Homo sapiens

<400> SEQUENCE: 77

```
atgactgggg actgcacgcc agtgctggtg ctgatggccg cagtgctgac cgtgactgga      60
gcagttcctg tcgccaggct ccacggggct ctcccggatg caaggggctg ccacatagcc     120
cagttcaagt ccctgtctcc acaggagctg caggccttta gagggccaa agatgcctta     180
gaagagtcgc ttctgctgaa ggactgcagg tgccactccc gcctcttccc caggacctgg     240
gacctgaggc agctgcaggt gagggagcgc ccatggctt tggaggctga gctggccctg     300
acgctgaagt tctggagc caccgctgac actgacccag ccctggtgga cgtcttggac     360
cagcccttc acaccctgca ccatatcctc tcccagttcc gggcctgtat ccagcctcag     420
```

```
cccacggcag ggcccaggac ccggggccgc ctccaccatt ggctgtaccg gctccaggag    480
gccccaaaaa aggagtcccc tggctgcctc gaggcctctg tcaccttcaa cctcttccgc    540
ctcctcacgc gagacctgaa ttgtgttgcc agtggggacc tgtgtgtctg accctcccac    600
cagtcatgca acctgagatt ttatttataa attagccact tgtcttaatt tattgccacc    660
cagtcgcta                                                            669
```

```
<210> SEQ ID NO 78
<211> LENGTH: 591
<212> TYPE: DNA
<213> ORGANISM: Homo sapiens

<400> SEQUENCE: 78
```

```
atgaccgggg actgcatgcc agtgctggtg ctgatggccg cagtgctgac cgtgactgga     60
gcagttcctg tcgccaggct ccgcggggct ctcccggatg caagggggctg ccacatagcc    120 cagttcaagt ccctgtctcc acaggagctg caggccttta agagggccaa agatgcctta    180
gaagagtcgc ttctgctgaa ggactgcaag tgccgctccc gcctcttccc caggacctgg    240
gacctgaggc agctgcaggt gagggagcgc ccgtggcctt tggaggctga gctggccctg    300
acgctgaagg ttctggaggc caccgctgac actgacccag ccctggggga tgtcttggac    360
cagccccttc acaccctgca ccatatcctc tcccagctcc gggcctgtat ccagcctcag    420
cccacggcag ggcccaggac ccggggccgc ctccaccatt ggctgcaccg gctccaggag    480
gccccaaaaa aggagtcccc tggctgcctc gaggcctctg tcaccttcaa cctcttccgc    540
ctcctcacgc gagacctgaa ttgtgttgcc agcggggacc tgtgtgtctg a              591
```

```
<210> SEQ ID NO 79
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 79
```

```
gttcaaatct ctgtcaccac                                                 20
```

```
<210> SEQ ID NO 80
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 80
```

```
gccaaagatg ccttagaaga g                                               21
```

```
<210> SEQ ID NO 81
<211> LENGTH: 17
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 81
```
cgagcttcaa gaaggcc                                                    17

<210> SEQ ID NO 82
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 82
cgcgatcgca ggtgccactc ccgcctctga tcgcg                                 35

<210> SEQ ID NO 83
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 83
cgcgatcgca agtgccgctc ccgcctctga tcgcg                                 35

<210> SEQ ID NO 84
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 84
ttcagcttga gtgactcttc                                                  20

<210> SEQ ID NO 85
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 85
cagaaccttc agcgtcagg                                                   19

<210> SEQ ID NO 86
<211> LENGTH: 840
<212> TYPE: DNA
<213> ORGANISM: Homo sapiens

<400> SEQUENCE: 86
acattctaac tgcaaccttt cgaagccttt gctctggcac aacaggtagt aggcgacact      60
gttcgtgttg tcaacatgac caacaagtgt ctcctccaaa ttgctctcct gttgtgcttc     120
tccactacag ctctttccat gagctacaac ttgcttggat tcctacaaag aagcagcaat     180
tttcagtgtc agaagctcct gtggcaattg aatgggaggc ttgaatactg cctcaaggac     240
aggatgaact ttgacatccc tgaggagatt aagcagctgc agcagttcca gaaggaggac     300
gccgcattga ccatctatga gatgctccag aacatctttg ctattttcag acaagattca     360
tctagcactg gctggaatga gactattgtt gagaacctcc tggctaatgt ctatcatcag     420

```
ataaaccatc tgaagacagt cctggaagaa aaactggaga aagaagattt caccagggga      480
aaactcatga gcagtctgca cctgaaaaga tattatggga ggattctgca ttacctgaag      540
gccaaggagt acagtcactg tgcctggacc atagtcagag tggaaatcct aaggaacttt      600
tacttcatta acagacttac aggttacctc cgaaactgaa gatctcctag cctgtgcctc      660
tgggactgga caattgcttc aagcattctt caaccagcag atgctgttta agtgactgat      720
ggctaatgta ctgcatatga aaggacacta gaagattttg aaattttat taaattatga       780 gttattttta tttatttaaa ttttatttg gaaaataaat tattttggt gcaaaagtca        840
```

<210> SEQ ID NO 87
<211> LENGTH: 1240
<212> TYPE: DNA
<213> ORGANISM: Homo sapiens

<400> SEQUENCE: 87

```
cacattgttc tgatcatctg aagatcagct attagaagag aaagatcagt taagtccttt       60
ggacctgatc agcttgatac aagaactact gatttcaact tctttggctt aattctctcg      120
gaaacgatga aatatacaag ttatatcttg gcttttcagc tctgcatcgt tttgggttct      180
cttggctgtt actgccagga cccatatgta aaagaagcag aaaaccttaa gaaatatttt      240
aatgcaggtc attcagatgt agcggataat ggaactcttt tcttaggcat tttgaagaat      300 tggaagagg agagtgacag aaaaataatg cagagccaaa ttgtctcctt ttacttcaaa       360 cttttttaaaa actttaaaga tgaccagagc atccaaaaga gtgtggagac catcaaggaa     420
gacatgaatg tcaagttttt caatagcaac aaaaagaaac gagatgactt cgaaaagctg      480
actaattatt cggtaactga cttgaatgtc caacgcaaag caatacatga actcatccaa      540
gtgatggctg aactgtcgcc agcagctaaa acagggaagc gaaaaaggag tcagatgctg      600
tttcgaggtc gaagagcatc ccagtaatgg ttgtcctgcc tgcaatattt gaattttaaa      660
tctaaatcta tttattaata tttaacatta tttatatggg gaatatattt ttagactcat      720
caatcaaata gtatttata atagcaactt ttgtgtaatg aaaatgaata tctattaata      780
tatgtattat ttataattcc tatatcctgt gactgtctca cttaatcctt tgttttctga      840
ctaattaggc aaggctatgt gattacaagg ctttatctca ggggccaact aggcagccaa      900
cctaagcaag atcccatggg ttgtgtgttt atttcacttg atgatacaat gaacacttat      960
aagtgaagtg atactatcca gttactgccg gtttgaaaat atgcctgcaa tctgagccag     1020
tgctttaatg gcatgtcaga cagaacttga atgtgtcagg tgaccctgat gaaaacatag     1080
catctcagga gatttcatgc ctggtgcttc caaatattgt tgacaactgt gactgtaccc     1140
aaatggaaag taactcattt gttaaaatta tcaatatcta atatatatga ataaagtgta     1200
agttcacaac aaaaaaaaaa aaaaaaaaaa aaaaaaaaa                            1240
```

<210> SEQ ID NO 88
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 88

```
ctggttgcc                                                                9
```

```
<210> SEQ ID NO 89
<211> LENGTH: 9
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89 gaaggcaga                                                              9

<210> SEQ ID NO 90
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
gatcatctca tggaggacag                                                 20
```